United States Patent
Gros et al.

(10) Patent No.: US 9,346,890 B2
(45) Date of Patent: May 24, 2016

(54) ANTIGEN BINDING PROTEINS THAT BIND ERBB3

(71) Applicant: Sorrento Therapeutics, Inc., San Diego, CA (US)

(72) Inventors: Edwige Gros, San Diego, CA (US); Yanliang Zhang, San Diego, CA (US); Heyue Zhou, San Diego, CA (US)

(73) Assignee: Sorrento Therapeutics, Inc., San Diego, CA (US)

( * ) Notice: Subject to any disclaimer, the term of this patent is extended or adjusted under 35 U.S.C. 154(b) by 0 days.

(21) Appl. No.: 14/061,548

(22) Filed: Oct. 23, 2013

(65) Prior Publication Data
US 2014/0120092 A1 May 1, 2014

Related U.S. Application Data

(60) Provisional application No. 61/718,657, filed on Oct. 25, 2012.

(51) Int. Cl.
*A61K 39/395* (2006.01)
*C07K 16/40* (2006.01)
*C07K 16/32* (2006.01)

(52) U.S. Cl.
CPC ............... *C07K 16/40* (2013.01); *C07K 16/32* (2013.01); *C07K 2317/21* (2013.01); *C07K 2317/33* (2013.01); *C07K 2317/73* (2013.01); *C07K 2317/76* (2013.01)

(58) Field of Classification Search
None
See application file for complete search history.

(56) References Cited

FOREIGN PATENT DOCUMENTS

| WO | 2007/141274 | 12/2007 |
|---|---|---|
| WO | 2009/079212 | 6/2009 |

OTHER PUBLICATIONS

Rudikoff et al. (Proc Natl Acad Sci USA 1982 vol. 79 p. 1979).*
MacCallum et al. J. Mol. Biol. (1996) 262: 732-745.*
Xu et al (Immunity, 2000, 13:37-45).*
Pascalis et al. (The Journal of Immunology (2002) 169, 3076-3084).*
Casset et al. (BBRC 2003, 307:198-205).*
Written Opinion and Search Report for corresponding PCT/US13/66427.
Aueisicchio et al. "The promise or anti-ErbB3 monocolonals as new cancer therapeutics" Oncotarget. Aug. 10, 2012, 3(8):744-758.
Schoeberl et al., "Therapeutically targeting ErbB3: a key node in ligand-induced activation of the ErbB3 receptor-P13K axis" Sci. Signal 2009, 2(777)ras31.
Schoeberl et al. "An ErbB3 antibody, MM-121, is active in cancers with ligand-dependent activation" Cancer Res. 2010, 70(6):24185-2494.
McDonagh et al., "Antitumor activity of a novel bispecific antibody that targets the ErbB2/ErbB3 oncogenic unit and inhibits heregulin-induced activation of ErbB3" Mol. Cancer Ther., Mar. 2012, 11(3):582-593.
Aurisicchio et al., "The promise of anti-ErbB3 monoclonals as new cancer therapeutics" Oncotarget 3:744-758, 2012.
Chan, "Therapeutic Antibodies for autoimmunity and inflammation" Nature Reviews Immunology 10:301-316, 2010.
Schoeberl et al., "Therapeutically targeting ErbB3: A key node in ligand-induced activation of the ErbB Receptor-P13K axis" Science Signaling 2(77):1-14, 2009.
Wang et al. "Antibody structure, instability and formulation" J. Pharm. Sciences 96(1):1-26, 2007.

* cited by examiner

*Primary Examiner* — Laura B Goddard
(74) *Attorney, Agent, or Firm* — McCarter & English, LLP; Danielle L. Herritt; Cristin H. Cowles

(57) ABSTRACT

There is disclosed compositions and methods relating to or derived from anti-ErbB3 antibodies. More specifically, there is disclosed fully human antibodies that bind ErbB3, ErbB3-binding fragments and derivatives of such antibodies, and ErbB3-binding polypeptides comprising such fragments. Further still, there is disclosed nucleic acids encoding such antibodies, antibody fragments and derivatives and polypeptides, cells comprising such polynucleotides, methods of making such antibodies, antibody fragments and derivatives and polypeptides, and methods of using such antibodies, antibody fragments and derivatives and polypeptides, including methods of treating or diagnosing subjects having ErbB3 related disorders or conditions, including various inflammatory disorders and various cancers.

4 Claims, 14 Drawing Sheets

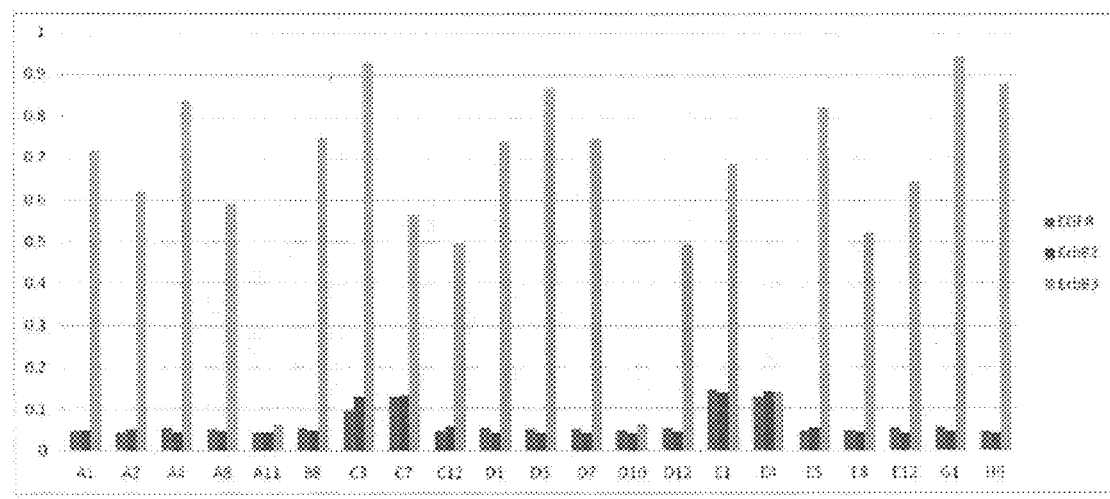
Figure 1A. Binding Specificity of ErbB3 binders

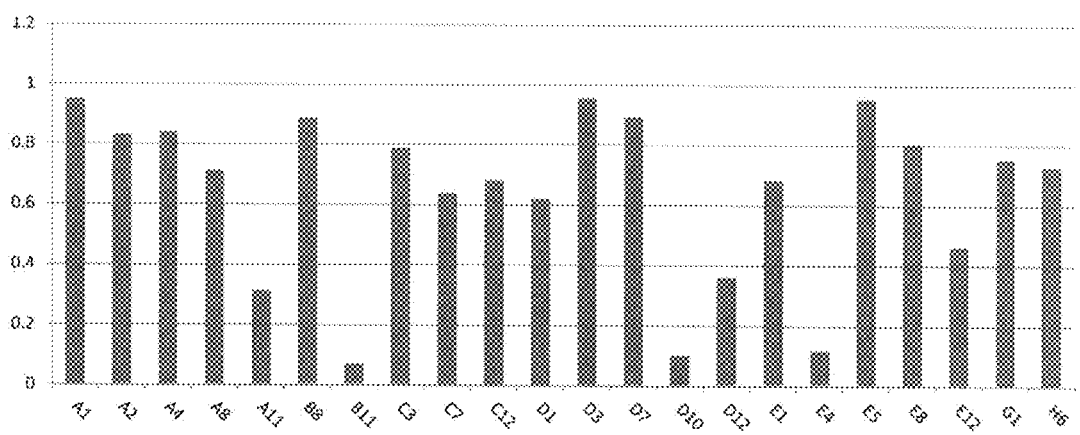
Figure 1B. Cross-reaction with mouse ErbB3

Binding of selected anti-ErbB3 antibodies to Cell Surface.

Figure 2 (Continued)
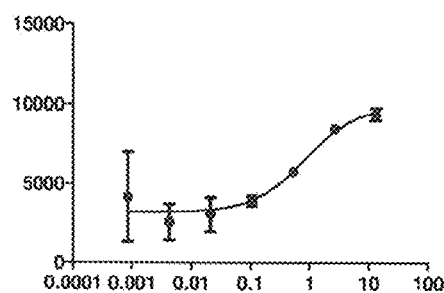
C03
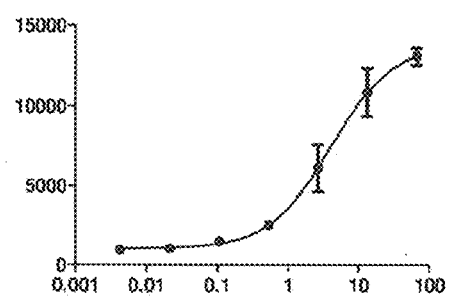
D01
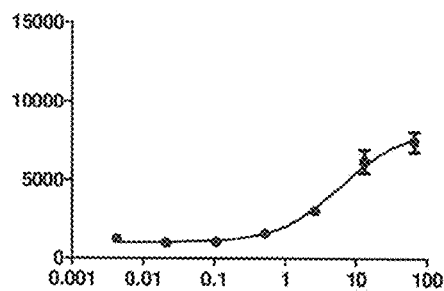
D03
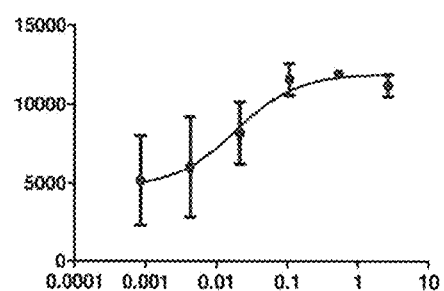
D04
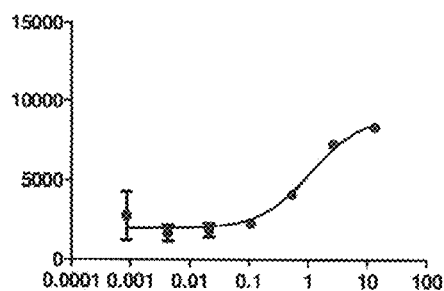
D07
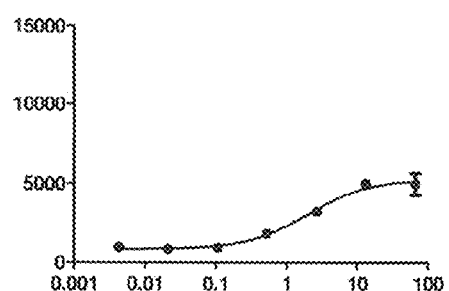
D08

Figure 2 (continued)
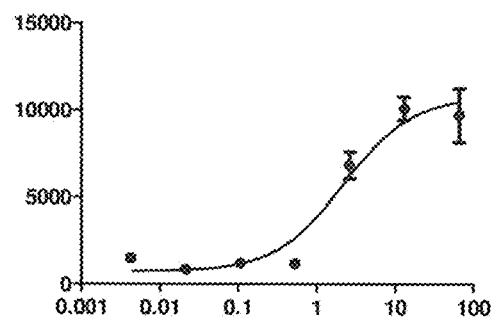
D10
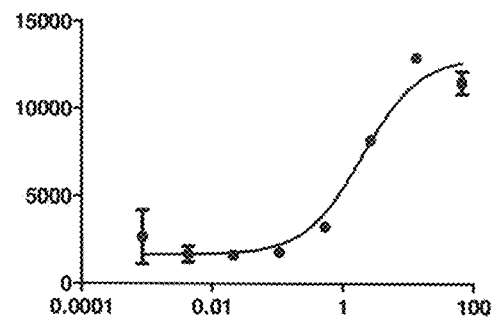
E01
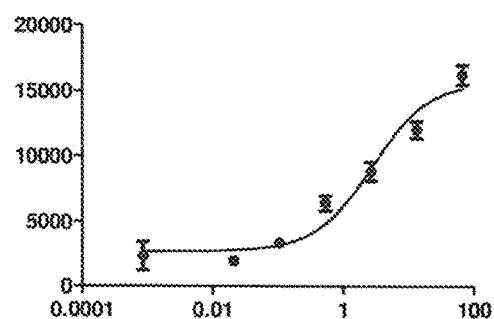
E08

Figure 3 HPLC-ANSEC Profiles of selected anti-ErbB3 antibodies

Fig 4. Inhibition of Heregulin-stimulated MCF7 Proliferation

Fig. 7 Blocking of Heregulin-HER3 interaction

Fig 8. HER3 Receptor Internalization induced by Anti-Her3 antibody

Fig 9. Inhibition of MCF7 by anti-ErbB3 antibody

ANTIGEN BINDING PROTEINS THAT BIND ERBB3

CROSS-REFERENCE TO RELATED APPLICATION

This patent application claims priority from U.S. provisional patent application 61/718,657 filed 25 Oct. 2012.

TECHNICAL FIELD

The present disclosure provides compositions and methods relating to or derived from anti-ErbB3 antibodies. More specifically, the present disclosure provides human antibodies that bind ErbB3, ErbB3-binding fragments and derivatives of such antibodies, and ErbB3-binding polypeptides comprising such fragments. Further still, the present disclosure provides nucleic acids encoding such antibodies, antibody fragments and derivatives and polypeptides, cells comprising such polynucleotides, methods of making such antibodies, antibody fragments and derivatives and polypeptides, and methods of using such antibodies, antibody fragments and derivatives and polypeptides, including methods of treating or diagnosing subjects having ErbB3 related disorders or conditions, including various inflammatory disorders and various cancers.

BACKGROUND

HER3/c-ErbB3 (referred to herein as ErbB3) is a member of the epidermal growth factor receptor (EGFR) family. ErbB3 binds neuregulin/heregulin (NRG/HRG). Receptors in the EGFR family are single transmembrane receptors with an intracellular tyrosine kinase domain. While the other EGFR family members (such as EGFR/HER1/ErbB1, HER2/ErbB2, and HER4/ErbB4) each have tyrosine kinase activity, ErbB3 has little or no tyrosine kinase activity, and thus is "kinase-dead."

The extracellular domain (ECD) of the EGFR family contains four domains. Domains 1 and 3 (also known as domains L1 and L2) are responsible for ligand binding. Cysteine-rich domains 2 and 4 (also known as domains C1 and C2) are involved in dimerization with receptor partners. Upon ligand binding, the ECD undergoes conformational changes. The interaction of domains 2 and 4, which maintains the tethered (inactive) conformation of the receptor, is relieved, and an extended (active) conformation is adopted. The extended conformation favors dimerization with other receptor partners. HER2/ErbB2 is the only exception to this general rule, i.e., Her2-ECD is constitutively in the extended conformation.

Overexpression of ErbB3 is associated with poor prognosis in various carcinomas (e.g., breast, ovarian, prostate, colorectal, pancreatic, gastric, and head and neck cancers). Overexpression of ErbB3 also correlates with local to distal metastasis in lung, gastric, and colorectal cancers, and bone invasion in prostate cancer (Sithanandam et al., 2008, *Cancer Gene Therapy* 15:413). Overexpression of ErbB3 has been linked to resistance to several cancer treatments, including treatment with EGFR tyrosine kinase inhibitors in non-small cell lung cancer (NSCLC) and head and neck cancers, treatment with Her2 inhibitor in breast cancers, and treatment with radiotherapy in pancreatic cancers. Moreover, overexpression of NRG, a ligand for ErbB3, was also linked to resistance to EGFR tyrosine kinase inhibitor treatment. Chen et al. describe the use of anti-ErbB3 monoclonal antibodies that inhibit NRG function and show growth inhibitory activity against breast and ovarian cancer cells (Chen et al., 1996, *J. Biol. Chem.* 271: 7620).

ErbB3 has been found to be overexpressed in breast (Lemoine et al., *Br. J. Cancer,* 66:1116-1121 (1992)), gastrointestinal (Poller et al., *J. Pathol.,* 168:275-280 (1992), Rajkumer et al., *J. Pathol.,* 170:271-278 (1993), and Sanidas et al., *Int. J. Cancer,* 54:935-940 (1993)), and pancreatic cancers (Lemoine et at, *J. Pathol.,* 168:269-273 (1992), and Friess et al., *Clinical Cancer Research,* 1:1413-1420 (1995)).

Therefore, there is a need in the art for an improved anti-ErbB3 antibodies that can be used as therapeutic agents.

SUMMARY

The present disclosure provides a fully human antibody of an IgG class that binds to an ErbB3 epitope with a binding affinity of at least $10^{-6}$M, which has a heavy chain variable domain sequence that is at least 95% identical to the amino acid sequences selected from the group consisting of SEQ ID NO. 1, SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 25, SEQ ID NO. 27, SEQ ID NO. 29, SEQ ID NO. 31, SEQ ID NO. 33, SEQ ID NO. 35, SEQ ID NO. 37, SEQ ID NO. 39, SEQ ID NO. 41, SEQ ID NO. 43, SEQ ID NO. 45, SEQ ID NO. 47, SEQ ID NO.49, SEQ ID NO. 51, SEQ ID NO. 53, SEQ ID NO. 55, SEQ ID NO. 57, SEQ ID NO. 59, and combinations thereof, and that has a light chain variable domain sequence that is at least 95% identical to the amino acid sequences selected from the group consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 24, SEQ ID NO. 26, SEQ ID NO. 28, SEQ ID NO. 30, SEQ ID NO. 32, SEQ ID NO. 34, SEQ ID NO. 36, SEQ ID NO. 38, SEQ ID NO. 40, SEQ ID NO. 42, SEQ ID NO. 44, SEQ ID NO. 46, SEQ ID NO. 48, SEQ ID NO. 50, SEQ ID NO. 52, SEQ ID NO. 54, SEQ ID NO. 56, SEQ ID NO. 58, SEQ ID NO. 60, and combinations thereof. Preferably, the fully human antibody has both a heavy chain and a light chain wherein the antibody has a heavy chain/light chain variable domain sequence selected from the group consisting of SEQ ID NO. 1/SEQ ID NO. 2 (called A01 herein), SEQ ID NO. 3/SEQ ID NO. 4 (called A02 herein), SEQ ID NO. 5/SEQ ID NO. 6 (called A04 herein), SEQ ID NO. 7/SEQ ID NO. 8 (called A08 herein), SEQ ID NO. 9/SEQ ID NO. 10 (called A11 herein), SEQ ID NO. 11/SEQ ID NO. 12 (called A12 herein), SEQ ID NO. 13/SEQ ID NO. 14 (called B01 herein), SEQ ID NO. 15/SEQ ID NO. 16 (called B03 herein), SEQ ID NO. 17/SEQ ID NO. 18 (called B04 herein), SEQ ID NO. 19/SEQ ID NO. 20 (called B05 herein), SEQ ID NO. 21/SEQ ID NO. 22 (called B08 herein), SEQ ID NO. 23/SEQ ID NO. 24 (called B10 herein), SEQ ID NO. 25/SEQ ID NO. 26 (called B11 herein), SEQ ID NO. 27/SEQ ID NO. 28 (called C03 herein), SEQ ID NO. 29/SEQ ID NO. 30 (called C07 herein), SEQ ID NO. 31/SEQ ID NO. 32 (called C10 herein), SEQ ID NO. 33/SEQ ID NO. 34 (called C12 herein), SEQ ID NO. 35/SEQ ID NO. 36 (called D01 herein), SEQ ID NO. 37/SEQ ID NO. 38 (called D03 herein), SEQ ID NO. 39/SEQ ID NO. 40 (called D04 herein), SEQ ID NO. 41/SEQ ID NO. 42 (called D07 herein), SEQ ID NO. 43/SEQ ID NO. 44 (called D08 herein), SEQ ID NO. 45/SEQ ID NO. 46 (called D10 herein), SEQ ID NO. 47/SEQ ID NO. 48 (called D11 herein), SEQ ID NO. 49/SEQ ID NO. 50 (called E04 herein), SEQ ID NO. 51/SEQ ID NO. 52 (called E05 herein), SEQ ID NO. 53/SEQ ID NO. 54 (called E08 herein), SEQ ID NO. 55/SEQ ID NO. 56 (called F10 herein), SEQ ID NO. 57/SEQ ID NO. 58 (called G01 herein), SEQ ID NO. 59/SEQ ID NO. 60 (called H06 herein), and combinations thereof.

The present disclosure provides a fully human antibody Fab fragment, having a variable domain region from a heavy chain and a variable domain region from a light chain, wherein the heavy chain variable domain sequence that is at least 95% identical to the amino acid sequences selected from the group consisting of SEQ ID NO. 1, SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 25, SEQ ID NO. 27, SEQ ID NO. 29, SEQ ID NO. 31, SEQ ID NO. 33, SEQ ID NO. 35, SEQ ID NO. 37, SEQ ID NO. 39, SEQ ID NO. 41, SEQ ID NO. 43, SEQ ID NO. 45, SEQ ID NO. 47, SEQ ID NO.49, SEQ ID NO. 51, SEQ ID NO. 53, SEQ ID NO. 55, SEQ ID NO. 57, SEQ ID NO. 59, and combinations thereof, and that has a light chain variable domain sequence that is at least 95% identical to the amino acid sequences selected from the group consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 24, SEQ ID NO. 26, SEQ ID NO. 28, SEQ ID NO. 30, SEQ ID NO. 32, SEQ ID NO. 34, SEQ ID NO. 36, SEQ ID NO. 38, SEQ ID NO. 40, SEQ ID NO. 42, SEQ ID NO. 44, SEQ ID NO. 46, SEQ ID NO. 48, SEQ ID NO. 50, SEQ ID NO. 52, SEQ ID NO. 54, SEQ ID NO. 56, SEQ ID NO. 58, SEQ ID NO. 60, and combinations thereof. Preferably, the fully human antibody Fab fragment has both a heavy chain variable domain region and a light chain variable domain region wherein the antibody has a heavy chain/light chain variable domain sequence selected from the group consisting of SEQ ID NO. 1/SEQ ID NO. 2, SEQ ID NO. 3/SEQ ID NO. 4, SEQ ID NO. 5/SEQ ID NO. 6, SEQ ID NO. 7/SEQ ID NO. 8, SEQ ID NO. 9/SEQ ID NO. 10, SEQ ID NO. 11/SEQ ID NO. 12, SEQ ID NO. 13/SEQ ID NO. 14, SEQ ID NO. 15/SEQ ID NO. 16, SEQ ID NO. 17/SEQ ID NO. 18, SEQ ID NO. 19/SEQ ID NO. 20, SEQ ID NO. 21/SEQ ID NO. 22, SEQ ID NO. 23/SEQ ID NO. 24, SEQ ID NO. 25/SEQ ID NO. 26, SEQ ID NO. 27/SEQ ID NO. 28, SEQ ID NO. 29/SEQ ID NO. 30, SEQ ID NO. 31/SEQ ID NO. 32, SEQ ID NO. 33/SEQ ID NO. 34, SEQ ID NO. 35/SEQ ID NO. 36, SEQ ID NO. 37/SEQ ID NO. 38, SEQ ID NO. 39/SEQ ID NO. 40, SEQ ID NO. 41/SEQ ID NO. 42, SEQ ID NO. 43/SEQ ID NO. 44, SEQ ID NO. 45/SEQ ID NO. 46, SEQ ID NO. 47/SEQ ID NO. 48, SEQ ID NO. 49/SEQ ID NO. 50, SEQ ID NO. 51/SEQ ID NO. 52, SEQ ID NO. 53/SEQ ID NO. 54, SEQ ID NO. 55/SEQ ID NO. 56, SEQ ID NO. 57/SEQ ID NO. 58, SEQ ID NO. 59/SEQ ID NO. 60, and combinations thereof.

The present disclosure provides a single chain human antibody, having a variable domain region from a heavy chain and a variable domain region from a light chain and a peptide linker connection the heavy chain and light chain variable domain regions, wherein the heavy chain variable domain sequence that is at least 95% identical to the amino acid sequences selected from the group consisting of SEQ ID NO. 1, SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 25, SEQ ID NO. 27, SEQ ID NO. 29, SEQ ID NO. 31, SEQ ID NO. 33, SEQ ID NO. 35, SEQ ID NO. 37, SEQ ID NO. 39, SEQ ID NO. 41, SEQ ID NO. 43, SEQ ID NO. 45, SEQ ID NO. 47, SEQ ID NO.49, SEQ ID NO. 51, SEQ ID NO. 53, SEQ ID NO. 55, SEQ ID NO. 57, SEQ ID NO. 59, and combinations thereof, and that has a light chain variable domain sequence that is at least 95% identical to the amino acid sequences selected from the group consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 24, SEQ ID NO. 26, SEQ ID NO. 28, SEQ ID NO. 30, SEQ ID NO. 32, SEQ ID NO. 34, SEQ ID NO. 36, SEQ ID NO. 38, SEQ ID NO. 40, SEQ ID NO. 42, SEQ ID NO. 44, SEQ ID NO. 46, SEQ ID NO. 48, SEQ ID NO. 50, SEQ ID NO. 52, SEQ ID NO. 54, SEQ ID NO. 56, SEQ ID NO. 58, SEQ ID NO. 60, and combinations thereof. Preferably, the fully human single chain antibody has both a heavy chain variable domain region and a light chain variable domain region, wherein the single chain fully human antibody has a heavy chain/light chain variable domain sequence selected from the group consisting of SEQ ID NO. 1/SEQ ID NO. 2, SEQ ID NO. 3/SEQ ID NO. 4, SEQ ID NO. 5/SEQ ID NO. 6, SEQ ID NO. 7/SEQ ID NO. 8, SEQ ID NO. 9/SEQ ID NO. 10, SEQ ID NO. 11/SEQ ID NO. 12, SEQ ID NO. 13/SEQ ID NO. 14, SEQ ID NO. 15/SEQ ID NO. 16, SEQ ID NO. 17/SEQ ID NO. 18, SEQ ID NO. 19/SEQ ID NO. 20, SEQ ID NO. 21/SEQ ID NO. 22, SEQ ID NO. 23/SEQ ID NO. 24, SEQ ID NO. 25/SEQ ID NO. 26, SEQ ID NO. 27/SEQ ID NO. 28, SEQ ID NO. 29/SEQ ID NO. 30, SEQ ID NO. 31/SEQ ID NO. 32, SEQ ID NO. 33/SEQ ID NO. 34, SEQ ID NO. 35/SEQ ID NO. 36, SEQ ID NO. 37/SEQ ID NO. 38, SEQ ID NO. 39/SEQ ID NO. 40, SEQ ID NO. 41/SEQ ID NO. 42, SEQ ID NO. 43/SEQ ID NO. 44, SEQ ID NO. 45/SEQ ID NO. 46, SEQ ID NO. 47/SEQ ID NO. 48, SEQ ID NO. 49/SEQ ID NO. 50, SEQ ID NO. 51/SEQ ID NO. 52, SEQ ID NO. 53/SEQ ID NO. 54, SEQ ID NO. 55/SEQ ID NO. 56, SEQ ID NO. 57/SEQ ID NO. 58, SEQ ID NO. 59/SEQ ID NO. 60, and combinations thereof.

The present disclosure further provides a method for treating a broad spectrum of mammalian cancers, comprising administering an effective amount of an anti-ErbB3 polypeptide, wherein the anti-ErbB3 polypeptide is selected from the group consisting of a fully human antibody of an IgG class that binds to an ErbB3 epitope with a binding affinity of at least $10^{-6}$M, a fully human antibody Fab fragment, having a variable domain region from a heavy chain and a variable domain region from a light chain, a single chain human antibody, having a variable domain region from a heavy chain and a variable domain region from a light chain and a peptide linker connection the heavy chain and light chain variable domain regions, and combinations thereof;

wherein the fully human antibody has a heavy chain variable domain sequence that is at least 95% identical to the amino acid sequences selected from the group consisting of SEQ ID NO. 1, SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 25, SEQ ID NO. 27, SEQ ID NO. 29, SEQ ID NO. 31, SEQ ID NO. 33, SEQ ID NO. 35, SEQ ID NO. 37, SEQ ID NO. 39, SEQ ID NO. 41, SEQ ID NO. 43, SEQ ID NO. 45, SEQ ID NO. 47, SEQ ID NO.49, SEQ ID NO. 51, SEQ ID NO. 53, SEQ ID NO. 55, SEQ ID NO. 57, SEQ ID NO. 59, and combinations thereof, and that has a light chain variable domain sequence that is at least 95% identical to the amino acid sequences selected from the group consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 24, SEQ ID NO. 26, SEQ ID NO. 28, SEQ ID NO. 30, SEQ ID NO. 32, SEQ ID NO. 34, SEQ ID NO. 36, SEQ ID NO. 38, SEQ ID NO. 40, SEQ ID NO. 42, SEQ ID NO. 44, SEQ ID NO. 46, SEQ ID NO. 48, SEQ ID NO. 50, SEQ ID NO. 52, SEQ ID NO. 54, SEQ ID NO. 56, SEQ ID NO. 58, SEQ ID NO. 60, and combinations thereof;

wherein the fully human antibody Fab fragment has the heavy chain variable domain sequence that is at least 95% identical to the amino acid sequences selected from the group consisting of SEQ ID NO. 1, SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 25, SEQ ID NO. 27, SEQ ID NO. 29, SEQ ID NO. 31, SEQ ID NO. 33, SEQ ID NO. 35, SEQ ID NO. 37, SEQ ID NO. 39, SEQ ID NO. 41, SEQ ID NO. 43, SEQ ID NO. 45, SEQ ID NO. 47, SEQ ID NO.49, SEQ ID NO. 51, SEQ ID NO. 53, SEQ ID NO. 55, SEQ ID NO. 57, SEQ ID NO. 59, and combinations thereof, and that has the light chain variable domain sequence that is at least 95% identical to the amino acid sequences selected from the group consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 24, SEQ ID NO. 26, SEQ ID NO. 28, SEQ ID NO. 30, SEQ ID NO. 32, SEQ ID NO. 34, SEQ ID NO. 36, SEQ ID NO. 38, SEQ ID NO. 40, SEQ ID NO. 42, SEQ ID NO. 44, SEQ ID NO. 46, SEQ ID NO. 48, SEQ ID NO. 50, SEQ ID NO. 52, SEQ ID NO. 54, SEQ ID NO. 56, SEQ ID NO. 58, SEQ ID NO. 60, and combinations thereof; and wherein the single chain human antibody has the heavy chain variable domain sequence that is at least 95% identical to the amino acid sequences selected from the group consisting of SEQ ID NO. 1, SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 25, SEQ ID NO. 27, SEQ ID NO. 29, SEQ ID NO. 31, SEQ ID NO. 33, SEQ ID NO. 35, SEQ ID NO. 37, SEQ ID NO. 39, SEQ ID NO. 41, SEQ ID NO. 43, SEQ ID NO. 45, SEQ ID NO. 47, SEQ ID NO.49, SEQ ID NO. 51, SEQ ID NO. 53, SEQ ID NO. 55, SEQ ID NO. 57, SEQ ID NO. 59, and combinations thereof, and that has the light chain variable domain sequence that is at least 95% identical to the amino acid sequences selected from the group consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 24, SEQ ID NO. 26, SEQ ID NO. 28, SEQ ID NO. 30, SEQ ID NO. 32, SEQ ID NO. 34, SEQ ID NO. 36, SEQ ID NO. 38, SEQ ID NO. 40, SEQ ID NO. 42, SEQ ID NO. 44, SEQ ID NO. 46, SEQ ID NO. 48, SEQ ID NO. 50, SEQ ID NO. 52, SEQ ID NO. 54, SEQ ID NO. 56, SEQ ID NO. 58, SEQ ID NO. 60, and combinations thereof.

Preferably, the fully human antibody has both a heavy chain and a light chain wherein the antibody has a heavy chain/light chain variable domain sequence selected from the group consisting of SEQ ID NO. 1/SEQ ID NO. 2 (called A01 herein), SEQ ID NO. 3/SEQ ID NO. 4 (called A02 herein), SEQ ID NO. 5/SEQ ID NO. 6 (called A04 herein), SEQ ID NO. 7/SEQ ID NO. 8 (called A08 herein), SEQ ID NO. 9/SEQ ID NO. 10 (called A11 herein), SEQ ID NO. 11/SEQ ID NO. 12 (called A12 herein), SEQ ID NO. 13/SEQ ID NO. 14 (called B01 herein), SEQ ID NO. 15/SEQ ID NO. 16 (called B03 herein), SEQ ID NO. 17/SEQ ID NO. 18 (called B04 herein), SEQ ID NO. 19/SEQ ID NO. 20 (called B05 herein), SEQ ID NO. 21/SEQ ID NO. 22 (called B08 herein), SEQ ID NO. 23/SEQ ID NO. 24 (called B10 herein), SEQ ID NO. 25/SEQ ID NO.26 (called B11 herein), SEQ ID NO. 27/SEQ ID NO. 28 (called C03 herein), SEQ ID NO. 29/SEQ ID NO. 30 (called C07 herein), SEQ ID NO. 31/SEQ ID NO. 32 (called C10 herein), SEQ ID NO. 33/SEQ ID NO. 34 (called C12 herein), SEQ ID NO. 35/SEQ ID NO. 36 (called D01 herein), SEQ ID NO. 37/SEQ ID NO. 38 (called D03 herein), SEQ ID NO. 39/SEQ ID NO. 40 (called D04 herein), SEQ ID NO. 41/SEQ ID NO. 42 (called D07 herein), SEQ ID NO. 43/SEQ ID NO. 44 (called D08 herein), SEQ ID NO. 45/SEQ ID NO. 46 (called D10 herein), SEQ ID NO. 47/SEQ ID NO. 48 (called D11 herein), SEQ ID NO. 49/SEQ ID NO. 50 (called E04 herein), SEQ ID NO. 51/SEQ ID NO. 52 (called E05 herein), SEQ ID NO. 53/SEQ ID NO. 54 (called E08 herein), SEQ ID NO. 55/SEQ ID NO. 56 (called F10 herein), SEQ ID NO. 57/SEQ ID NO. 58 (called G01 herein), SEQ ID NO. 59/SEQ ID NO. 60 (called H06 herein), and combinations thereof. Preferably, the fully human antibody Fab fragment has both a heavy chain variable domain region and a light chain variable domain region wherein the antibody has a heavy chain/light chain variable domain sequence selected from the group consisting of SEQ ID NO. 1/SEQ ID NO. 2 (called A01 herein), SEQ ID NO. 3/SEQ ID NO. 4 (called A02 herein), SEQ ID NO. 5/SEQ ID NO. 6 (called A04 herein), SEQ ID NO. 7/SEQ ID NO. 8 (called A08 herein), SEQ ID NO. 9/SEQ ID NO. 10 (called A11 herein), SEQ ID NO. 11/SEQ ID NO. 12 (called A12 herein), SEQ ID NO. 13/SEQ ID NO. 14 (called B01 herein), SEQ ID NO. 15/SEQ ID NO. 16 (called B03 herein), SEQ ID NO. 17/SEQ ID NO. 18 (called B04 herein), SEQ ID NO. 19/SEQ ID NO. 20 (called B05 herein), SEQ ID NO. 21/SEQ ID NO. 22 (called B08 herein), SEQ ID NO. 23/SEQ ID NO. 24 (called B10 herein), SEQ ID NO. 25/SEQ ID NO.26 (called B11 herein), SEQ ID NO. 27/SEQ ID NO. 28 (called C03 herein), SEQ ID NO. 29/SEQ ID NO. 30 (called C07 herein), SEQ ID NO. 31/SEQ ID NO. 32 (called C10 herein), SEQ ID NO. 33/SEQ ID NO. 34 (called C12 herein), SEQ ID NO. 35/SEQ ID NO. 36 (called D01 herein), SEQ ID NO. 37/SEQ ID NO. 38 (called D03 herein), SEQ ID NO. 39/SEQ ID NO. 40 (called D04 herein), SEQ ID NO. 41/SEQ ID NO. 42 (called D07 herein), SEQ ID NO. 43/SEQ ID NO. 44 (called D08 herein), SEQ ID NO. 45/SEQ ID NO. 46 (called D10 herein), SEQ ID NO. 47/SEQ ID NO. 48 (called D11 herein), SEQ ID NO. 49/SEQ ID NO. 50 (called E04 herein), SEQ ID NO. 51/SEQ ID NO. 52 (called E05 herein), SEQ ID NO. 53/SEQ ID NO. 54 (called E08 herein), SEQ ID NO. 55/SEQ ID NO. 56 (called F10 herein), SEQ ID NO. 57/SEQ ID NO. 58 (called G01 herein), SEQ ID NO. 59/SEQ ID NO. 60 (called H06 herein), and combinations thereof. Preferably, the fully human single chain antibody has both a heavy chain variable domain region and a light chain variable domain region, wherein the single chain fully human antibody has a heavy chain/light chain variable domain sequence selected from the group consisting of SEQ ID NO. 1/SEQ ID NO. 2, SEQ ID NO. 3/SEQ ID NO. 4, SEQ ID NO. 5/SEQ ID NO. 6, SEQ ID NO. 7/SEQ ID NO. 8, SEQ ID NO. 9/SEQ ID NO. 10, SEQ ID NO. 11/SEQ ID NO. 12, SEQ ID NO. 13/SEQ ID NO. 14, SEQ ID NO. 15/SEQ ID NO. 16, SEQ ID NO. 17/SEQ ID NO. 18, SEQ ID NO. 19/SEQ ID NO. 20, SEQ ID NO. 21/SEQ ID NO. 22, SEQ ID NO. 23/SEQ ID NO. 24, SEQ ID NO. 25/SEQ ID NO. 26, SEQ ID NO. 27/SEQ ID NO. 28, SEQ ID NO. 29/SEQ ID NO. 30, SEQ ID NO. 31/SEQ ID NO. 32, SEQ ID NO. 33/SEQ ID NO. 34, SEQ ID NO. 35/SEQ ID NO. 36, SEQ ID NO. 37/SEQ ID NO. 38, SEQ ID NO. 39/SEQ ID NO. 40, SEQ ID NO. 41/SEQ ID NO. 42, SEQ ID NO. 43/SEQ ID NO. 44, SEQ ID NO. 45/SEQ ID NO. 46, SEQ ID NO. 47/SEQ ID NO. 48, SEQ ID NO. 49/SEQ ID NO. 50, SEQ ID NO. 51/SEQ ID NO. 52, SEQ ID NO. 53/SEQ ID NO. 54, SEQ ID NO. 55/SEQ ID NO. 56, SEQ ID NO. 57/SEQ ID NO. 58, SEQ ID NO. 59/SEQ ID NO. 60, and combinations thereof.

Preferably, the broad spectrum of mammalian cancers to be treated the cancer is an ErbB3-positive cancer. Preferably, the broad spectrum of mammalian cancers to be treated is selected from the group consisting of carcinomas, prostate cancer, non-small cell lung cancer, breast cancer, endometrial cancer, ovarian cancer, gastric cancers, head and neck cancers, and colon cancer.

BRIEF DESCRIPTION OF THE FIGURES

FIG. 1A shows the binding of anti-ErbB3 antibodies to Human recombinant ErbB3 Protein, as measured by ELISA. Recombinant Human Proteins EGFR and ErbB2, other members of the ErbB Family, were used as controls. The results show that anti-ErbB3 antibodies bind specifically to ErbB3.

FIG. 1B shows the results of a Mouse Cross Reactivity ELISA test. The strong signal detected shows that most of anti-Human ErbB3 antibodies also bind to Mouse recombinant ErbB3 Protein.

DETAILED DESCRIPTION

Figure 2:
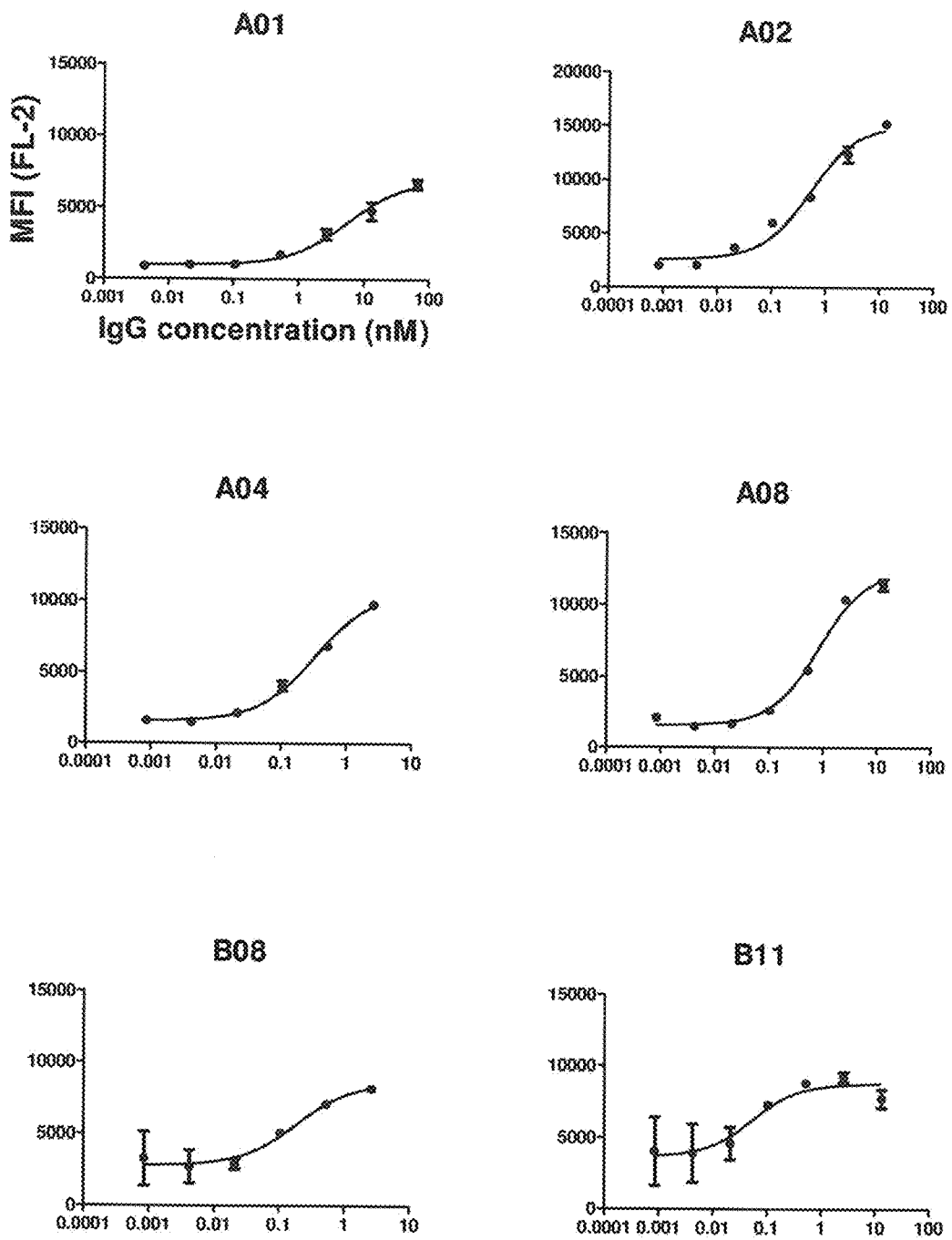
FIG. 2 shows the binding of exemplary anti-ErbB3 Antibodies to Human ErbB3 expressed at the Cell Surface (MCF7), as analyzed by Flow Cytometry.

The present disclosure provides a fully human antibody of an IgG class that binds to an ErbB3 epitope with a binding affinity of $10^{-6}$M or less, that has a heavy chain variable domain sequence that is at least 95% identical to the amino acid sequences selected from the group consisting of SEQ ID NO. 1, SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 25, SEQ ID NO. 27, SEQ ID NO. 29, SEQ ID NO. 31, SEQ ID NO. 33, SEQ ID NO. 35, SEQ ID NO. 37, SEQ ID NO. 39, SEQ ID NO. 41, SEQ ID NO. 43, SEQ ID NO. 45, SEQ ID NO. 47, SEQ ID NO.49, SEQ ID NO. 51, SEQ ID NO. 53, SEQ ID NO. 55, SEQ ID NO. 57, SEQ ID NO. 59, and combinations thereof, and that has a light chain variable domain sequence that is at least 95% identical to the amino acid sequences selected from the group consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 24, SEQ ID NO. 26, SEQ ID NO. 28, SEQ ID NO. 30, SEQ ID NO. 32, SEQ ID NO. 34, SEQ ID NO. 36, SEQ ID NO. 38, SEQ ID NO. 40, SEQ ID NO. 42, SEQ ID NO. 44, SEQ ID NO. 46, SEQ ID NO. 48, SEQ ID NO. 50, SEQ ID NO. 52, SEQ ID NO. 54, SEQ ID NO. 56, SEQ ID NO. 58, SEQ ID NO. 60, and combinations thereof. Preferably, the fully human antibody has both a heavy chain and a light chain wherein the antibody has a heavy chain/light chain variable domain sequence selected from the group consisting of SEQ ID NO. 1/SEQ ID NO. 2 (called A01 herein), SEQ ID NO. 3/SEQ ID NO. 4 (called A02 herein), SEQ ID NO. 5/SEQ ID NO. 6 (called A04 herein), SEQ ID NO. 7/SEQ ID NO. 8 (called A08 herein), SEQ ID NO. 9/SEQ ID NO. 10 (called A11 herein), SEQ ID NO. 11/SEQ ID NO. 12 (called A12 herein), SEQ ID NO. 13/SEQ ID NO. 14 (called B01 herein), SEQ ID NO. 15/SEQ ID NO. 16 (called B03 herein), SEQ ID NO. 17/SEQ ID NO. 18 (called B04 herein), SEQ ID NO. 19/SEQ ID NO. 20 (called B05 herein), SEQ ID NO. 21/SEQ ID NO. 22 (called B08 herein), SEQ ID NO. 23/SEQ ID NO. 24 (called B10 herein), SEQ ID NO. 25/SEQ ID NO.26 (called B11 herein), SEQ ID NO. 27/SEQ ID NO. 28 (called C03 herein), SEQ ID NO. 29/SEQ ID NO. 30 (called C07 herein), SEQ ID NO. 31/SEQ ID NO. 32 (called C10 herein), SEQ ID NO. 33/SEQ ID NO. 34 (called C12 herein), SEQ ID NO. 35/SEQ ID NO. 36 (called D01 herein), SEQ ID NO. 37/SEQ ID NO. 38 (called D03 herein), SEQ ID NO. 39/SEQ ID NO. 40 (called D04 herein), SEQ ID NO. 41/SEQ ID NO. 42 (called D07 herein), SEQ ID NO. 43/SEQ ID NO. 44 (called D08 herein), SEQ ID NO. 45/SEQ ID NO. 46 (called D10 herein), SEQ ID NO. 47/SEQ ID NO. 48 (called D11 herein), SEQ ID NO. 49/SEQ ID NO. 50 (called E04 herein), SEQ ID NO. 51/SEQ ID NO. 52 (called E05 herein), SEQ ID NO. 53/SEQ ID NO. 54 (called E08 herein), SEQ ID NO. 55/SEQ ID NO. 56 (called F10 herein), SEQ ID NO. 57/SEQ ID NO. 58 (called G01 herein), SEQ ID NO. 59/SEQ ID NO. 60 (called H06 herein), and combinations thereof.

The present disclosure provides a fully human antibody Fab fragment, having a variable domain region from a heavy chain and a variable domain region from a light chain, wherein the heavy chain variable domain sequence that is at least 95% identical to the amino acid sequences selected from the group consisting of SEQ ID NO. 1, SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 25, SEQ ID NO. 27, SEQ ID NO. 29, SEQ ID NO. 31, SEQ ID NO. 33, SEQ ID NO. 35, SEQ ID NO. 37, SEQ ID NO. 39, SEQ ID NO. 41, SEQ ID NO. 43, SEQ ID NO. 45, SEQ ID NO. 47, SEQ ID NO.49, SEQ ID NO. 51, SEQ ID NO. 53, SEQ ID NO. 55, SEQ ID NO. 57, SEQ ID NO. 59, and combinations thereof, and that has a light chain variable domain sequence that is at least 95% identical to the amino acid sequences selected from the group consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 24, SEQ ID NO. 26, SEQ ID NO. 28, SEQ ID NO. 30, SEQ ID NO. 32, SEQ ID NO. 34, SEQ ID NO. 36, SEQ ID NO. 38, SEQ ID NO. 40, SEQ ID NO. 42, SEQ ID NO. 44, SEQ ID NO. 46, SEQ ID NO. 48, SEQ ID NO. 50, SEQ ID NO. 52, SEQ ID NO. 54, SEQ ID NO. 56, SEQ ID NO. 58, SEQ ID NO. 60, and combinations thereof. Preferably, the fully human antibody Fab fragment has both a heavy chain variable domain region and a light chain variable domain region wherein the antibody has a heavy chain/light chain variable domain sequence selected from the group consisting of SEQ ID NO. 1/SEQ ID NO. 2, SEQ ID NO. 3/SEQ ID NO. 4, SEQ ID NO. 5/SEQ ID NO. 6, SEQ ID NO. 7/SEQ ID NO. 8, SEQ ID NO. 9/SEQ ID NO. 10, SEQ ID NO. 11/SEQ ID NO. 12, SEQ ID NO. 13/SEQ ID NO. 14, SEQ ID NO. 15/SEQ ID NO. 16, SEQ ID NO. 17/SEQ ID NO. 18, SEQ ID NO. 19/SEQ ID NO. 20, SEQ ID NO. 21/SEQ ID NO. 22, SEQ ID NO. 23/SEQ ID NO. 24, SEQ ID NO. 25/SEQ ID NO. 26, SEQ ID NO. 27/SEQ ID NO. 28, SEQ ID NO. 29/SEQ ID NO. 30, SEQ ID NO. 31/SEQ ID NO. 32, SEQ ID NO. 33/SEQ ID NO. 34, SEQ ID NO. 35/SEQ ID NO. 36, SEQ ID NO. 37/SEQ ID NO. 38, SEQ ID NO. 39/SEQ ID NO. 40, SEQ ID NO. 41/SEQ ID NO. 42, SEQ ID NO. 43/SEQ ID NO. 44, SEQ ID NO. 45/SEQ ID NO. 46, SEQ ID NO. 47/SEQ ID NO. 48, SEQ ID NO. 49/SEQ ID NO. 50, SEQ ID NO. 51/SEQ ID NO. 52, SEQ ID NO. 53/SEQ ID NO. 54, SEQ ID NO. 55/SEQ ID NO. 56, SEQ ID NO. 57/SEQ ID NO. 58, SEQ ID NO. 59/SEQ ID NO. 60, and combinations thereof.

The present disclosure provides a single chain human antibody, having a variable domain region from a heavy chain and a variable domain region from a light chain and a peptide linker connection the heavy chain and light chain variable domain regions, wherein the heavy chain variable domain sequence that is at least 95% identical to the amino acid sequences selected from the group consisting of SEQ ID NO. 1, SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 25, SEQ ID NO. 27, SEQ ID NO. 29, SEQ ID NO. 31, SEQ ID NO. 33, SEQ ID NO. 35, SEQ ID NO. 37, SEQ ID NO. 39, SEQ ID NO. 41, SEQ ID NO. 43, SEQ ID NO. 45, SEQ ID NO. 47, SEQ ID NO.49, SEQ ID NO. 51, SEQ ID NO. 53, SEQ ID NO. 55, SEQ ID NO. 57, SEQ ID NO. 59, and combinations thereof, and that has a light chain variable domain sequence that is at least 95% identical to the amino acid sequences selected from the group consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 24, SEQ ID NO. 26, SEQ ID NO. 28, SEQ ID NO. 30, SEQ ID NO. 32, SEQ ID NO. 34, SEQ ID NO. 36, SEQ ID NO. 38, SEQ ID NO. 40, SEQ ID NO. 42, SEQ ID NO. 44, SEQ ID NO. 46, SEQ ID NO. 48, SEQ ID NO. 50, SEQ ID NO. 52, SEQ ID NO. 54, SEQ ID NO. 56, SEQ ID NO. 58, SEQ ID NO. 60, and combinations thereof. Preferably, the fully human single chain antibody has both a heavy chain variable domain region and a light chain variable domain region, wherein the single chain fully human antibody has a heavy chain/light chain variable domain sequence selected from the group consisting of SEQ ID NO. 1/SEQ ID NO. 2, SEQ ID NO. 3/SEQ ID NO. 4, SEQ ID NO. 5/SEQ ID NO. 6, SEQ ID NO. 7/SEQ ID NO. 8, SEQ ID NO. 9/SEQ ID NO. 10, SEQ ID NO. 11/SEQ ID NO. 12, SEQ ID NO. 13/SEQ ID NO. 14, SEQ ID NO. 15/SEQ ID NO. 16, SEQ ID NO. 17/SEQ ID NO. 18, SEQ ID NO. 19/SEQ ID NO. 20, SEQ ID NO. 21/SEQ ID NO. 22, SEQ ID NO. 23/SEQ ID NO. 24, SEQ ID NO. 25/SEQ ID NO. 26, SEQ ID NO. 27/SEQ ID NO. 28, SEQ ID NO. 29/SEQ ID NO. 30, SEQ ID NO. 31/SEQ ID NO. 32, SEQ ID NO. 33/SEQ ID NO. 34, SEQ ID NO. 35/SEQ ID NO. 36, SEQ ID NO. 37/SEQ ID NO. 38, SEQ ID NO. 39/SEQ ID NO. 40, SEQ ID NO. 41/SEQ ID NO. 42, SEQ ID NO. 43/SEQ ID NO. 44, SEQ ID NO. 45/SEQ ID NO. 46, SEQ ID NO. 47/SEQ ID NO. 48, SEQ ID NO. 49/SEQ ID NO. 50, SEQ ID NO. 51/SEQ ID NO. 52, SEQ ID NO. 53/SEQ ID NO. 54, SEQ ID NO. 55/SEQ ID NO. 56, SEQ ID NO. 57/SEQ ID NO. 58, SEQ ID NO. 59/SEQ ID NO. 60, and combinations thereof.

The present disclosure further provides a method for treating a broad spectrum of mammalian cancers or inflammatory diseases or autoimmune diseases, comprising administering an effective amount of an anti-ErbB3 polypeptide, wherein the anti-ErbB3 polypeptide is selected from the group consisting of a fully human antibody of an IgG class that binds to an ErbB3 epitope with a binding affinity of at least $10^{-6}$M, a fully human antibody Fab fragment, having a variable domain region from a heavy chain and a variable domain region from a light chain, a single chain human antibody, having a variable domain region from a heavy chain and a variable domain region from a light chain and a peptide linker connection the heavy chain and light chain variable domain regions, and combinations thereof;

wherein the fully human antibody has a heavy chain variable domain sequence that is at least 95% identical to the amino acid sequences selected from the group consisting of SEQ ID NO. 1, SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 25, SEQ ID NO. 27, SEQ ID NO. 29, SEQ ID NO. 31, SEQ ID NO. 33, SEQ ID NO. 35, SEQ ID NO. 37, SEQ ID NO. 39, SEQ ID NO. 41, SEQ ID NO. 43, SEQ ID NO. 45, SEQ ID NO. 47, SEQ ID NO.49, SEQ ID NO. 51, SEQ ID NO. 53, SEQ ID NO. 55, SEQ ID NO. 57, SEQ ID NO. 59, and combinations thereof, and that has a light chain variable domain sequence that is at least 95% identical to the amino acid sequences selected from the group consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 24, SEQ ID NO. 26, SEQ ID NO. 28, SEQ ID NO. 30, SEQ ID NO. 32, SEQ ID NO. 34, SEQ ID NO. 36, SEQ ID NO. 38, SEQ ID NO. 40, SEQ ID NO. 42, SEQ ID NO. 44, SEQ ID NO. 46, SEQ ID NO. 48, SEQ ID NO. 50, SEQ ID NO. 52, SEQ ID NO. 54, SEQ ID NO. 56, SEQ ID NO. 58, SEQ ID NO. 60, and combinations thereof;

wherein the fully human antibody Fab fragment has the heavy chain variable domain sequence that is at least 95% identical to the amino acid sequences selected from the group consisting of SEQ ID NO. 1, SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 25, SEQ ID NO. 27, SEQ ID NO. 29, SEQ ID NO. 31, SEQ ID NO. 33, SEQ ID NO. 35, SEQ ID NO. 37, SEQ ID NO. 39, SEQ ID NO. 41, SEQ ID NO. 43, SEQ ID NO. 45, SEQ ID NO. 47, SEQ ID NO.49, SEQ ID NO. 51, SEQ ID NO. 53, SEQ ID NO. 55, SEQ ID NO. 57, SEQ ID NO. 59, and combinations thereof, and that has the light chain variable domain sequence that is at least 95% identical to the amino acid sequences selected from the group consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 24, SEQ ID NO. 26, SEQ ID NO. 28, SEQ ID NO. 30, SEQ ID NO. 32, SEQ ID NO. 34, SEQ ID NO. 36, SEQ ID NO. 38, SEQ ID NO. 40, SEQ ID NO. 42, SEQ ID NO. 44, SEQ ID NO. 46, SEQ ID NO. 48, SEQ ID NO. 50, SEQ ID NO. 52, SEQ ID NO. 54, SEQ ID NO. 56, SEQ ID NO. 58, SEQ ID NO. 60, and combinations thereof; and wherein the single chain human antibody has the heavy chain variable domain sequence that is at least 95% identical to the amino acid sequences selected from the group consisting of SEQ ID NO. 1, SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 25, SEQ ID NO. 27, SEQ ID NO. 29, SEQ ID NO. 31, SEQ ID NO. 33, SEQ ID NO. 35, SEQ ID NO. 37, SEQ ID NO. 39, SEQ ID NO. 41, SEQ ID NO. 43, SEQ ID NO. 45, SEQ ID NO. 47, SEQ ID NO.49, SEQ ID NO. 51, SEQ ID NO. 53, SEQ ID NO. 55, SEQ ID NO. 57, SEQ ID NO. 59, and combinations thereof, and that has the light chain variable domain sequence that is at least 95% identical to the amino acid sequences selected from the group consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 24, SEQ ID NO. 26, SEQ ID NO. 28, SEQ ID NO. 30, SEQ ID NO. 32, SEQ ID NO. 34, SEQ ID NO. 36, SEQ ID NO. 38, SEQ ID NO. 40, SEQ ID NO. 42, SEQ ID NO. 44, SEQ ID NO. 46, SEQ ID NO. 48, SEQ ID NO. 50, SEQ ID NO. 52, SEQ ID NO. 54, SEQ ID NO. 56, SEQ ID NO. 58, SEQ ID NO. 60, and combinations thereof.

Preferably, the fully human antibody has both a heavy chain and a light chain wherein the antibody has a heavy chain/light chain variable domain sequence selected from the group consisting of SEQ ID NO. 1/SEQ ID NO. 2, SEQ ID NO. 3/SEQ ID NO. 4, SEQ ID NO. 5/SEQ ID NO. 6, SEQ ID NO. 7/SEQ ID NO. 8, SEQ ID NO. 9/SEQ ID NO. 10, SEQ ID NO. 11/SEQ ID NO. 12, SEQ ID NO. 13/SEQ ID NO. 14, SEQ ID NO. 15/SEQ ID NO. 16, SEQ ID NO. 17/SEQ ID NO. 18, SEQ ID NO. 19/SEQ ID NO. 20, SEQ ID NO. 21/SEQ ID NO. 22, SEQ ID NO. 23/SEQ ID NO. 24, SEQ ID NO. 25/SEQ ID NO. 26, SEQ ID NO. 27/SEQ ID NO. 28, SEQ ID NO. 29/SEQ ID NO. 30, SEQ ID NO. 31/SEQ ID NO. 32, SEQ ID NO. 33/SEQ ID NO. 34, SEQ ID NO. 35/SEQ ID NO. 36, SEQ ID NO. 37/SEQ ID NO. 38, SEQ ID NO. 39/SEQ ID NO. 40, SEQ ID NO. 41/SEQ ID NO. 42, SEQ ID NO. 43/SEQ ID NO. 44, SEQ ID NO. 45/SEQ ID NO. 46, SEQ ID NO. 47/SEQ ID NO. 48, SEQ ID NO. 49/SEQ ID NO. 50, SEQ ID NO. 51/SEQ ID NO. 52, SEQ ID NO. 53/SEQ ID NO. 54, SEQ ID NO. 55/SEQ ID NO. 56, SEQ ID NO. 57/SEQ ID NO. 58, SEQ ID NO. 59/SEQ ID NO. 60, and combinations thereof. Preferably, the fully human antibody Fab fragment has both a heavy chain variable domain region and a light chain variable domain region wherein the antibody has a heavy chain/light chain variable domain sequence selected from the group consisting of SEQ ID NO. 1/SEQ ID NO. 2, SEQ ID NO. 3/SEQ ID NO. 4, SEQ ID NO. 5/SEQ ID NO. 6, SEQ ID NO. 7/SEQ ID NO. 8, SEQ ID NO. 9/SEQ ID NO. 10, SEQ ID NO. 11/SEQ ID NO. 12, SEQ ID NO. 13/SEQ ID NO. 14, SEQ ID NO. 15/SEQ ID NO. 16, SEQ ID NO. 17/SEQ ID NO. 18, SEQ ID NO. 19/SEQ ID NO. 20, SEQ ID NO. 21/SEQ ID NO. 22, SEQ ID NO. 23/SEQ ID NO. 24, SEQ ID NO. 25/SEQ ID NO. 26, SEQ ID NO. 27/SEQ ID NO. 28, SEQ ID NO. 29/SEQ ID NO. 30, SEQ ID NO. 31/SEQ ID NO. 32, SEQ ID NO. 33/SEQ ID NO. 34, SEQ ID NO. 35/SEQ ID NO. 36, SEQ ID NO. 37/SEQ ID NO. 38, SEQ ID NO. 39/SEQ ID NO. 40, SEQ ID NO. 41/SEQ ID NO. 42, SEQ ID NO. 43/SEQ ID NO. 44, SEQ ID NO. 45/SEQ ID NO. 46, SEQ ID NO. 47/SEQ ID NO. 48, SEQ ID NO. 49/SEQ ID NO. 50, SEQ ID NO. 51/SEQ ID NO. 52, SEQ ID NO. 53/SEQ ID NO. 54, SEQ ID NO. 55/SEQ ID NO. 56, SEQ ID NO. 57/SEQ ID NO. 58, SEQ ID NO. 59/SEQ ID NO. 60, and combinations thereof. Preferably, the fully human single chain antibody has both a heavy chain variable domain region and a light chain variable domain region, wherein the single chain fully human antibody has a heavy chain/light chain variable domain sequence selected from the group consisting of SEQ ID NO. 1/SEQ ID NO. 2, SEQ ID NO. 3/SEQ ID NO. 4, SEQ ID NO. 5/SEQ ID NO. 6, SEQ ID NO. 7/SEQ ID NO. 8, SEQ ID NO. 9/SEQ ID NO. 10, SEQ ID NO. 11/SEQ ID NO. 12, SEQ ID NO. 13/SEQ ID NO. 14, SEQ ID NO. 15/SEQ ID NO. 16, SEQ ID NO. 17/SEQ ID NO. 18, SEQ ID NO. 19/SEQ ID NO. 20, SEQ ID NO. 21/SEQ ID NO. 22, SEQ ID NO. 23/SEQ ID NO. 24, SEQ ID NO. 25/SEQ ID NO. 26, SEQ ID NO. 27/SEQ ID NO. 28, SEQ ID NO. 29/SEQ ID NO. 30, SEQ ID NO. 31/SEQ ID NO. 32, SEQ ID NO. 33/SEQ ID NO. 34, SEQ ID NO. 35/SEQ ID NO. 36, SEQ ID NO. 37/SEQ ID NO. 38, SEQ ID NO. 39/SEQ ID NO. 40, SEQ ID NO. 41/SEQ ID NO. 42, SEQ ID NO. 43/SEQ ID NO. 44, SEQ ID NO. 45/SEQ ID NO. 46, SEQ ID NO. 47/SEQ ID NO. 48, SEQ ID NO. 49/SEQ ID NO. 50, SEQ ID NO. 51/SEQ ID NO. 52, SEQ ID NO. 53/SEQ ID NO. 54, SEQ ID NO. 55/SEQ ID NO. 56, SEQ ID NO. 57/SEQ ID NO. 58, SEQ ID NO. 59/SEQ ID NO. 60, and combinations thereof.

Preferably, the broad spectrum of mammalian cancers to be treated the cancer is an ErbB3-positive cancer. Preferably, the broad spectrum of mammalian cancers to be treated is selected from the group consisting of carcinomas, prostate cancer, non-small cell lung cancer, breast cancer, endometrial cancer, ovarian cancer, gastric cancers, head and neck cancers, and colon cancer.

An "antigen binding protein" is a protein comprising a portion that binds to an antigen and, optionally, a scaffold or framework portion that allows the antigen binding portion to adopt a conformation that promotes binding of the antigen binding protein to the antigen. Examples of antigen binding proteins include antibodies, antibody fragments (e.g., an antigen binding portion of an antibody), antibody derivatives, and antibody analogs. The antigen binding protein can comprise, for example, an alternative protein scaffold or artificial scaffold with grafted CDRs or CDR derivatives. Such scaffolds include, but are not limited to, antibody-derived scaffolds comprising mutations introduced to, for example, stabilize the three-dimensional structure of the antigen binding protein as well as wholly synthetic scaffolds comprising, for example, a biocompatible polymer. See, for example, Korndorfer et al., 2003, *Proteins: Structure, Function, and Bioinformatics*, Volume 53, Issue 1:121-129; Roque et al., 2004, *Biotechnol. Prog.* 20:639-654. In addition, peptide antibody mimetics ("PAMs") can be used, as well as scaffolds based on antibody mimetics utilizing fibronection components as a scaffold.

An antigen binding protein can have, for example, the structure of a naturally occurring immunoglobulin. An "immunoglobulin" is a tetrameric molecule. In a naturally occurring immunoglobulin, each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. Human light chains are classified as kappa or lambda light chains. Heavy chains are classified as mu, delta, gamma, alpha, or epsilon, and define the antibody's isotype as IgM, IgD, IgG, IgA, and IgE, respectively. Within light and heavy chains, the variable and constant regions are joined by a "J" region of about 12 or more amino acids, with the heavy chain also including a "D" region of about 10 more amino acids. See generally, Fundamental Immunology Ch. 7 (Paul, W., ed., 2nd ed. Raven Press, N.Y. (1989)) (incorporated by reference in its entirety for all purposes). The variable regions of each light/heavy chain pair form the antibody binding site such that an intact immunoglobulin has two binding sites.

The variable regions of naturally occurring immunoglobulin chains exhibit the same general structure of relatively conserved framework regions (FR) joined by three hypervariable regions, also called complementarity determining regions or CDRs. From N-terminus to C-terminus, both light and heavy chains comprise the domains FR1, CDR1, FR2, CDR2, FR3, CDR3 and FR4. The assignment of amino acids to each domain is in accordance with the definitions of Kabat et al. in Sequences of Proteins of Immunological Interest, $5^{th}$ Ed., US Dept. of Health and Human Services, PHS, NIH, NIH Publication no. 91-3242, 1991. Other numbering systems for the amino acids in immunoglobulin chains include IMGT.RTM. (international ImMunoGeneTics information system; Lefranc et al, *Dev. Comp. Immunol.* 29:185-203; 2005) and AHo (Honegger and Pluckthun, *J. Mol. Biol.* 309 (3):657-670; 2001).

Antibodies can be obtained from sources such as serum or plasma that contain immunoglobulins having varied antigenic specificity. If such antibodies are subjected to affinity purification, they can be enriched for a particular antigenic specificity. Such enriched preparations of antibodies usually are made of less than about 10% antibody having specific binding activity for the particular antigen. Subjecting these preparations to several rounds of affinity purification can increase the proportion of antibody having specific binding activity for the antigen. Antibodies prepared in this manner are often referred to as "monospecific." Monospecfic antibody preparations can be made up of about 10%, 20%, 30%, 40%, 50%, 60%, 70%, 75%, 80%, 85%, 90%, 95%, 97%, 99%, or 99.9% antibody having specific binding activity for the particular antigen.

An "antibody" refers to an intact immunoglobulin or to an antigen binding portion thereof that competes with the intact antibody for specific binding, unless otherwise specified. Antigen binding portions may be produced by recombinant DNA techniques or by enzymatic or chemical cleavage of intact antibodies. Antigen binding portions include, inter alia, Fab, Fab', F(ab')$_2$, Fv, domain antibodies (dAbs), and complementarity determining region (CDR) fragments, single-chain antibodies (scFv), chimeric antibodies, diabodies, triabodies, tetrabodies, and polypeptides that contain at least a portion of an immunoglobulin that is sufficient to confer specific antigen binding to the polypeptide.

A Fab fragment is a monovalent fragment having the $V_L$, $V_H$, $C_L$ and $C_{H1}$ domains; a F(ab')$_2$ fragment is a bivalent fragment having two Fab fragments linked by a disulfide bridge at the hinge region; a Fd fragment has the $V_H$ and $C_{H1}$ domains; an Fv fragment has the $V_L$ and $V_H$ domains of a single arm of an antibody; and a dAb fragment has a $V_H$ domain, a $V_L$ domain, or an antigen-binding fragment of a $V_H$ or VL domain (U.S. Pat. Nos. 6,846,634; 6,696,245, US Patent Applications 2002/02512; 2004/0202995; 2004/0038291; 2004/0009507; 2003/0039958, and Ward et al., *Nature* 341:544-546, 1989).

A single-chain antibody (scFv) is an antibody in which a $V_L$ and a $V_H$ region are joined via a linker (e.g., a synthetic sequence of amino acid residues) to form a continuous protein chain wherein the linker is long enough to allow the protein chain to fold back on itself and form a monovalent antigen binding site (Bird et al., 1988, *Science* 242:423-26 and Huston et al., 1988, *Proc. Natl. Acad. Sci. USA* 85:5879-83). Diabodies are bivalent antibodies comprising two polypeptide chains, wherein each polypeptide chain comprises $V_H$ and $V_L$ domains joined by a linker that is too short to allow for pairing between two domains on the same chain, thus allowing each domain to pair with a complementary domain on another polypeptide chain (Holliger et al., 1993, *Proc. Natl. Acad. Sci. USA* 90:6444-48, and Poljak et al., 1994, *Structure* 2:1121-23). If the two polypeptide chains of a diabody are identical, then a diabody resulting from their pairing will have two identical antigen binding sites. Polypeptide chains having different sequences can be used to make a diabody with two different antigen binding sites. Similarly, tribodies and tetrabodies are antibodies comprising three and four polypeptide chains, respectively, and forming three and four antigen binding sites, respectively, which can be the same or different.

Complementarity determining regions (CDRs) and framework regions (FR) of a given antibody may be identified using the system described by Kabat et al. supra; Lefranc et al., supra and/or Honegger and Pluckthun, supra. One or more CDRs may be incorporated into a molecule either covalently or noncovalently to make it an antigen binding protein. An antigen binding protein may incorporate the CDR(s) as part of a larger polypeptide chain, may covalently link the CDR(s) to another polypeptide chain, or may incorporate the CDR(s) noncovalently. The CDRs permit the antigen binding protein to specifically bind to a particular antigen of interest.

An antigen binding protein may have one or more binding sites. If there is more than one binding site, the binding sites may be identical to one another or may be different. For example, a naturally occurring human immunoglobulin typically has two identical binding sites, while a "bispecific" or "bifunctional" antibody has two different binding sites.

The term "human antibody" includes all antibodies that have one or more variable and constant regions derived from human immunoglobulin sequences. In one embodiment, all of the variable and constant domains are derived from human immunoglobulin sequences (a fully human antibody). These antibodies may be prepared in a variety of ways, examples of which are described below, including through the immunization with an antigen of interest of a mouse that is genetically modified to express antibodies derived from human heavy and/or light chain-encoding genes.

A humanized antibody has a sequence that differs from the sequence of an antibody derived from a non-human species by one or more amino acid substitutions, deletions, and/or additions, such that the humanized antibody is less likely to induce an immune response, and/or induces a less severe immune response, as compared to the non-human species antibody, when it is administered to a human subject. In one embodiment, certain amino acids in the framework and constant domains of the heavy and/or light chains of the non-human species antibody are mutated to produce the humanized antibody. In another embodiment, the constant domain(s) from a human antibody are fused to the variable domain(s) of a non-human species. In another embodiment, one or more amino acid residues in one or more CDR sequences of a non-human antibody are changed to reduce the likely immunogenicity of the non-human antibody when it is administered to a human subject, wherein the changed amino acid residues either are not critical for immunospecific binding of the antibody to its antigen, or the changes to the amino acid sequence that are made are conservative changes, such that the binding of the humanized antibody to the antigen is not significantly worse than the binding of the non-human antibody to the antigen. Examples of how to make humanized antibodies may be found in U.S. Pat. Nos. 6,054,297, 5,886,152 and 5,877,293.

The term "chimeric antibody" refers to an antibody that contains one or more regions from one antibody and one or more regions from one or more other antibodies. In one embodiment, one or more of the CDRs are derived from a human anti-ErbB3 antibody. In another embodiment, all of the CDRs are derived from a human anti-ErbB3 antibody. In another embodiment, the CDRs from more than one human anti-ErbB3 antibodies are mixed and matched in a chimeric antibody. For instance, a chimeric antibody may comprise a CDR1 from the light chain of a first human anti-PAR-2 antibody, a CDR2 and a CDR3 from the light chain of a second human anti-ErbB3 antibody, and the CDRs from the heavy chain from a third anti-ErbB3 antibody. Other combinations are possible.

Further, the framework regions may be derived from one of the same anti-ErbB3 antibodies, from one or more different antibodies, such as a human antibody, or from a humanized antibody. In one example of a chimeric antibody, a portion of the heavy and/or light chain is identical with, homologous to, or derived from an antibody from a particular species or belonging to a particular antibody class or subclass, while the remainder of the chain(s) is/are identical with, homologous to, or derived from an antibody (-ies) from another species or belonging to another antibody class or subclass. Also included are fragments of such antibodies that exhibit the desired biological activity (i.e., the ability to specifically bind ErbB3).

A "neutralizing antibody" or an "inhibitory antibody" is an antibody that inhibits the activation of ErbB3 when an excess of the anti-ErbB3 antibody reduces the amount of activation by at least about 20% using an assay such as those described herein in the Examples. In various embodiments, the antigen binding protein reduces the amount of amount of activation of ErbB3 by at least 30%, 40%, 50%, 60%, 70%, 75%, 80%, 85%, 90%, 95%, 97%, 99%, and 99.9%.

Fragments or analogs of antibodies can be readily prepared by those of ordinary skill in the art following the teachings of this specification and using techniques known in the art. Preferred amino- and carboxy-termini of fragments or analogs occur near boundaries of functional domains. Structural and functional domains can be identified by comparison of the nucleotide and/or amino acid sequence data to public or proprietary sequence databases. Computerized comparison methods can be used to identify sequence motifs or predicted protein conformation domains that occur in other proteins of known structure and/or function. Methods to identify protein sequences that fold into a known three-dimensional structure are known. See, Bowie et al., 1991, *Science* 253:164.

A "CDR grafted antibody" is an antibody comprising one or more CDRs derived from an antibody of a particular species or isotype and the framework of another antibody of the same or different species or isotype.

A "multi-specific antibody" is an antibody that recognizes more than one epitope on one or more antigens. A subclass of this type of antibody is a "bi-specific antibody" which recognizes two distinct epitopes on the same or different antigens.

An antigen binding protein "specifically binds" to an antigen (e.g., human ErbB3) if it binds to the antigen with a dissociation constant of 1 nanomolar or less.

An "antigen binding domain," "antigen binding region," or "antigen binding site" is a portion of an antigen binding protein that contains amino acid residues (or other moieties) that interact with an antigen and contribute to the antigen binding protein's specificity and affinity for the antigen. For an antibody that specifically binds to its antigen, this will include at least part of at least one of its CDR domains.

An "epitope" is the portion of a molecule that is bound by an antigen binding protein (e.g., by an antibody). An epitope can comprise non-contiguous portions of the molecule (e.g., in a polypeptide, amino acid residues that are not contiguous in the polypeptide's primary sequence but that, in the context of the polypeptide's tertiary and quaternary structure, are near enough to each other to be bound by an antigen binding protein).

The "percent identity" of two polynucleotide or two polypeptide sequences is determined by comparing the sequences using the GAP computer program (a part of the GCG Wisconsin Package, version 10.3 (Accelrys, San Diego, Calif.)) using its default parameters.

The terms "polynucleotide," "oligonucleotide" and "nucleic acid" are used interchangeably throughout and include DNA molecules (e.g., cDNA or genomic DNA), RNA molecules (e.g., mRNA), analogs of the DNA or RNA generated using nucleotide analogs (e.g., peptide nucleic acids and non-naturally occurring nucleotide analogs), and hybrids thereof. The nucleic acid molecule can be single-stranded or double-stranded. In one embodiment, the nucleic acid molecules of the invention comprise a contiguous open reading frame encoding an antibody, or a fragment, derivative, mutein, or variant thereof.

Two single-stranded polynucleotides are "the complement" of each other if their sequences can be aligned in an anti-parallel orientation such that every nucleotide in one polynucleotide is opposite its complementary nucleotide in the other polynucleotide, without the introduction of gaps, and without unpaired nucleotides at the 5' or the 3' end of either sequence. A polynucleotide is "complementary" to another polynucleotide if the two polynucleotides can hybridize to one another under moderately stringent conditions. Thus, a polynucleotide can be complementary to another polynucleotide without being its complement.

A "vector" is a nucleic acid that can be used to introduce another nucleic acid linked to it into a cell. One type of vector is a "plasmid," which refers to a linear or circular double stranded DNA molecule into which additional nucleic acid segments can be ligated. Another type of vector is a viral vector (e.g., replication defective retroviruses, adenoviruses and adeno-associated viruses), wherein additional DNA segments can be introduced into the viral genome. Certain vectors are capable of autonomous replication in a host cell into which they are introduced (e.g., bacterial vectors comprising a bacterial origin of replication and episomal mammalian vectors). Other vectors (e.g., non-episomal mammalian vectors) are integrated into the genome of a host cell upon introduction into the host cell, and thereby are replicated along with the host genome. An "expression vector" is a type of vector that can direct the expression of a chosen polynucleotide.

A nucleotide sequence is "operably linked" to a regulatory sequence if the regulatory sequence affects the expression (e.g., the level, timing, or location of expression) of the nucleotide sequence. A "regulatory sequence" is a nucleic acid that affects the expression (e.g., the level, timing, or location of expression) of a nucleic acid to which it is operably linked. The regulatory sequence can, for example, exert its effects directly on the regulated nucleic acid, or through the action of one or more other molecules (e.g., polypeptides that bind to the regulatory sequence and/or the nucleic acid). Examples of regulatory sequences include promoters, enhancers and other expression control elements (e.g., polyadenylation signals). Further examples of regulatory sequences are described in, for example, Goeddel, 1990, Gene Expression Technology: *Methods in Enzymology* 185, Academic Press, San Diego, Calif. and Baron et al., 1995, *Nucleic Acids Res.* 23:3605-06.

A "host cell" is a cell that can be used to express a nucleic acid, e.g., a nucleic acid of the invention. A host cell can be a prokaryote, for example, *E. coli*, or it can be a eukaryote, for example, a single-celled eukaryote (e.g., a yeast or other fungus), a plant cell (e.g., a tobacco or tomato plant cell), an animal cell (e.g., a human cell, a monkey cell, a hamster cell, a rat cell, a mouse cell, or an insect cell) or a hybridoma. Examples of host cells include the COS-7 line of monkey kidney cells (ATCC CRL 1651) (see Gluzman et al., 1981, *Cell* 23:175), L cells, C127 cells, 3T3 cells (ATCC CCL 163), Chinese hamster ovary (CHO) cells or their derivatives such as Veggie CHO and related cell lines which grow in serum-free media (see Rasmussen et al., 1998, *Cytotechnology* 28:31) or CHO strain DX-B11, which is deficient in DHFR (see Urlaub et al., 1980, *Proc. Natl. Acad. Sci. USA* 77:4216-20), HeLa cells, BHK (ATCC CRL 10) cell lines, the CV1/EBNA cell line derived from the African green monkey kidney cell line CV1 (ATCC CCL 70) (see McMahan et al., 1991, *EMBO J.* 10:2821), human embryonic kidney cells such as 293,293 EBNA or MSR 293, human epidermal A431 cells, human Colo205 cells, other transformed primate cell lines, normal diploid cells, cell strains derived from in vitro culture of primary tissue, primary explants, HL-60, U937, HaK or Jurkat cells. Typically, a host cell is a cultured cell that can be transformed or transfected with a polypeptide-encoding nucleic acid, which can then be expressed in the host cell. The phrase "recombinant host cell" can be used to denote a host cell that has been transformed or transfected with a nucleic acid to be expressed. A host cell also can be a cell that comprises the nucleic acid but does not express it at a desired level unless a regulatory sequence is introduced into the host cell such that it becomes operably linked with the nucleic acid. It is understood that the term host cell refers not only to the particular subject cell but also to the progeny or potential progeny of such a cell. Because certain modifications may occur in succeeding generations due to, e.g., mutation or environmental influence, such progeny may not, in fact, be identical to the parent cell, but are still included within the scope of the term as used herein.

Preferably, the mammalian cancer to be treated is selected from the group consisting of ovarian, colon, breast or hepatic carcinoma cell lines, myelomas, neuroblastic-derived CNS tumors, monocytic leukemias, B-cell derived leukemia's, T-cell derived leukemias, B-cell derived lymphomas, T-cell derived lymphomas, mast cell derived tumors, and combinations thereof.

Polypeptides of the present disclosure can be produced using any standard methods known in the art. In one example, the polypeptides are produced by recombinant DNA methods by inserting a nucleic acid sequence (e.g., a cDNA) encoding the polypeptide into a recombinant expression vector and expressing the DNA sequence under conditions promoting expression.

Nucleic acids encoding any of the various polypeptides disclosed herein may be synthesized chemically. Codon usage may be selected so as to improve expression in a cell. Such codon usage will depend on the cell type selected. Specialized codon usage patterns have been developed for *E. coli* and other bacteria, as well as mammalian cells, plant cells, yeast cells and insect cells. See for example: Mayfield et al., *Proc. Natl. Acad. Sci. USA.* 2003 100(2):438-42; Sinclair et al. *Protein Expr. Purif.* 2002 (1):96-105; Connell N D. *Curr. Opin. Biotechnol.* 2001 12(5):446-9; Makrides et al. *Microbiol. Rev.* 1996 60(3):512-38; and Sharp et al. *Yeast.* 1991 7(7):657-78.

General techniques for nucleic acid manipulation are described for example in Sambrook et al., *Molecular Cloning: A Laboratory Manual*, Vols. 1-3, Cold Spring Harbor Laboratory Press, 2 ed., 1989, or F. Ausubel et al., *Current Protocols in Molecular Biology* (Green Publishing and Wiley-Interscience: New York, 1987) and periodic updates, herein incorporated by reference. The DNA encoding the polypeptide is operably linked to suitable transcriptional or translational regulatory elements derived from mammalian, viral, or insect genes. Such regulatory elements include a transcriptional promoter, an optional operator sequence to control transcription, a sequence encoding suitable mRNA ribosomal binding sites, and sequences that control the termination of transcription and translation. The ability to replicate in a host, usually conferred by an origin of replication, and a selection gene to facilitate recognition of transformants is additionally incorporated.

The recombinant DNA can also include any type of protein tag sequence that may be useful for purifying the protein. Examples of protein tags include but are not limited to a histidine tag, a FLAG tag, a myc tag, an HA tag, or a GST tag. Appropriate cloning and expression vectors for use with bacterial, fungal, yeast, and mammalian cellular hosts can be found in *Cloning Vectors: A Laboratory Manual*, (Elsevier, N.Y., 1985).

The expression construct is introduced into the host cell using a method appropriate to the host cell. A variety of methods for introducing nucleic acids into host cells are known in the art, including, but not limited to, electroporation; transfection employing calcium chloride, rubidium chloride, calcium phosphate, DEAE-dextran, or other substances; microprojectile bombardment; lipofection; and infection (where the vector is an infectious agent). Suitable host cells include prokaryotes, yeast, mammalian cells, or bacterial cells.

Suitable bacteria include gram negative or gram positive organisms, for example, *E. coli* or *Bacillus* spp. Yeast, preferably from the *Saccharomyces* species, such as *S. cerevisiae*, may also be used for production of polypeptides. Various mammalian or insect cell culture systems can also be employed to express recombinant proteins. Baculovirus systems for production of heterologous proteins in insect cells are reviewed by Luckow and Summers, *(Bio/Technology,* 6:47, 1988). Examples of suitable mammalian host cell lines include endothelial cells, COS-7 monkey kidney cells, CV-1, L cells, C127, 3T3, Chinese hamster ovary (CHO), human embryonic kidney cells, HeLa, 293, 293T, and BHK cell lines. Purified polypeptides are prepared by culturing suitable host/vector systems to express the recombinant proteins. For many applications, the small size of many of the polypeptides disclosed herein would make expression in *E. coli* as the preferred method for expression. The protein is then purified from culture media or cell extracts.

Proteins disclosed herein can also be produced using cell-translation systems. For such purposes the nucleic acids encoding the polypeptide must be modified to allow in vitro transcription to produce mRNA and to allow cell-free translation of the mRNA in the particular cell-free system being utilized (eukaryotic such as a mammalian or yeast cell-free translation system or prokaryotic such as a bacterial cell-free translation system).

ErbB3-binding polypeptides can also be produced by chemical synthesis (e.g., by the methods described in Solid Phase Peptide Synthesis, 2nd ed., 1984, The Pierce Chemical Co., Rockford, Ill.). Modifications to the protein can also be produced by chemical synthesis.

The polypeptides of the present disclosure can be purified by isolation/purification methods for proteins generally known in the field of protein chemistry. Non-limiting examples include extraction, recrystallization, salting out (e.g., with ammonium sulfate or sodium sulfate), centrifugation, dialysis, ultrafiltration, adsorption chromatography, ion exchange chromatography, hydrophobic chromatography, normal phase chromatography, reversed-phase chromatography, gel filtration, gel permeation chromatography, affinity chromatography, electrophoresis, countercurrent distribution or any combinations of these. After purification, polypeptides may be exchanged into different buffers and/or concentrated by any of a variety of methods known to the art, including, but not limited to, filtration and dialysis.

The purified polypeptide is preferably at least 85% pure, more preferably at least 95% pure, and most preferably at least 98% pure. Regardless of the exact numerical value of the purity, the polypeptide is sufficiently pure for use as a pharmaceutical product.

Post-Translational Modifications of Polypeptides

In certain embodiments, the binding polypeptides of the invention may further comprise post-translational modifications. Exemplary post-translational protein modifications include phosphorylation, acetylation, methylation, ADP-ribosylation, ubiquitination, glycosylation, carbonylation, sumoylation, biotinylation or addition of a polypeptide side chain or of a hydrophobic group. As a result, the modified soluble polypeptides may contain non-amino acid elements, such as lipids, poly- or mono-saccharide, and phosphates. A preferred form of glycosylation is sialylation, which conjugates one or more sialic acid moieties to the polypeptide. Sialic acid moieties improve solubility and serum half-life while also reducing the possible immunogeneticity of the protein. See Raju et al. *Biochemistry.* 2001 31; 40(30):8868-76.

In one specific embodiment, modified forms of the subject soluble polypeptides comprise linking the subject soluble polypeptides to nonproteinaceous polymers. In one specific embodiment, the polymer is polyethylene glycol ("PEG"), polypropylene glycol, or polyoxyalkylenes, in the manner as set forth in U.S. Pat. No. 4,640,835; 4,496,689; 4,301,144; 4,670,417; 4,791,192 or 4,179,337. Examples of the modified polypeptide include PEGylated VK-B8.

PEG is a water soluble polymer that is commercially available or can be prepared by ring-opening polymerization of ethylene glycol according to methods well known in the art (Sandler and Karo, Polymer Synthesis, Academic Press, New York, Vol. 3, pages 138-161). The term "PEG" is used broadly to encompass any polyethylene glycol molecule, without regard to size or to modification at an end of the PEG, and can be represented by the formula: X—O(CH$_2$CH$_2$O)$_n$-1CH$_2$CH$_2$OH (1), where n is 20 to 2300 and X is H or a terminal modification, e.g., a C$_{1-4}$ alkyl. In one embodiment, the PEG of the invention terminates on one end with hydroxy or methoxy, i.e., X is H or CH$_3$ ("methoxy PEG"). A PEG can contain further chemical groups which are necessary for binding reactions; which results from the chemical synthesis of the molecule; or which is a spacer for optimal distance of parts of the molecule. In addition, such a PEG can consist of one or more PEG side-chains which are linked together. PEGs with more than one PEG chain are called multiarmed or branched PEGs. Branched PEGs can be prepared, for example, by the addition of polyethylene oxide to various polyols, including glycerol, pentaerythriol, and sorbitol. For example, a four-armed branched PEG can be prepared from pentaerythriol and ethylene oxide. Branched PEG are described in, for example, EP-A 0 473 084 and U.S. Pat. No. 5,932,462. One form of PEGs includes two PEG side-chains (PEG2) linked via the primary amino groups of a lysine (Monfardini et al., *Bioconjugate Chem.* 6 (1995) 62-69).

PEG conjugation to peptides or proteins generally involves the activation of PEG and coupling of the activated PEG-intermediates directly to target proteins/peptides or to a linker, which is subsequently activated and coupled to target proteins/peptides (see Abuchowski et al., *J. Biol. Chem.,* 252, 3571 (1977) and *J. Biol. Chem.,* 252, 3582 (1977), Zalipsky, et al., and Harris et. al., in: *Poly(ethylene glycol) Chemistry: Biotechnical and Biomedical Applications*; (J. M. Harris ed.) Plenum Press: New York, 1992; Chap. 21 and 22). It is noted that a binding polypeptide containing a PEG molecule is also known as a conjugated protein, whereas the protein lacking an attached PEG molecule can be referred to as unconjugated.

Conventional separation and purification techniques known in the art can be used to purify PEGylated binding polypeptide, such as size exclusion (e.g. gel filtration) and ion exchange chromatography. Products may also be separated using SDS-PAGE. Products that may be separated include mono-, di-, tri-poly- and un-pegylated binding polypeptide, as well as free PEG. The percentage of mono-PEG conjugates can be controlled by pooling broader fractions around the elution peak to increase the percentage of mono-PEG in the composition. About ninety percent mono-PEG conjugates represents a good balance of yield and activity. Compositions in which, for example, at least ninety-two percent or at least ninety-six percent of the conjugates are mono-PEG species may be desired. In an embodiment of this invention the percentage of mono-PEG conjugates is from ninety percent to ninety-six percent.

In one embodiment, PEGylated binding polypeptide of the invention contain one, two or more PEG moieties. In one embodiment, the PEG moiety(ies) are bound to an amino acid residue which is on the surface of the protein and/or away from the surface that contacts the target ligand. In one embodiment, the combined or total molecular mass of PEG in PEG-binding polypeptide is from about 3,000 Da to 60,000 Da, optionally from about 10,000 Da to 36,000 Da. In a one embodiment, the PEG in pegylated binding polypeptide is a substantially linear, straight-chain PEG.

The serum clearance rate of PEG-modified polypeptide may be decreased by about 10%, 20%, 30%, 40%, 50%, 60%, 70%, 80%, or even 90%, relative to the clearance rate of the unmodified binding polypeptide. The PEG-modified polypeptide may have a half-life (t$_{1/2}$) which is enhanced relative to the half-life of the unmodified protein. The half-life of PEG-binding polypeptide may be enhanced by at least 10%, 20%, 30%, 40%, 50%, 60%, 70%, 80%, 90%, 100%, 125%, 150%, 175%, 200%, 250%, 300%, 400% or 500%, or even by 1000% relative to the half-life of the unmodified binding polypeptide. In some embodiments, the protein half-life is determined in vitro, such as in a buffered saline solution or in serum. In other embodiments, the protein half-life is an in vivo half life, such as the half-life of the protein in the serum or other bodily fluid of an animal.

Therapeutic Formulations and Modes of Administration

The present disclosure features methods for treating conditions or preventing pre-conditions which respond to an inhibition of ErbB3 biological activity. Preferred examples are conditions that are characterized by inflammation or cellular hyperproliferation. Techniques and dosages for administration vary depending on the type of specific polypeptide and the specific condition being treated but can be readily determined by the skilled artisan. In general, regulatory agencies require that a protein reagent to be used as a therapeutic is formulated so as to have acceptably low levels of pyrogens. Accordingly, therapeutic formulations will generally be distinguished from other formulations in that they are substantially pyrogen free, or at least contain no more than acceptable levels of pyrogen as determined by the appropriate regulatory agency (e.g., FDA).

Therapeutic compositions of the present disclosure may be administered with a pharmaceutically acceptable diluent, carrier, or excipient, in unit dosage form. Administration may be parenteral (e.g., intravenous, subcutaneous), oral, or topical, as non-limiting examples. In addition, any gene therapy technique, using nucleic acids encoding the polypeptides of the invention, may be employed, such as naked DNA delivery, recombinant genes and vectors, cell-based delivery, including ex vivo manipulation of patients' cells, and the like.

The composition can be in the form of a pill, tablet, capsule, liquid, or sustained release tablet for oral administration; or a liquid for intravenous, subcutaneous or parenteral administration; gel, lotion, ointment, cream, or a polymer or other sustained release vehicle for local administration.

Methods well known in the art for making formulations are found, for example, in "Remington: The Science and Practice of Pharmacy" (20th ed., ed. A. R. Gennaro A R., 2000, Lippincott Williams & Wilkins, Philadelphia, Pa.). Formulations for parenteral administration may, for example, contain excipients, sterile water, saline, polyalkylene glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the compounds. Nanoparticulate formulations (e.g., biodegradable nanoparticles, solid lipid nanoparticles, liposomes) may be used to control the biodistribution of the compounds. Other potentially useful parenteral delivery systems include ethylene-vinyl acetate copolymer particles, osmotic pumps, implantable infusion systems, and liposomes. The concentration of the compound in the formulation varies depending upon a number of factors, including the dosage of the drug to be administered, and the route of administration.

The polypeptide may be optionally administered as a pharmaceutically acceptable salt, such as non-toxic acid addition salts or metal complexes that are commonly used in the pharmaceutical industry. Examples of acid addition salts include organic acids such as acetic, lactic, pamoic, maleic, citric, malic, ascorbic, succinic, benzoic, palmitic, suberic, salicylic, tartaric, methanesulfonic, toluenesulfonic, or trifluoroacetic acids or the like; polymeric acids such as tannic acid, carboxymethyl cellulose, or the like; and inorganic acid such as hydrochloric acid, hydrobromic acid, sulfuric acid phosphoric acid, or the like. Metal complexes include zinc, iron, and the like. In one example, the polypeptide is formulated in the presence of sodium acetate to increase thermal stability.

Formulations for oral use include tablets containing the active ingredient(s) in a mixture with non-toxic pharmaceutically acceptable excipients. These excipients may be, for example, inert diluents or fillers (e.g., sucrose and sorbitol), lubricating agents, glidants, and anti-adhesives (e.g., magnesium stearate, zinc stearate, stearic acid, silicas, hydrogenated vegetable oils, or talc).

Formulations for oral use may also be provided as chewable tablets, or as hard gelatin capsules wherein the active ingredient is mixed with an inert solid diluent, or as soft gelatin capsules wherein the active ingredient is mixed with water or an oil medium.

A therapeutically effective dose refers to a dose that produces the therapeutic effects for which it is administered. The exact dose will depend on the disorder to be treated, and may be ascertained by one skilled in the art using known techniques. In general, the polypeptide is administered at about 0.01 µg/kg to about 50 mg/kg per day, preferably 0.01 mg/kg to about 30 mg/kg per day, most preferably 0.1 mg/kg to about 20 mg/kg per day. The polypeptide may be given daily (e.g., once, twice, three times, or four times daily) or preferably less frequently (e.g., weekly, every two weeks, every three weeks, monthly, or quarterly). In addition, as is known in the art, adjustments for age as well as the body weight, general health, sex, diet, time of administration, drug interaction, and the severity of the disease may be necessary, and will be ascertainable with routine experimentation by those skilled in the art.

Exemplary Uses

The ErbB3 binding proteins described herein and their related variants are useful in a number of therapeutic and diagnostic applications. These include the inhibition of the biological activity of ErbB3 by competing for or blocking the binding to an ErbB3 as well as the delivery of cytotoxic or imaging moieties to cells, preferably cells expressing ErbB3. The small size and stable structure of these molecules can be particularly valuable with respect to manufacturing of the drug, rapid clearance from the body for certain applications where rapid clearance is desired or formulation into novel delivery systems that are suitable or improved using a molecule with such characteristics.

On the basis of their efficacy as inhibitors of ErbB3 biological activity, the polypeptides of this disclosure are effective against a number of cancer conditions as well as complications arising from cancer, such as pleural effusion and ascites, colorectal cancers, head and neck cancers, small cell lung cancer, non-small cell lung cancer (NSCLC) and pancreatic cancer. Non-limiting examples of cancers include bladder, blood, bone, brain, breast, cartilage, colon kidney, liver, lung, lymph node, nervous tissue, ovary, pancreatic, prostate, skeletal muscle, skin, spinal cord, spleen, stomach, testes, thymus, thyroid, trachea, urogenital tract, ureter, urethra, uterus, or vaginal cancer.

An ErbB3 binding polypeptide can be administered alone or in combination with one or more additional therapies such as chemotherapy radiotherapy, immunotherapy, surgical intervention, or any combination of these. Long-term therapy is equally possible as is adjuvant therapy in the context of other treatment strategies, as described above. Preferably, in breast cancer the combination is with Herceptin or other Her-2 therapies.

In certain embodiments of such methods, one or more polypeptide therapeutic agents can be administered, together (simultaneously) or at different times (sequentially). In addition, polypeptide therapeutic agents can be administered with another type of compounds for treating cancer or for inhibiting angiogenesis.

In certain embodiments, the subject anti-ErbB3 antibodies agents of the invention can be used alone. Alternatively, the subject agents may be used in combination with other conventional anti-cancer therapeutic approaches directed to treatment or prevention of proliferative disorders (e.g., tumor). For example, such methods can be used in prophylactic cancer prevention, prevention of cancer recurrence and metastases after surgery, and as an adjuvant of other conventional cancer therapy. The present disclosure recognizes that the effectiveness of conventional cancer therapies (e.g., chemotherapy, radiation therapy, phototherapy, immunotherapy, and surgery) can be enhanced through the use of a subject polypeptide therapeutic agent.

A wide array of conventional compounds have been shown to have anti-neoplastic activities. These compounds have been used as pharmaceutical agents in chemotherapy to shrink solid tumors, prevent metastases and further growth, or decrease the number of malignant cells in leukemic or bone marrow malignancies. Although chemotherapy has been effective in treating various types of malignancies, many anti-neoplastic compounds induce undesirable side effects. It has been shown that when two or more different treatments are combined, the treatments may work synergistically and allow reduction of dosage of each of the treatments, thereby reducing the detrimental side effects exerted by each compound at higher dosages. In other instances, malignancies that are refractory to a treatment may respond to a combination therapy of two or more different treatments.

When a polypeptide therapeutic agent of the present invention is administered in combination with another conventional anti-neoplastic agent, either concomitantly or sequentially, such therapeutic agent may be found to enhance the therapeutic effect of the anti-neoplastic agent or overcome cellular resistance to such anti-neoplastic agent. This allows decrease of dosage of an anti-neoplastic agent, thereby reducing the undesirable side effects, or restores the effectiveness of an anti-neoplastic agent in resistant cells.

Pharmaceutical compounds that may be used for combinatory anti-tumor therapy include, merely to illustrate: aminoglutethimide, amsacrine, anastrozole, asparaginase, bcg, bicalutamide, bleomycin, buserelin, busulfan, campothecin, capecitabine, carboplatin, carmustine, chlorambucil, cisplatin, cladribine, clodronate, colchicine, cyclophosphamide, cyproterone, cytarabine, dacarbazine, dactinomycin, daunorubicin, dienestrol, diethylstilbestrol, docetaxel, doxorubicin, epirubicin, estradiol, estramustine, etoposide, exemestane, filgrastim, fludarabine, fludrocortisone, fluorouracil, fluoxymesterone, flutamide, gemcitabine, genistein, goserelin, hydroxyurea, idarubicin, ifosfamide, imatinib, interferon, irinotecan, ironotecan, letrozole, leucovorin, leuprolide, levamisole, lomustine, mechlorethamine, medroxyprogesterone, megestrol, melphalan, mercaptopurine, mesna, methotrexate, mitomycin, mitotane, mitoxantrone, nilutamide, nocodazole, octreotide, oxaliplatin, paclitaxel, pamidronate, pentostatin, plicamycin, porfimer, procarbazine, raltitrexed, rituximab, streptozocin, suramin, tamoxifen, temozolomide, teniposide, testosterone, thioguanine, thiotepa, titanocene dichloride, topotecan, trastuzumab, tretinoin, vinblastine, vincristine, vindesine, and vinorelbine.

Certain chemotherapeutic anti-tumor compounds may be categorized by their mechanism of action into, for example, following groups: anti-metabolites/anti-cancer agents, such as pyrimidine analogs (5-fluorouracil, floxuridine, capecitabine, gemcitabine and cytarabine) and purine analogs, folate antagonists and related inhibitors (mercaptopurine, thioguanine, pentostatin and 2-chlorodeoxyadenosine (cladribine)); antiproliferative/antimitotic agents including natural products such as vinca alkaloids (vinblastine, vincristine, and vinorelbine), microtubule disruptors such as taxane (paclitaxel, docetaxel), vincristin, vinblastin, nocodazole, epothilones and navelbine, epipodophyllotoxins (etoposide, teniposide), DNA damaging agents (actinomycin, amsacrine, anthracyclines, bleomycin, busulfan, camptothecin, carboplatin, chlorambucil, cisplatin, cyclophosphamide, cytoxan, dactinomycin, daunorubicin, doxorubicin, epirubicin, hexamethylmelamineoxaliplatin, iphosphamide, melphalan, merchlorehtamine, mitomycin, mitoxantrone, nitrosourea, plicamycin, procarbazine, taxol, taxotere, teniposide, triethylenethiophosphoramide and etoposide (VP16)); antibiotics such as dactinomycin (actinomycin D), daunorubicin, doxorubicin (adriamycin), idarubicin, anthracyclines, mitoxantrone, bleomycins, plicamycin (mithramycin) and mitomycin; enzymes (L-asparaginase which systemically metabolizes L-asparagine and deprives cells which do not have the capacity to synthesize their own asparagine); antiplatelet agents; antiproliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nitrosoureas (carmustine (BCNU) and analogs, streptozocin), trazenes—dacarbazinine (DTIC); antiproliferative/antimitotic antimetabolites such as folic acid analogs (methotrexate); platinum coordination complexes (cisplatin, carboplatin), procarbazine, hydroxyurea, mitotane, aminoglutethimide; hormones, hormone analogs (estrogen, tamoxifen, goserelin, bicalutamide, nilutamide) and aromatase inhibitors (letrozole, anastrozole); anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory agents; antisecretory agents (breveldin); immunosuppressives (cyclosporine, tacrolimus (FK-506), sirolimus (rapamycin), azathioprine, mycophenolate mofetil); anti-angiogenic compounds (TNP-470, genistein) and growth factor inhibitors (e.g., VEGF inhibitors, fibroblast growth factor (FGF) inhibitors); angiotensin receptor blocker; nitric oxide donors; anti-sense oligonucleotides; antibodies (trastuzumab); cell cycle inhibitors and differentiation inducers (tretinoin); mTOR inhibitors, topoisomerase inhibitors (doxorubicin (adriamycin), amsacrine, camptothecin, daunorubicin, dactinomycin, eniposide, epirubicin, etoposide, idarubicin and mitoxantrone, topotecan, irinotecan), corticosteroids (cortisone, dexamethasone, hydrocortisone, methylpednisolone, prednisone, and prenisolone); growth factor signal transduction kinase inhibitors; mitochondrial dysfunction inducers and caspase activators; and chromatin disruptors.

Depending on the nature of the combinatory therapy, administration of the polypeptide therapeutic agents may be continued while the other therapy is being administered and/or thereafter. Administration of the polypeptide therapeutic agents may be made in a single dose, or in multiple doses. In some instances, administration of the polypeptide therapeutic agents is commenced at least several days prior to the conventional therapy, while in other instances, administration is begun either immediately before or at the time of the administration of the conventional therapy.

In one example of a diagnostic application, a biological sample, such as serum or a tissue biopsy, from a patient suspected of having a condition characterized by inappropriate angiogenesis is contacted with a detectably labeled polypeptide of the disclosure to detect levels of ErbB3. The levels of ErbB3 detected are then compared to levels of ErbB3 detected in a normal sample also contacted with the labeled polypeptide. An increase of at least 10%, 20%, 30%, 40%, 50%, 60%, 70%, 80%, or 90% in the levels of the ErbB3 may be considered a diagnostic indicator.

In certain embodiments, the ErbB3 binding polypeptides are further attached to a label that is able to be detected (e.g., the label can be a radioisotope, fluorescent compound, enzyme or enzyme co-factor). The active moiety may be a radioactive agent, such as: radioactive heavy metals such as iron chelates, radioactive chelates of gadolinium or manganese, positron emitters of oxygen, nitrogen, iron, carbon, or gallium, $^{43}$K, $^{52}$Fe, $^{57}$Co, $^{67}$Cu, $^{67}$Ga, $^{68}$Ga, $^{123}$I, $^{125}$I, $^{131}$I, $^{132}$I, or $^{99}$Tc. A binding agent affixed to such a moiety may be used as an imaging agent and is administered in an amount effective for diagnostic use in a mammal such as a human and the localization and accumulation of the imaging agent is then detected. The localization and accumulation of the imaging agent may be detected by radioscintigraphy, nuclear magnetic resonance imaging, computed tomography or positron emission tomography. Immunoscintigraphy using ErbB3 binding polypeptides directed at ErbB3 may be used to detect and/or diagnose cancers and vasculature. For example, any of the binding polypeptide against an ErbB3 marker labeled with $^{99}$Technetium, $^{111}$Indium, or $^{125}$Iodine may be effectively used for such imaging. As will be evident to the skilled artisan, the amount of radioisotope to be administered is dependent upon the radioisotope. Those having ordinary skill in the art can readily formulate the amount of the imaging agent to be administered based upon the specific activity and energy of a given radionuclide used as the active moiety. Typically 0.1-100 millicuries per dose of imaging agent, preferably 1-10 millicuries, most often 2-5 millicuries are administered. Thus, compositions according to the present invention useful as imaging agents comprising a targeting moiety conjugated to a radioactive moiety comprise 0.1-100 millicuries, in some embodiments preferably 1-10 millicuries, in some embodiments preferably 2-5 millicuries, in some embodiments more preferably 1-5 millicuries.

The ErbB3 binding polypeptides can also be used to deliver additional therapeutic agents (including but not limited to drug compounds, chemotherapeutic compounds, and radiotherapeutic compounds) to a cell or tissue expressing ErbB3. In one example, the ErbB3 binding polypeptide is fused to a chemotherapeutic agent for targeted delivery of the chemotherapeutic agent to a tumor cell or tissue expressing ErbB3.

The ErbB3 binding polypeptides are useful in a variety of applications, including research, diagnostic and therapeutic applications. For instance, they can be used to isolate and/or purify receptor or portions thereof, and to study receptor structure (e.g., conformation) and function.

In certain aspects, the various binding polypeptides can be used to detect or measure the expression of ErbB3, for example, on endothelial cells (e.g., venous endothelial cells), or on cells transfected with an ErbB3 gene. Thus, they also have utility in applications such as cell sorting and imaging (e.g., flow cytometry, and fluorescence activated cell sorting), for diagnostic or research purposes.

In certain embodiments, the binding polypeptides of fragments thereof can be labeled or unlabeled for diagnostic purposes. Typically, diagnostic assays entail detecting the formation of a complex resulting from the binding of a binding polypeptide to ErbB3. The binding polypeptides or fragments can be directly labeled, similar to antibodies. A variety of labels can be employed, including, but not limited to, radionuclides, fluorescers, enzymes, enzyme substrates, enzyme cofactors, enzyme inhibitors and ligands (e.g., biotin, haptens). Numerous appropriate immunoassays are known to the skilled artisan (see, for example, U.S. Pat. Nos. 3,817,827; 3,850,752; 3,901,654; and 4,098,876). When unlabeled, the binding polypeptides can be used in assays, such as agglutination assays. Unlabeled binding polypeptides can also be used in combination with another (one or more) suitable reagent which can be used to detect the binding polypeptide, such as a labeled antibody reactive with the binding polypeptide or other suitable reagent (e.g., labeled protein A).

In one embodiment, the binding polypeptides of the present invention can be utilized in enzyme immunoassays, wherein the subject polypeptides are conjugated to an enzyme. When a biological sample comprising an ErbB3 protein is combined with the subject binding polypeptides, binding occurs between the binding polypeptides and the ErbB3 protein. In one embodiment, a sample containing cells expressing an ErbB3 protein (e.g., endothelial cells) is combined with the subject antibodies, and binding occurs between the binding polypeptides and cells bearing an ErbB3 protein recognized by the binding polypeptide. These bound cells can be separated from unbound reagents and the presence of the binding polypeptide-enzyme conjugate specifically bound to the cells can be determined, for example, by contacting the sample with a substrate of the enzyme which produces a color or other detectable change when acted on by the enzyme. In another embodiment, the subject binding polypeptides can be unlabeled, and a second, labeled polypeptide (e.g., an antibody) can be added which recognizes the subject binding polypeptide.

In certain aspects, kits for use in detecting the presence of an ErbB3 protein in a biological sample can also be prepared. Such kits will include an ErbB3 binding polypeptide which binds to an ErbB3 protein or portion of said receptor, as well as one or more ancillary reagents suitable for detecting the presence of a complex between the binding polypeptide and the receptor protein or portions thereof. The polypeptide compositions of the present invention can be provided in lyophilized form, either alone or in combination with additional antibodies specific for other epitopes. The binding polypeptides and/or antibodies, which can be labeled or unlabeled, can be included in the kits with adjunct ingredients (e.g., buffers, such as Tris, phosphate and carbonate, stabilizers, excipients, biocides and/or inert proteins, e.g., bovine serum albumin). For example, the binding polypeptides and/or antibodies can be provided as a lyophilized mixture with the adjunct ingredients, or the adjunct ingredients can be separately provided for combination by the user. Generally these adjunct materials will be present in less than about 5% weight based on the amount of active binding polypeptide or antibody, and usually will be present in a total amount of at least about 0.001% weight based on polypeptide or antibody concentration. Where a second antibody capable of binding to the binding polypeptide is employed, such antibody can be provided in the kit, for instance in a separate vial or container. The second antibody, if present, is typically labeled, and can be formulated in an analogous manner with the antibody formulations described above.

Similarly, the present disclosure also provides a method of detecting and/or quantitating expression of ErbB3, wherein a composition comprising a cell or fraction thereof (e.g., membrane fraction) is contacted with a binding polypeptide which binds to an ErbB3 or portion of the receptor under conditions appropriate for binding thereto, and the binding is monitored. Detection of the binding polypeptide, indicative of the formation of a complex between binding polypeptide and ErbB3 or a portion thereof, indicates the presence of the receptor. Binding of a polypeptide to the cell can be determined by standard methods, such as those described in the working examples. The method can be used to detect expression of ErbB3 on cells from an individual. Optionally, a quantitative expression of ErbB3 on the surface of endothelial cells can be evaluated, for instance, by flow cytometry, and the staining intensity can be correlated with disease susceptibility, progression or risk.

The present disclosure also provides a method of detecting the susceptibility of a mammal to certain diseases. To illustrate, the method can be used to detect the susceptibility of a mammal to diseases which progress based on the amount of ErbB3 present on cells and/or the number of ErbB3-positive cells in a mammal.

Polypeptide sequences are indicated using standard one- or three-letter abbreviations. Unless otherwise indicated, each polypeptide sequence has amino termini at the left and a carboxy termini at the right; each single-stranded nucleic acid sequence, and the top strand of each double-stranded nucleic acid sequence, has a 5' termini at the left and a 3' termini at the right. A particular polypeptide sequence also can be described by explaining how it differs from a reference sequence.

The following terms, unless otherwise indicated, shall be understood to have the following meanings:

The terms "ErbB3 inhibitor" and "ErbB3 antagonist" are used interchangeably. Each is a molecule that detectably inhibits at least one function of ErbB3. Conversely, an "ErbB3 agonist" is a molecule that detectably increases at least one function of ErbB3. The inhibition caused by an ErbB3 inhibitor need not be complete so long as it is detectable using an assay. Any assay of a function of ErbB3 can be used, examples of which are provided herein. Examples of functions of ErbB3 that can be inhibited by an ErbB3 inhibitor, or increased by an ErbB3 agonist, include cancer cell growth or apoptosis (programmed cell death), and so on. Examples of types of ErbB3 inhibitors and ErbB3 agonists include, but are not limited to, ErbB3 binding polypeptides such as antigen binding proteins (e.g., ErbB3 inhibiting antigen binding proteins), antibodies, antibody fragments, and antibody derivatives.

The terms "peptide," "polypeptide" and "protein" each refers to a molecule comprising two or more amino acid residues joined to each other by peptide bonds. These terms encompass, e.g., native and artificial proteins, protein fragments and polypeptide analogs (such as muteins, variants, and fusion proteins) of a protein sequence as well as post-translationally, or otherwise covalently or non-covalently, modified proteins. A peptide, polypeptide, or protein may be monomeric or polymeric.

A "variant" of a polypeptide (for example, an antibody) comprises an amino acid sequence wherein one or more amino acid residues are inserted into, deleted from and/or substituted into the amino acid sequence relative to another polypeptide sequence. Disclosed variants include, for example, fusion proteins.

A "derivative" of a polypeptide is a polypeptide (e.g., an antibody) that has been chemically modified, e.g., via conjugation to another chemical moiety (such as, for example, polyethylene glycol or albumin, e.g., human serum albumin), phosphorylation, and glycosylation. Unless otherwise indicated, the term "antibody" includes, in addition to antibodies comprising two full-length heavy chains and two full-length light chains, derivatives, variants, fragments, and muteins thereof, examples of which are described below.

An "antigen binding protein" is a protein comprising a portion that binds to an antigen and, optionally, a scaffold or framework portion that allows the antigen binding portion to adopt a conformation that promotes binding of the antigen binding protein to the antigen. Examples of antigen binding proteins include antibodies, antibody fragments (e.g., an antigen binding portion of an antibody), antibody derivatives, and antibody analogs. The antigen binding protein can comprise, for example, an alternative protein scaffold or artificial scaffold with grafted CDRs or CDR derivatives. Such scaffolds include, but are not limited to, antibody-derived scaffolds comprising mutations introduced to, for example, stabilize the three-dimensional structure of the antigen binding protein as well as wholly synthetic scaffolds comprising, for example, a biocompatible polymer. See, for example, Korndorfer et al., 2003, *Proteins: Structure, Function, and Bioinformatics*, Volume 53, Issue 1:121-129; Roque et al., 2004, *Biotechnol. Prog.* 20:639-654. In addition, peptide antibody mimetics ("PAMs") can be used, as well as scaffolds based on antibody mimetics utilizing fibronection components as a scaffold.

An antigen binding protein can have, for example, the structure of a naturally occurring immunoglobulin. An "immunoglobulin" is a tetrameric molecule. In a naturally occurring immunoglobulin, each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. Human light chains are classified as kappa or lambda light chains. Heavy chains are classified as mu, delta, gamma, alpha, or epsilon, and define the antibody's isotype as IgM, IgD, IgG, IgA, and IgE, respectively. Preferably, the anti-EGFR antibodies disclosed herein are characterized by their variable domain region sequences in the heavy $V_H$ and light $V_L$ amino acid sequences. The preferred antibody is A6 which is a kappa IgG antibody. Within light and heavy chains, the variable and constant regions are joined by a "J" region of about 12 or more amino acids, with the heavy chain also including a "D" region of about 10 more amino acids. See generally, Fundamental Immunology Ch. 7 (Paul, W., ed., 2nd ed. Raven Press, N.Y. (1989)). The variable regions of each light/heavy chain pair form the antibody binding site such that an intact immunoglobulin has two binding sites.

A "multi-specific antibody" is an antibody that recognizes more than one epitope on one or more antigens. A subclass of this type of antibody is a "bi-specific antibody" which recognizes two distinct epitopes on the same or different antigens.

An antigen binding protein "specifically binds" to an antigen (e.g., human ErbB3) if it binds to the antigen with a dissociation constant of 1 nanomolar or less.

An "antigen binding domain, "antigen binding region," or "antigen binding site" is a portion of an antigen binding protein that contains amino acid residues (or other moieties) that interact with an antigen and contribute to the antigen binding protein's specificity and affinity for the antigen. For an antibody that specifically binds to its antigen, this will include at least part of at least one of its CDR domains.

An "epitope" is the portion of a molecule that is bound by an antigen binding protein (e.g., by an antibody). An epitope can comprise non-contiguous portions of the molecule (e.g., in a polypeptide, amino acid residues that are not contiguous in the polypeptide's primary sequence but that, in the context of the polypeptide's tertiary and quaternary structure, are near enough to each other to be bound by an antigen binding protein).

The "percent homology" of two polynucleotide or two polypeptide sequences is determined by comparing the sequences using the GAP computer program (a part of the GCG Wisconsin Package, version 10.3 (Accelrys, San Diego, Calif.)) using its default parameters.

A "host cell" is a cell that can be used to express a nucleic acid. A host cell can be a prokaryote, for example, *E. coli*, or it can be a eukaryote, for example, a single-celled eukaryote (e.g., a yeast or other fungus), a plant cell (e.g., a tobacco or tomato plant cell), an animal cell (e.g., a human cell, a monkey cell, a hamster cell, a rat cell, a mouse cell, or an insect cell) or a hybridoma. Examples of host cells include the COS-7 line of monkey kidney cells (ATCC CRL 1651) (Gluzman et al., 1981, *Cell* 23:175), L cells, C127 cells, 3T3 cells (ATCC CCL 163), Chinese hamster ovary (CHO) cells or their derivatives such as Veggie CHO and related cell lines which grow in serum-free media (Rasmussen et al., 1998, *Cytotechnology* 28:31) or CHO strain DX-B11, which is deficient in DHFR (Urlaub et al., 1980, *Proc. Natl. Acad. Sci. USA* 77:4216-20), HeLa cells, BHK (ATCC CRL 10) cell lines, the CV1/EBNA cell line derived from the African green monkey kidney cell line CV1 (ATCC CCL 70) (McMahan et al., 1991, *EMBO J.* 10:2821), human embryonic kidney cells such as 293,293 EBNA or MSR 293, human epidermal A431 cells, human Colo205 cells, other transformed primate cell lines, normal diploid cells, cell strains derived from in vitro culture of primary tissue, primary explants, HL-60, U937, HaK or Jurkat cells. Typically, a host cell is a cultured cell that can be transformed or transfected with a polypeptide-encoding nucleic acid, which can then be expressed in the host cell. The phrase "recombinant host cell" can be used to denote a host cell that has been transformed or transfected with a nucleic acid to be expressed. A host cell also can be a cell that comprises the nucleic acid but does not express it at a desired level unless a regulatory sequence is introduced into the host cell such that it becomes operably linked with the nucleic acid. It is understood that the term host cell refers not only to the particular subject cell but also to the progeny or potential progeny of such a cell. Because certain modifications may occur in succeeding generations due to, e.g., mutation or environmental influence, such progeny may not, in fact, be identical to the parent cell, but are still included within the scope of the term as used herein.

Antigen Binding Proteins

Antigen binding proteins (e.g., antibodies, antibody fragments, antibody derivatives, antibody muteins, and antibody variants) are polypeptides that bind to EGFR, (preferably, human ErbB3). Antigen binding proteins include antigen binding proteins that inhibit a biological activity of ErbB3.

Oligomers that contain one or more antigen binding proteins may be employed as ErbB3 antagonists. Oligomers may be in the form of covalently-linked or non-covalently-linked dimers, trimers, or higher oligomers. Oligomers comprising two or more antigen binding protein are contemplated for use, with one example being a homodimer. Other oligomers include heterodimers, homotrimers, heterotrimers, homotetramers, heterotetramers, etc.

One embodiment is directed to oligomers comprising multiple antigen binding proteins joined via covalent or non-covalent interactions between peptide moieties fused to the antigen binding proteins. Such peptides may be peptide linkers (spacers), or peptides that have the property of promoting oligomerization. Leucine zippers and certain polypeptides derived from antibodies are among the peptides that can promote oligomerization of antigen binding proteins attached thereto, as described in more detail below.

In particular embodiments, the oligomers comprise from two to four antigen binding proteins. The antigen binding proteins of the oligomer may be in any form, such as any of the forms described above, e.g., variants or fragments. Preferably, the oligomers comprise antigen binding proteins that have ErbB3 binding activity.

In one embodiment, an oligomer is prepared using polypeptides derived from immunoglobulins. Preparation of Fusion Proteins Comprising Certain Heterologous Polypeptides Fused to Various Portions of antibody-derived polypeptides (including the Fc domain) has been described, e.g., by Ashkenazi et al., 1991, *Proc. Natl. Acad. Sci. USA* 88:10535; Byrn et al., 1990, *Nature* 344:677; and Hollenbaugh et al., 1992 "Construction of Immunoglobulin Fusion Proteins", in *Current Protocols in Immunology*, Suppl. 4, pages 10.19.1-10.19.11.

One embodiment is directed to a dimer comprising two fusion proteins created by fusing an ErbB3 binding fragment of an anti-ErbB3 antibody to the Fc region of an antibody. The dimer can be made by, for example, inserting a gene fusion encoding the fusion protein into an appropriate expression vector, expressing the gene fusion in host cells transformed with the recombinant expression vector, and allowing the expressed fusion protein to assemble much like antibody molecules, whereupon interchain disulfide bonds form between the Fc moieties to yield the dimer.

The term "Fc polypeptide" includes native and mutein forms of polypeptides derived from the Fc region of an antibody. Truncated forms of such polypeptides containing the hinge region that promotes dimerization also are included. Fusion proteins comprising Fc moieties (and oligomers formed therefrom) offer the advantage of facile purification by affinity chromatography over Protein A or Protein G columns.

Another method for preparing oligomeric antigen binding proteins involves use of a leucine zipper. Leucine zipper domains are peptides that promote oligomerization of the proteins in which they are found. Leucine zippers were originally identified in several DNA-binding proteins (Landschulz et al., 1988, *Science* 240:1759), and have since been found in a variety of different proteins. Among the known leucine zippers are naturally occurring peptides and derivatives thereof that dimerize or trimerize. Examples of leucine zipper domains suitable for producing soluble oligomeric proteins are described in WO 94/10308, and the leucine zipper derived from lung surfactant protein D (SPD) described in Hoppe et al., 1994, *FEBS Letters* 344:191. The use of a modified leucine zipper that allows for stable trimerization of a heterologous protein fused thereto is described in Fanslow et al., 1994, *Semin. Immunol.* 6:267-78. In one approach, recombinant fusion proteins comprising an anti-ErbB3 antibody fragment or derivative fused to a leucine zipper peptide are expressed in suitable host cells, and the soluble oligomeric anti-ErbB3 antibody fragments or derivatives that form are recovered from the culture supernatant.

Antigen-binding fragments of antigen binding proteins of the invention may be produced by conventional techniques. Examples of such fragments include, but are not limited to, Fab and F(ab')$_2$ fragments.

The present disclosure provides monoclonal antibodies that bind to ErbB3. Monoclonal antibodies may be produced using any technique known in the art, e.g., by immortalizing spleen cells harvested from the transgenic animal after completion of the immunization schedule. The spleen cells can be immortalized using any technique known in the art, e.g., by fusing them with myeloma cells to produce hybridomas. Myeloma cells for use in hybridoma-producing fusion procedures preferably are non-antibody-producing, have high fusion efficiency, and enzyme deficiencies that render them incapable of growing in certain selective media which support the growth of only the desired fused cells (hybridomas). Examples of suitable cell lines for use in mouse fusions include Sp-20, P3-X63/Ag8, P3-X63-Ag8.653, NS1/1.Ag 4 1, Sp210-Ag14, FO, NSO/U, MPC-11, MPC11-X45-GTG 1.7 and S194/5XX0 Bul; examples of cell lines used in rat fusions include R210.RCY3, Y3-Ag 1.2.3, IR983F and 48210. Other cell lines useful for cell fusions are U-266, GM1500-GRG2, LICR-LON-HMy2 and UC729-6.

Antigen binding proteins directed against ErbB3 can be used, for example, in assays to detect the presence of ErbB3 polypeptides, either in vitro or in vivo. The antigen binding proteins also may be employed in purifying ErbB3 proteins by immunoaffinity chromatography. Blocking antigen binding proteins can be used in the methods disclosed herein. Such antigen binding proteins that function as ErbB3 antagonists may be employed in treating any ErbB3-induced condition, including but not limited to various cancers.

Antigen binding proteins may be employed in an in vitro procedure, or administered in vivo to inhibit ErbB3-induced biological activity. Disorders caused or exacerbated (directly or indirectly) by the proteolytic activation of ErbB3, examples of which are provided herein, thus may be treated. In one embodiment, the present invention provides a therapeutic method comprising in vivo administration of an ErbB3 blocking antigen binding protein to a mammal in need thereof in an amount effective for reducing an ErbB3-induced biological activity.

Antigen binding proteins include fully human monoclonal antibodies that inhibit a biological activity of ErbB3.

Antigen binding proteins may be prepared by any of a number of conventional techniques. For example, they may be purified from cells that naturally express them (e.g., an antibody can be purified from a hybridoma that produces it), or produced in recombinant expression systems, using any technique known in the art. See, for example, Monoclonal Antibodies, Hybridomas: A New Dimension in Biological Analyses, Kennet et al. (eds.), Plenum Press, New York (1980); and Antibodies: A Laboratory Manual, Harlow and Land (eds.), Cold Spring Harbor Laboratory Press, Cold Spring Harbor, N.Y., (1988).

Any expression system known in the art can be used to make the recombinant polypeptides of the invention. In general, host cells are transformed with a recombinant expression vector that comprises DNA encoding a desired polypeptide. Among the host cells that may be employed are prokaryotes, yeast or higher eukaryotic cells. Prokaryotes include gram negative or gram positive organisms, for example *E. coli* or *bacilli*. Higher eukaryotic cells include insect cells and established cell lines of mammalian origin. Examples of suitable mammalian host cell lines include the COS-7 line of monkey kidney cells (ATCC CRL 1651) (Gluzman et al., 1981, *Cell* 23:175), L cells, 293 cells, C127 cells, 3T3 cells (ATCC CCL 163), Chinese hamster ovary (CHO) cells, HeLa cells, BHK (ATCC CRL 10) cell lines, and the CV1/EBNA cell line derived from the African green monkey kidney cell line CV1 (ATCC CCL 70) as described by McMahan et al., 1991, *EMBO J.* 10: 2821. Appropriate cloning and expression vectors for use with bacterial, fungal, yeast, and mammalian cellular hosts are described by Pouwels et al. (Cloning Vectors: A Laboratory Manual, Elsevier, N.Y., 1985).

The transformed cells can be cultured under conditions that promote expression of the polypeptide, and the polypeptide recovered by conventional protein purification procedures. One such purification procedure includes the use of affinity chromatography, e.g., over a matrix having all or a portion (e.g., the extracellular domain) of ErbB3 bound thereto. Polypeptides contemplated for use herein include substantially homogeneous recombinant mammalian anti-ErbB3 antibody polypeptides substantially free of contaminating endogenous materials.

Antigen binding proteins may be prepared, and screened for desired properties, by any of a number of known techniques. Certain of the techniques involve isolating a nucleic acid encoding a polypeptide chain (or portion thereof) of an antigen binding protein of interest (e.g., an anti-ErbB3 antibody), and manipulating the nucleic acid through recombinant DNA technology. The nucleic acid may be fused to another nucleic acid of interest, or altered (e.g., by mutagenesis or other conventional techniques) to add, delete, or substitute one or more amino acid residues, for example.

Single chain antibodies may be formed by linking heavy and light chain variable domain (Fv region) fragments via an amino acid bridge (short peptide linker), resulting in a single polypeptide chain. Such single-chain Fvs (scFvs) have been prepared by fusing DNA encoding a peptide linker between DNAs encoding the two variable domain polypeptides ($V_L$ and $V_H$). The resulting polypeptides can fold back on themselves to form antigen-binding monomers, or they can form multimers (e.g., dimers, trimers, or tetramers), depending on the length of a flexible linker between the two variable domains (Kortt et al., 1997, *Prot. Eng.* 10:423; Kortt et al., 2001, *Biomol. Eng.* 18:95-108). By combining different $V_L$ and $V_H$-comprising polypeptides, one can form multimeric scFvs that bind to different epitopes (Kriangkum et al., 2001, *Biomol. Eng.* 18:31-40). Techniques developed for the production of single chain antibodies include those described in U.S. Pat. No. 4,946,778; Bird, 1988, *Science* 242:423; Huston et al., 1988, *Proc. Natl. Acad. Sci. USA* 85:5879; Ward et al., 1989, *Nature* 334:544, de Graaf et al., 2002, *Methods Mol. Biol.* 178:379-87.

Techniques are known for deriving an antibody of a different subclass or isotype from an antibody of interest, i.e., subclass switching. Thus, IgG antibodies may be derived from an IgM antibody, for example, and vice versa. Such techniques allow the preparation of new antibodies that possess the antigen-binding properties of a given antibody (the parent antibody), but also exhibit biological properties associated with an antibody isotype or subclass different from that of the parent antibody. Recombinant DNA techniques may be employed. Cloned DNA encoding particular antibody polypeptides may be employed in such procedures, e.g., DNA encoding the constant domain of an antibody of the desired isotype (Lantto et al., 2002, *Methods Mol. Biol.* 178:303-16). Moreover, if an IgG4 is desired, it may also be desired to introduce a point mutation (CPSCP→CPPCP) in the hinge region (Bloom et al., 1997, *Protein Science* 6:407) to alleviate a tendency to form intra-H chain disulfide bonds that can lead to heterogeneity in the IgG4 antibodies.

In particular embodiments, antigen binding proteins of the present invention have a binding affinity ($K_a$) for ErbB3 of at least $10^6$. In other embodiments, the antigen binding proteins exhibit a $K_a$ of at least $10^7$, at least $10^8$, at least $10^9$, or at least $10^{10}$. In another embodiment, the antigen binding protein exhibits a $K_a$ substantially the same as that of an antibody described herein in the Examples.

In another embodiment, the present disclosure provides an antigen binding protein that has a low dissociation rate from ErbB3. In one embodiment, the antigen binding protein has a $K_{off}$ of $1\times10^{-4}$ to $^{-1}$ or lower. In another embodiment, the $K_{off}$ is $5\times10^{-5}$ to $^{-1}$ or lower. In another embodiment, the $K_{off}$ is substantially the same as an antibody described herein. In another embodiment, the antigen binding protein binds to ErbB3 with substantially the same $K_{off}$ as an antibody described herein.

In another aspect, the present disclosure provides an antigen binding protein that inhibits an activity of ErbB3. In one embodiment, the antigen binding protein has an $IC_{50}$ of 1000 nM or lower. In another embodiment, the $IC_{50}$ is 100 nM or lower; in another embodiment, the $IC_{50}$ is 10 nM or lower. In another embodiment, the $IC_{50}$ is substantially the same as that of an antibody described herein in the Examples. In another embodiment, the antigen binding protein inhibits an activity of ErbB3 with substantially the same $IC_{50}$ as an antibody described herein.

In another aspect, the present disclosure provides an antigen binding protein that binds to human ErbB3 expressed on the surface of a cell and, when so bound, inhibits ErbB3 signaling activity in the cell without causing a significant reduction in the amount of ErbB3 on the surface of the cell. Any method for determining or estimating the amount of ErbB3 on the surface and/or in the interior of the cell can be used. In other embodiments, binding of the antigen binding protein to the ErbB3-expressing cell causes less than about 75%, 50%, 40%, 30%, 20%, 15%, 10%, 5%, 1%, or 0.1% of the cell-surface ErbB3 to be internalized.

In another aspect, the present disclosure provides an antigen binding protein having a half-life of at least one day in vitro or in vivo (e.g., when administered to a human subject). In one embodiment, the antigen binding protein has a half-life of at least three days. In another embodiment, the antigen binding protein has a half-life of four days or longer. In another embodiment, the antigen binding protein has a half-life of eight days or longer. In another embodiment, the antigen binding protein is derivatized or modified such that it has a longer half-life as compared to the underivatized or unmodified antigen binding protein. In another embodiment, the antigen binding protein contains one or more point mutations to increase serum half life, such as described in WO00/09560, incorporated by reference herein.

The present disclosure further provides multi-specific antigen binding proteins, for example, bispecific antigen binding protein, e.g., antigen binding protein that bind to two different epitopes of ErbB3, or to an epitope of ErbB3 and an epitope of another molecule, via two different antigen binding sites or regions. Moreover, bispecific antigen binding protein as disclosed herein can comprise an ErbB3 binding site from one of the herein-described antibodies and a second ErbB3 binding region from another of the herein-described antibodies, including those described herein by reference to other publications. Alternatively, a bispecific antigen binding protein may comprise an antigen binding site from one of the herein described antibodies and a second antigen binding site from another ErbB3 antibody that is known in the art, or from an antibody that is prepared by known methods or the methods described herein.

Numerous methods of preparing bispecific antibodies are known in the art. Such methods include the use of hybrid-hybridomas as described by Milstein et al., 1983, *Nature* 305:537, and chemical coupling of antibody fragments (Brennan et al., 1985, *Science* 229:81; Glennie et al., 1987, *J. Immunol.* 139:2367; U.S. Pat. No. 6,010,902). Moreover, bispecific antibodies can be produced via recombinant means, for example by using leucine zipper moieties (i.e., from the Fos and Jun proteins, which preferentially form heterodimers; Kostelny et al., 1992, *J. Immunol.* 148:1547) or other lock and key interactive domain structures as described in U.S. Pat. No. 5,582,996. Additional useful techniques include those described in U.S. Pat. Nos. 5,959,083; and 5,807,706.

In another aspect, the antigen binding protein comprises a derivative of an antibody. The derivatized antibody can comprise any molecule or substance that imparts a desired property to the antibody, such as increased half-life in a particular use. The derivatized antibody can comprise, for example, a detectable (or labeling) moiety (e.g., a radioactive, colorimetric, antigenic or enzymatic molecule, a detectable bead (such as a magnetic or electrodense (e.g., gold bead), or a molecule that binds to another molecule (e.g., biotin or streptavidin), a therapeutic or diagnostic moiety (e.g., a radioactive, cytotoxic, or pharmaceutically active moiety), or a molecule that increases the suitability of the antibody for a particular use (e.g., administration to a subject, such as a human subject, or other in vivo or in vitro uses). Examples of molecules that can be used to derivatize an antibody include albumin (e.g., human serum albumin) and polyethylene glycol (PEG). Albumin-linked and PEGylated derivatives of antibodies can be prepared using techniques well known in the art. In one embodiment, the antibody is conjugated or otherwise linked to transthyretin (TTR) or a TTR variant. The TTR or TTR variant can be chemically modified with, for example, a chemical selected from the group consisting of dextran, poly (n-vinyl pyurrolidone), polyethylene glycols, propropylene glycol homopolymers, polypropylene oxide/ethylene oxide co-polymers, polyoxyethylated polyols and polyvinyl alcohols.

The following terms, unless otherwise indicated, shall be understood to have the following meanings:

Indications

In one aspect, the present disclosure provides methods of treating a subject. The method can, for example, have a generally salubrious effect on the subject, e.g., it can increase the subject's expected longevity. Alternatively, the method can, for example, treat, prevent, cure, relieve, or ameliorate ("treat") a disease, disorder, condition, or illness ("a condition"). Among the conditions to be treated are conditions characterized by inappropriate expression or activity of ErbB3. In some such conditions, the expression or activity level is too high, and the treatment comprises administering an ErbB3 antagonist as described herein. The disorders or conditions are cancer-related. In particular, those cancers include, but are not limited to, breast, lung, ovarian and colon carcinoma and various myelomas.

Specific medical conditions and diseases that are treatable or preventable with the antigen binding proteins of this disclosure include various cancers.

Therapeutic Methods and Administration of Antigen Binding Proteins

Certain methods provided herein comprise administering an ErbB3 binding antigen binding protein to a subject, thereby reducing an ErbB3-induced biological response that plays a role in a particular condition. In particular embodiments, methods of the invention involve contacting endogenous ErbB3 with an ErbB3 binding antigen binding protein, e.g., via administration to a subject or in an ex vivo procedure.

The term "treatment" encompasses alleviation or prevention of at least one symptom or other aspect of a disorder, or reduction of disease severity, and the like. An antigen binding protein need not effect a complete cure, or eradicate every symptom or manifestation of a disease, to constitute a viable therapeutic agent. As is recognized in the pertinent field, drugs employed as therapeutic agents may reduce the severity of a given disease state, but need not abolish every manifestation of the disease to be regarded as useful therapeutic agents. Similarly, a prophylactically administered treatment need not be completely effective in preventing the onset of a condition in order to constitute a viable prophylactic agent. Simply reducing the impact of a disease (for example, by reducing the number or severity of its symptoms, or by increasing the effectiveness of another treatment, or by producing another beneficial effect), or reducing the likelihood that the disease will occur or worsen in a subject, is sufficient. One embodiment of the invention is directed to a method comprising administering to a patient an ErbB3 antagonist in an amount and for a time sufficient to induce a sustained improvement over baseline of an indicator that reflects the severity of the particular disorder.

As is understood in the pertinent field, pharmaceutical compositions comprising the antibodies and fragments thereof of the disclosure are administered to a subject in a manner appropriate to the indication. Pharmaceutical compositions may be administered by any suitable technique, including but not limited to, parenterally, topically, or by inhalation. If injected, the pharmaceutical composition can be administered, for example, via intra-articular, intravenous, intramuscular, intralesional, intraperitoneal or subcutaneous routes, by bolus injection, or continuous infusion. Localized administration, e.g. at a site of disease or injury is contemplated, as are transdermal delivery and sustained release from implants. Delivery by inhalation includes, for example, nasal or oral inhalation, use of a nebulizer, inhalation of the antagonist in aerosol form, and the like. Other alternatives include eyedrops; oral preparations including pills, syrups, lozenges or chewing gum; and topical preparations such as lotions, gels, sprays, and ointments.

Use of antigen binding proteins in ex vivo procedures also is contemplated. For example, a patient's blood or other bodily fluid may be contacted with an antigen binding protein that binds ErbB3 ex vivo. The antigen binding protein may be bound to a suitable insoluble matrix or solid support material.

Advantageously, antigen binding proteins are administered in the form of a composition comprising one or more additional components such as a physiologically acceptable carrier, excipient or diluent. Optionally, the composition additionally comprises one or more physiologically active agents, for example, a second inflammation- or immune-inhibiting substance, an anti-angiogenic substance, an analgesic substance, etc., non-exclusive examples of which are provided herein. In various particular embodiments, the composition comprises one, two, three, four, five, or six physiologically active agents in addition to an EGFR binding antigen binding protein Combination Therapy In another aspect, the present disclosure provides a method of treating a subject with an ErbB3 inhibiting antigen binding protein and one or more other treatments. In one embodiment, such a combination therapy achieves synergy or an additive effect by, for example, attacking multiple sites or molecular targets in a tumor. Types of combination therapies that can be used in connection with the present invention include inhibiting or activating (as appropriate) multiple nodes in a single disease-related pathway, multiple pathways in a target cell, and multiple cell types within a target tissue.

In a preferred embodiment, an anti-ErbB3 antibody provided herein is administered together with an antibody selected from the group consisting of an anti-HER2 antibody, an anti-HER3 antibody, an anti-EGFR antibody and combinations thereof (see examples 10 and 11 below).

In another embodiment, a combination therapy method comprises administering to the subject two, three, four, five, six, or more of the ErbB3 agonists or antagonists described herein. In another embodiment, the method comprises administering to the subject two or more treatments that together inhibit or activate (directly or indirectly) ErbB3-mediated signal transduction. Examples of such methods include using combinations of two or more ErbB3 inhibiting antigen binding proteins, of an ErbB3 inhibiting antigen binding protein and one or more other therapeutic moiety having anti-cancer properties (for example, cytotoxic agents, and/or immunomodulators), or of an ErbB3 inhibiting antigen binding protein and one or more other treatments (e.g., surgery, or radiation). Furthermore, one or more anti-ErbB3 antibodies or antibody derivatives can be used in combination with one or more molecules or other treatments, wherein the other molecule(s) and/or treatment(s) do not directly bind to or affect ErbB3, but which combination is effective for treating or preventing the condition being treated. In one embodiment, one or more of the molecule(s) and/or treatment(s) treats or prevents a condition that is caused by one or more of the other molecule(s) or treatment(s) in the course of therapy, e.g., nausea, fatigue, alopecia, cachexia, insomnia, etc. In every case where a combination of molecules and/or other treatments is used, the individual molecule(s) and/or treatment(s) can be administered in any order, over any length of time, which is effective, e.g., simultaneously, consecutively, or alternately. In one embodiment, the method of treatment comprises completing a first course of treatment with one molecule or other treatment before beginning a second course of treatment. The length of time between the end of the first course of treatment and beginning of the second course of treatment can be any length of time that allows the total course of therapy to be effective, e.g., seconds, minutes, hours, days, weeks, months, or even years.

In another embodiment, the method comprises administering one or more of the ErbB3 antagonists described herein and one or more other treatments (e.g., a therapeutic or palliative treatment). Where a method comprises administering more than one treatment to a subject, it is to be understood that the order, timing, number, concentration, and volume of the administrations is limited only by the medical requirements and limitations of the treatment, i.e., two treatments can be administered to the subject, e.g., simultaneously, consecutively, alternately, or according to any other regimen.

Example 1

This example describes in vitro data showing the binding specificity of anti-ErbB3 antibodies, relative to other members of the ErbB (EGFR) family. The binding of the antibodies towards mouse ErbB3 was also assessed to check for the cross reactivity towards the mouse antigen of interest.

Costar Clear EIA/RIA 96-Well, half area plates were coated with appropriated human recombinant proteins (ErbB3, EGFR, or ERbB2) or mouse ErbB3 and incubated overnight at 4° C.

Plates were washed three times with PBS. Wells were blocked for 1H at room temperature with Casein in PBS. Plates were washed three times with PBS. Anti-ErbB3 antibodies or phage soup were added to wells and incubated for 1 hour at room temperature. Plates were washed three times with PBS prior to addition of appropriate peroxidase-linked detection antibody for one hour at room temperature. After three washes, TMB substrate (Pierce), followed by stop solution (2 M $H_2SO_4$) were added as recommended in manufacturer's protocol. The binding of ErbB3 antibodies was determined by measuring the OD450 using a SpectraMax plate reader and analyzed using the Microsoft EXCEL program.

Results are depicted in FIG. 1A and show that anti-ErbB3 antibodies specifically bind to recombinant ErbB3 in an ELISA, but do not show any appreciable binding to EGFR, or ErbB2. FIG. 1B shows that anti-ErbB3 antibodies cross-react with mouse ErbB3.

Example 2

This example illustrates the binding of anti-ErbB3 antibodies to endogenous human ErbB3 expressed on human cancer cells, as assayed by flow cytometry. $EC_{50}$ values for antibodies were determined as follows.

Her3 expressing MCF7 cells were harvested with enzyme-free Cell Dissociation Buffer (GIBCO) and transferred to V-Bottom 96 well-plates (50,000 cells/well). Cells were incubated on ice for 30 min with serial dilutions of anti-ErbB3 antibodies in FACS buffer (PBS+2% FBS)+NaN$_3$. After 2 washes in FACS buffer, a 1:1000 dilution of Phycoerythrin conjugated anti-Human IgG (γ-chain specific) was added and incubated for 30 min. Following a final wash, fluorescence intensity was measured on an Intellicyt High Throughput Flow Cytometer (HTFC). Data were analyzed using Graphpad Prism software using non-linear regression fit. Data points are shown as the median fluorescence intensity (MFI) of positively labeled cells +/− Standard Error. EC$_{50}$ values are reported as the concentration of antibody to achieve 50% of maximal ErbB3 antibodies binding to ErbB3 expressing cells. In parallel, cell binding was also assessed with the same method on CHO—K1 cells, which do not express human ErbB3 endogenously and thus served as a negative control.

As shown in FIG. 2 and Table 1, selected antibodies strongly bound ErbB3 expressing MCF7 cells, and displayed EC$_{50}$ values ranging from 0.049 to 5.97 nM. Most of the antibody showed little or no binding to cells not expressing human ErbB3 (CHO-K1 cells). These data altogether demonstrate a strong and specific binding of the antibodies to endogenous ErbB3.

Table 1 shows binding characteristics (EC$_{50}$, in Mol.L$^{-1}$) of anti-ErbB3 antibodies to cells either expressing ErbB3 (MCF7) or not (CHO-K1). The results indicate that most anti-ErbB3 antibodies bind specifically to ErbB3-positive Cells.

TABLE 1

| EC50 (M) | ErbB3 (+) Cell Line (MCF7) | ErbB3 (−) Cell Line (CHO) |
| --- | --- | --- |
| A01 | 5.71E−09 | — |
| A02 | 1.222E−09 | 3.519E−08 |
| A04 | 1.628E−10 | — |
| A08 | 7.472E−10 | — |
| A11 | 2.19E−10 | — |
| B01 | 2.647E−09 | — |
| B08 | 9.215E−11 | — |
| B11 | 4.902E−11 | — |
| C03 | 4.266E−10 | 2.16E−09 |
| D01 | 4.025E−09 | >1.0E−06 |
| D03 | 5.972E−09 | — |
| D04 | 2.421E−11 | — |
| D07 | 9.332E−10 | — |
| D08 | 1.933E−09 | — |
| D10 | 2.01E−09 | — |
| E01 | 2.53E−09 | 1.305E−08 |
| E08 | 3.067E−09 | >1.0E−08 |

Example 3

This example illustrates Analytical Size-Exclusion Chromatography (ANSEC) analysis of anti-ErbB3 monoclonal antibodies was performed under native conditions on a Waters Breeze HPLC system coupled to an external Wyatt Technology miniDAWN Treos multi-angle light scattering (MALS) system. Chromatography separation was performed in PBS pH 7.4 buffer at 0.5 mL/min flow rate using BioSep-SEC-s3000, 300×7.8 mm column (Phenomenex). The duration of each run was 30 minutes. Prior to process samples, the column running conditions were confirmed with BIO-RAD gel filtration protein standard (Cat #, 151-1901: Thyroglobin=670 KDa; Gamma-globulin=158 KDa; Ovalbumin=44 KDa; Myoglobin=17 KDa; Vitamin B12=1.35 KDa). Absolute molecular weight of single homogeneous protein band separated on ANSEC run was evaluated using online MALS system with ≥95% confidence.

Figure 3:
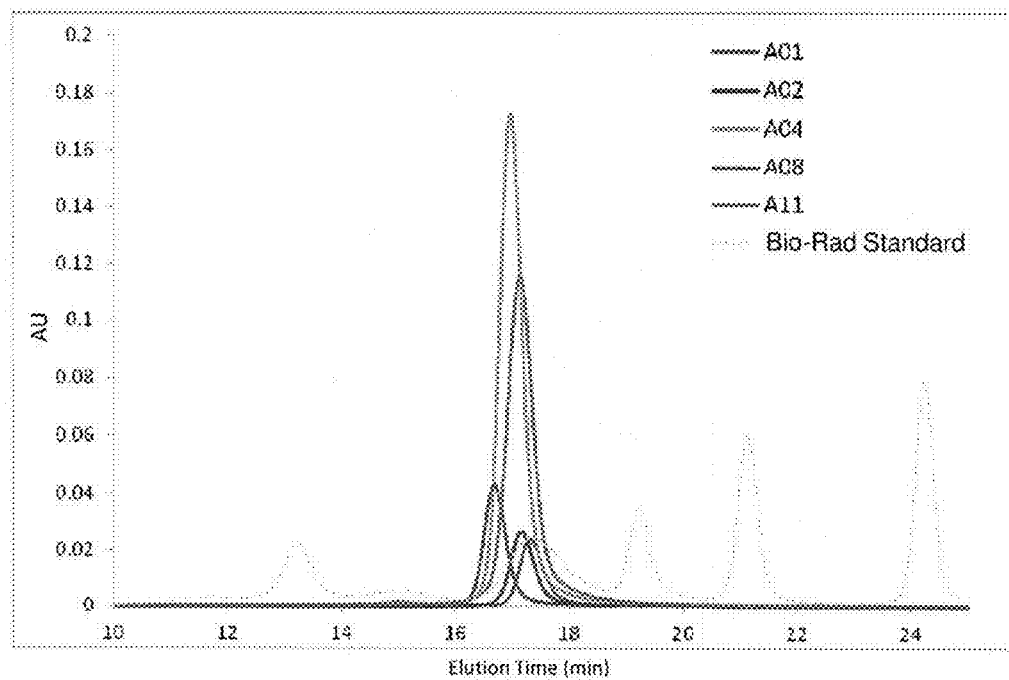
FIG. 3 is a HPLC-ANSEC analysis of selected antibodies as shown.

The results are shown in FIG. 3 which provide overlaid ANSEC chromatograms (Ultra Violet trace at 280 nm) of selected anti-ErbB3 antibodies as well as Bio-Rad Standard (grey square dot) under isocratic elution conditions. All antibodies displayed homogenous distribution, with no detectable aggregation observed. Table 2 indicates the average molecular weights determined for selected antibodies.

Example 4

This example illustrates in vitro data showing the inhibition of Heregulin-stimulated cell proliferation by anti-ERbB3 antibodies.

In this example, 10,000 MCF7 breast cancer cells were plated into each well of a 96-well cell culture plate in complete culture media. After 24 hr, media was removed, and cells were incubated with various concentrations of antibodies in DMEM+0.5% FBS for 45 min, followed by addition of NRG1-beta 1 to a final concentration of 10 ng/ml. Cells were incubated for 72 hr at 37° C., after which the Promega Cell Titer 96 Non-radioactive Cell Proliferation (MTT) Assay kit was used to evaluate cell proliferation, as recommended by manufacturer's protocol. The proliferative index was calculated as the OD$_{570}$ of NRG1-beta 1 treated sample (with or without antibody treatment) relative to untreated cells. Data were analyzed using Graphpad Prism software using non-linear regression fit.

Figure 4:
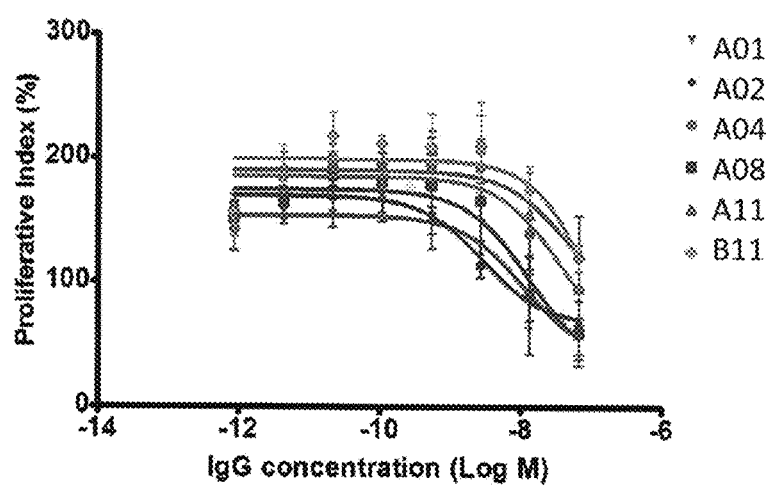
FIG. 4 shows the inhibition of Heregulin-mediated MCF7 proliferation. Cells were incubated for 3 days with Heregulin in the presence or absence of anti-ErbB3 antibodies. Cell proliferation was then analyzed by MTT assay. The graph shows the dose curves obtained for selected antibodies. Under the graph is a table with the $IC_{50}$ values obtained for those antibodies.

Results, shown in FIG. 4, indicate that anti-ErbB3 antibodies inhibit cell proliferation induced by NRG1-beta 1. Among them, A01, A02, and A08 were the most potent, with IC$_{50}$ values of 10.6 nM, 2.8 nM and 12.8 nM respectively.

Table 2 indicates the estimated molecular weights for the selected antibodies, as determined by ANSEC-MALS.

TABLE 2

| Sample ID | MW on MALS (+−5kDa) |
| --- | --- |
| ErbB3- A01 | 172.5 |
| ErbB3- A02 | 146.3 |
| ErbB3- A04 | 140 |
| ErbB3- A08 | 149.9 |
| ErbB3- A11 | 162.5 |

Example 5

This example illustrates in vitro data showing NRG1 beta-1 stimulated phosphorylation of Her3 in MCF7 breast cancer cells. This example demonstrates the ability of antibodies to block the activation of ErbB3, in cancer cells, and therefore its function potentially. Typically, 20,000 MCF7 cells were plated in the wells of a 96-well cell culture cluster in 100 μl Phenol Red-free DMEM media supplemented with 10% FBS. Cells were then starved for 20 hr in 100 μl starvation media (Phenol Red-free DMEM+0% FBS). Antibodies were diluted to 20 μg/ml (2× final concentration) in 50 μl serum-free media, then added to the cells after removal of starvation media. After 3 hr incubation, 50 μl of 20 ng/ml NRG1-beta1 was added to the cells for a final concentration of 10 ng/ml. After 10 min, cells were washed with ice-cold PBS supplemented with NaVO$_4$, and then lyzed in 1× Cell Lysis Buffer (Cell Signaling Technology). Phosphorylation of Her3 was detected using PathScan® Phospho-HER3/ErbB3 (panTyr) Sandwich ELISA Kit according to manufacturer's protocol (Cell Signaling Technology) adjusted for half area ELISA plates. The effect of antibody was determined by measuring the OD450 using a SpectraMax plate reader and analyzed using GraphPad Prism 5 software.

Figure 5:
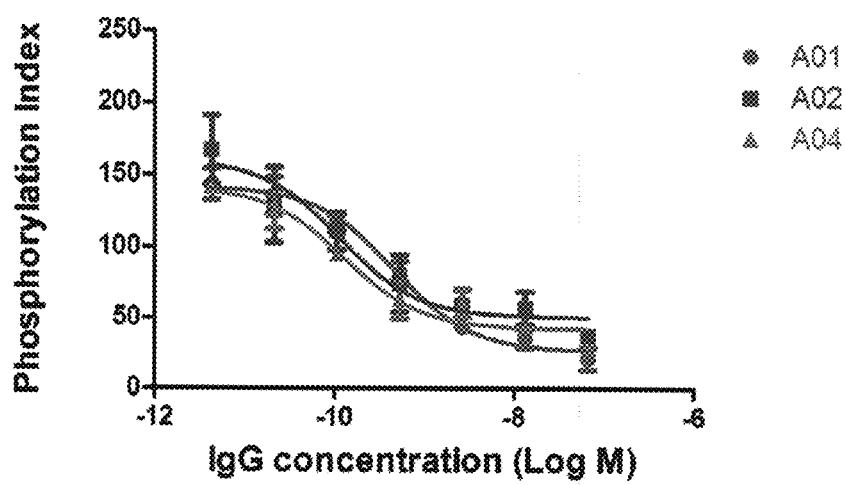
FIG. 5 shows that anti-ErB3 antibodies inhibit Her3 Tyrosine phosphorylation in a dose dependent manner, as measured by ELISA.

The results, shown in FIG. 5, indicate that anti-ErbB3 A01, A02, and A04 antibodies strongly inhibit ErbB3 phosphorylation induced by Heregulin, in a dose dependent manner, with IC50 values of 0.46, 0.12, and 0.13 nM respectively.

Example 6

This example illustrates in vitro data showing NRG1 beta-1 stimulated phosphorylation of ERK1/2 MAPK in MCF7 breast cancer cells. This example demonstrates the ability of antibodies to block the activation of ERK1/2 and hereby the function of Her3 in cancer cells. Typically, 20,000 MCF7 cells were plated in the wells of a 96-well cell culture cluster in 100 μl Phenol Red-free DMEM media supplemented with 10% FBS. Cells were then starved for 20 hr in 100 starvation media (Phenol Red-free DMEM+0% FBS). Antibodies were diluted to 20 μg/ml (2× final concentration) in 50 μl serum-free media, and added to the cells after removal of starvation media. After 3 hr incubation, 50 μl of 20 ng/ml NRG1 beta 1 was added to the cells for a final concentration of 10 ng/ml. After 10 min, cells were washed with ice-cold PBS supplemented with $NaVO_4$, and then lyzed in 1× Cell Lysis Buffer (Cell Signaling Technology). Phosphorylation of Her3 was detected using PathScan® Phospho-p44/42 MAPK (Thr202/Tyr204) Sandwich ELISA Antibody Pair according to manufacturer's protocol (Cell Signaling Technology) adjusted for half area ELISA plates. The effect of antibody was determined by measuring the OD450 using a SpectraMax plate reader and analyzed using GraphPad Prism 5 software.

Figure 6:
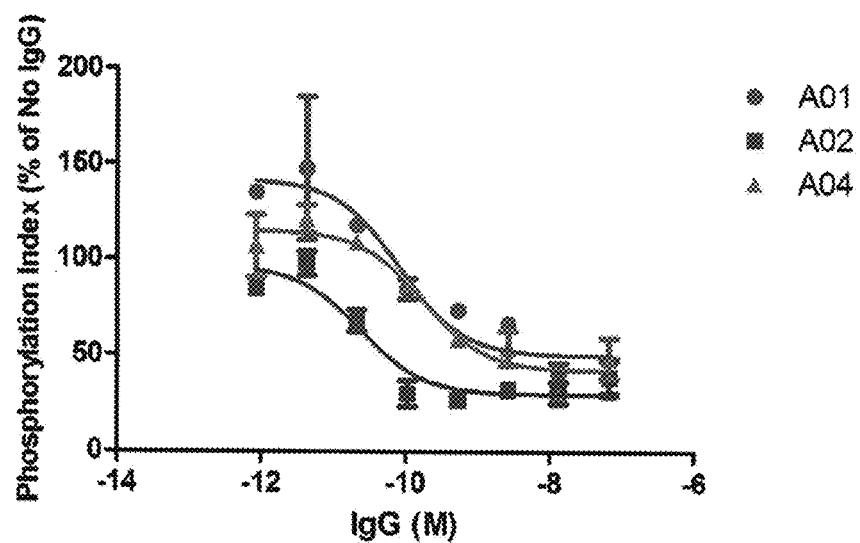
FIG. 6 shows that anti-ErbB3 antibodies inhibit p42/44 MAP kinase phosphorylation in a dose dependent manner, as measured by ELISA.

The results, shown in FIG. 6, indicate that anti-ErbB3 A01, A02, and A04 antibodies strongly inhibit ERK1/2 phosphorylation induced by NRG1 beta-1, in a dose dependent manner, with IC50 values of 0.46, 0.12, and 0.13 nM respectively.

Example 7

Figure 7:
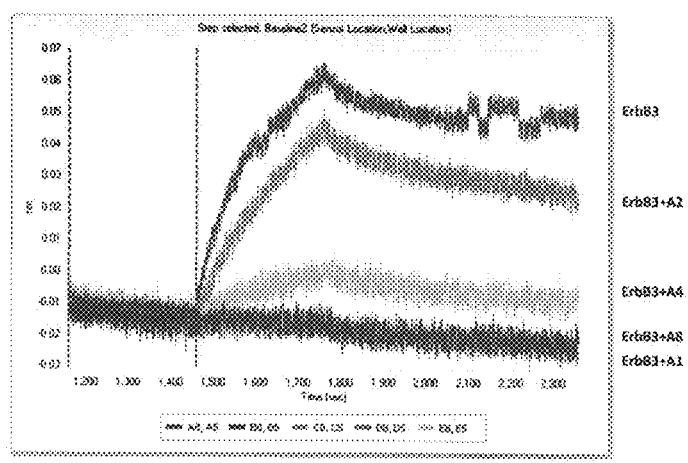
FIG. 7 shows that exemplary anti-ErbB3 antibodies block ErbB3 binding to immobilized Heregulin, as measured by OCTET. The absence of a binding signal reflects a strong inhibition of ErB3 binding to its ligand.

This example illustrates the ability of antibodies to block the interaction between Her3 receptor and its natural ligand NRG1-beta 1 (Heregulin/Neuregulin). Recombinant human NRG1-b1 was immobilized on AR2G sensor using standard NHS/EDC coupling methodology. Then recombinant human ErbB3/Fc was loaded alone (2 μg/ml final) or pre-incubated with anti-ErbB3 antibodies, in mixtures of 2 μg/ml and 20 μg/ml final respectively. The binding of ErbB3 in the presence of the antibodies was assessed on a ForteBio's Octet® platform. As shown in FIG. 7, results indicate that A01 and A08 strongly inhibited the binding of ErbB3 to its ligand, whereas A04 and A02 only partially inhibited the binding.

Example 8

This example illustrates the ability of anti-ErbB3 antibodies to induce receptor internalization, a prerequisite for a decrease in ErbB3 cell surface expression, and thus for the inhibition of ErbB3 function in cancer cells.

Cells were plated at 20.000 cells in each well of 96 well plates. The day after, cells were starved in serum-free media for 20H. Media was then replaced with serum free media containing 10 ug/ml of anti-ErbB3 antibody, or a non relevant control antibody, or no antibody, for increasing periods of time, ranging from 0 to 90 min. Cells were then washed briefly once with trypsin, then three times with PBS, and fixed in paraformaldehyde (4% in PBS) for 10 min at room temperature. After 3 washes in PBS, cells were permeabilised with Blocker Casein in PBS (Pierce)+0.25% NP40 for 10 min at room temperature, washed 3 times again and incubated with Blocker Casein in PBS for 30 min. Anti-human ErbB3-Phycoerythrin was then added to 1/1000 final dilution and cells were further incubated at room temperature for 1H. Following 3 washes, cell nuclei were labeled with Hoechst for 5 min. Receptor localization was assessed on an EVOS-F1 microscope and images were analyzed with ImageJ software.

Figure 8:
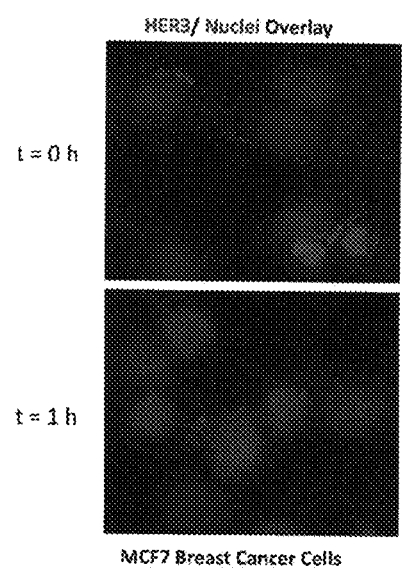
FIG. 8 is a picture obtained by fluorescence microscopy analysis, showing that ErbB3-A04 antibody can induce ErbB3 Receptor Internalization in MCF7.

Results, shown in FIG. 8, illustrate the levels of ErbB3 on surfaces of MCF7 cells in the absence and the presence of an exemplary anti-ErbB3 antibody. After 1 hour incubation with A04, ErbB3 is mainly detected in the cytoplasmic/endosomal compartment of the cells, whereas in the presence of the control antibody (data not shown), or in the absence of antibody, ErbB3 is mostly detected at the cell surface.

Example 9

Figure 9:
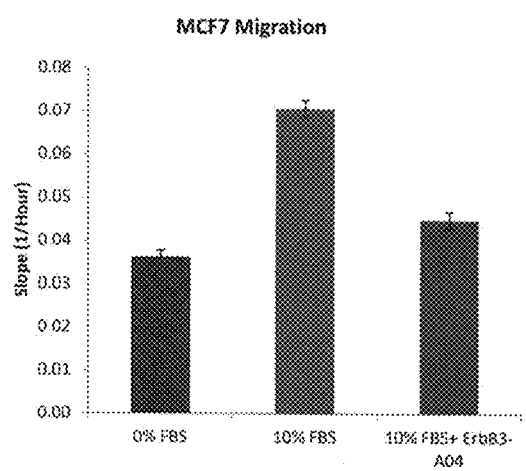
FIG. 9 shows the ability of ErbB3-A04 antibody to inhibit MCF7 migration. Data were measured using non-invasive real-time Impedance measurements with an xCELLigence RTCA MP system (Roche).

This example illustrates the ability of anti-ErbB3 antibodies to inhibit Her3 dependent cell migration. Migration assays were set up using CIM-16 plates with 8 μm pore membranes according to manufacturer's protocol (Roche). Wells were coated with 30 μl gelatin 0.1% in $H_2O$ (EMD Millipore) on each side. Meanwhile, MCF7 cells were starved in serum-free media for 4H. Then the wells of the bottom chambers were filled with 160 μL of serum-free media supplemented or not with 10% serum. The top and bottom portions of the CIM-16 plates were assembled together, and the assembled CIM-16 plate was allowed to equilibrate for 1 hour at 37° C. after the addition of 30 μL of serum-free media to the top chamber wells. Cells were harvested with cell dissociation buffer, resuspended in serum-free media and 40,000 cells were added to each well, in presence or not of 10 μg/ml antibody. After incubation at room temperature for 30 min, CIP-16 plates were placed into the xCELLigence RTCA MP system and data collection started. Impedance values (reported as cell index values) were collected every 15 min for 20 hours. The slopes of the curves thus generated for each condition were plotted using the xCELLigence and EXCEL softwares. Results, shown in FIG. 9, illustrate that an exemplary antibody, A04, efficiently inhibited MCF7 migration.

Example 10

This example illustrates in vitro data showing the inhibition of FBS- and Heregulin-stimulated cell proliferation by a combination of anti-ErbB3 and anti-EGFR antibodies. In this example, 2,000 A431NS adenocarcinoma cells were plated into each well of a 96-well cell culture plate in complete culture media. After 24 hr, media was removed, and cells were incubated with various concentrations of antibodies in DMEM+0.5% FBS for 45 min, followed by addition of NRG1-beta 1 to a final concentration of 25 ng/ml. Cells were incubated for 72 hr at 37° C., after which the Promega Cell Titer 96 Non-radioactive Cell Proliferation (MTT) Assay kit was used to evaluate cell proliferation, as recommended by manufacturer's protocol. Proliferation was expressed in Relative Luminescence Units (RLU) and data were analyzed using Graphpad Prism software using non-linear regression fit.

Figure 10:
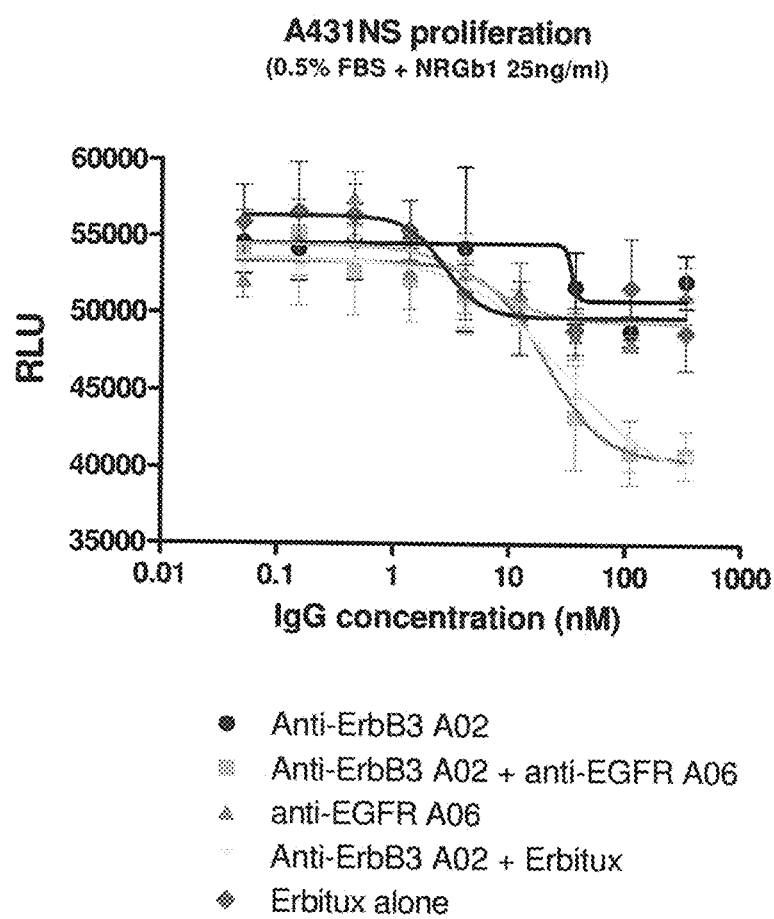
FIG. 10 shows a synergetic inhibitory effect observed when exemplary anti-ErbB3 and anti-EGFR antibodies are used in combination in an assay measuring A431NS proliferation.

Results are shown in FIG. 10. A431NS cells are carcinoma cell line aggressively proliferation under [0.5% FBS+NRGB1] stimulation. Individually, anti-EGFR (A06 or Erbitux) and anti-Her3 IgGs (A02) have only a modest inhibitory effect on A431NS proliferation. However when combined, anti-EGFR and anti-Her3 IgG show robust dose-dependent inhibition of cell proliferation.

Example 11

This example illustrates in vitro data showing the inhibition of FBS- and/or Heregulin-mediated activation of the ErbB family pathways, by a combination of anti-ErbB3 antibody with either anti-EGFR or anti-Her2 antibodies.

Approximately, 20,000 A431NS cells were plated in the wells of a 96-well cell culture cluster in 100 µl Phenol Red-free DMEM media supplemented with 10% FBS. Cells were then starved for 20 hr in 100 µl starvation media (Phenol Red-free DMEM+0% FBS). Antibodies were diluted to 20 µg/ml (2× final concentration) in 50 µl serum-free media, then added to the cells after removal of starvation media. After 1 hr incubation, 50 µl of NRG1-beta 1 (5 ng/ml final) or FBS (0.5% final) or both, were added to the cells. After 10 min at 37° C., cells were washed with ice-cold PBS supplemented with $NaVO_4$, and then lyzed in 100 µl of Cell Lysis Buffer (Cell Signaling Technology). Phosphorylation of Akt and MAPK was detected using PathScan® Sandwich ELISA Kits Phospho-Akt1 and phospho-p44/42 MAPK (Cell Signaling Technology #7147 and #7246 respectively) according to manufacturer's protocol, adjusted for half area ELISA plates. The effect of antibody was determined by measuring the $OD_{450}$ using a SpectraMax plate reader and analyzed using GraphPad Prism 5 software.

Figure 11A:
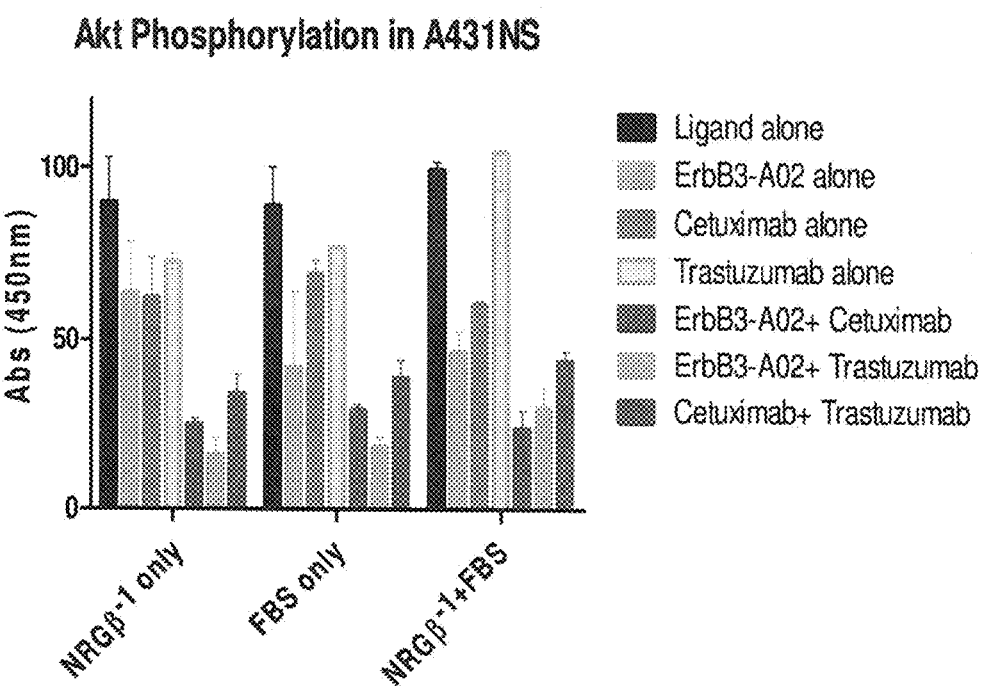
FIG. 11 shows the synergetic inhibitory effect observed when exemplary anti-ErbB3 and either anti-EGFR or anti-Her2 antibodies are used in combination in an assay measuring a) MAPK phosphorylation and b) Akt phosphorylation in A431NS, following different stimulations (NRGb1 only, FBS only, or NRGb1+FBS).
Figure 11B:
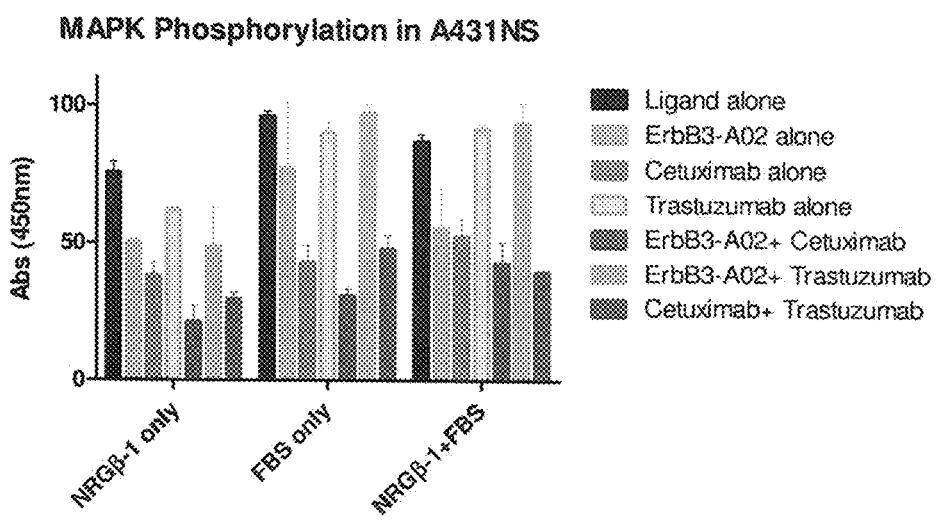

The results are shown in FIG. 11. NRG-beta-1 mostly activates ErbB3 receptor, whereas FBS, which contains EGF but not NRG-beta-1, is believe to stimulate EGFR predominantly. Her2 receptor does not have any known ligand, but is known to interact with both EGFR and ErbB3 upon their activation. Data in FIG. 11 show that individually, anti-ErbB3 A02, anti-EGFR Cetuximab, and anti-Her2 Trastuzumab, all showed relative inhibition of both MAPk and Akt phosphorylation. Most importantly, synergetic effect was observed when combined in pairs. For example, robust inhibition of MAPK phosphorylation was observed when anti-ErbB3 antibodies A02 and Cetuximab were combined, whereas combination of anti-ErbB3 and anti-Her2 Trastuzumab predominantly inhibited Akt phosphorylation. These data illustrate the potential in targeting different receptors involved in the same signaling cascade.

```
                           Sequence Listing

Heavy chain variable domain region    Light chain variable domain region

A01   QVQLVQSGAEVKQPGASVKVSCKASGGTFSSYAIS     QSALTQPPSASGSPGQSVTISCTGTSSDVGA
      WVRQAPGQGLEWMGGIIPIFGTANYAQKFQGRVT      YNDVSWYQHHPGKAPKLIIYEVNHRPSGVP
      ITADESTSTAYMELSSLRSEDTAVYYCATTTMVRGVI   DRFSGSKSDNTASLTISGLQAEDEADYYCSS
      MYYFDYWGQGTLVTVSS SEQ ID NO. 1          YTPSNTPLVFGSGTKVTVL SEQ ID NO. 2

A02   EVQLVQSGAEVKKPGASVTVSCKPSGYAFTDYYIHW    QPVLTQPPSVSAAPGQRVTISCSGSSSNIGN
      VRQAAGQGLEWMGWVDPRSGATVYAQNFQGRV        NYLSWYQQLPGTAPKLLIYDDTKRPSGIPDR
      TMTRDRSSSTVYMDLSRVTSDDTALYFCGRDNYGIF    FSGSKSGTSATLGITGLQTGDEADYYCGTW
      DYWGQGTLVTVSS SEQ ID NO. 3              DGSLDAEVFGTGTKLTVL SEQ ID NO. 4

A04   QVQLQQSGPGLVQPSQTLSLTCDISGDSVSSTGAA     QTVVTQAPSVSVAPGQTARITCGGNNIGSK
      WNWIRQSPSRGLEWLGRTYYRSKWYNDYALSVRS      SVHWYQQKPGQAPVLVVYDDSDRPSGIPE
      RITITPDTSKNQFSLQLNSVTPEDTAVYYCVRDGDVG   RFSGSNSGNTATLTISRVEAGDEADYYCQV
      LDAFDIWGQGTMVTVSS SEQ ID NO. 5          WDSTSDHVVFGGGTKVTVL SEQ ID NO. 6

A08   QMQLVQSGADVKKPGASVRVSCKTSGYTFTSYDIN     QSVLTQPPSVSVAPGNTATITCGGDNIGEKT
      WVRQAPGQGLEWMGWMNPDTGNTAYVQKFQG         VHWYQQRPGQAPALVIYYDSDRPSGIPERF
      RVTVTRDTSINTVYMELSGLRSEDTAVYYCAKSGGSS   SGSNSGNTATLTISRVEAGDEADYYCQVWD
      SYDAFDIWGQGTMVTVSS SEQ ID NO. 7         SSSDHVVFGGGTKLTVL SEQ ID NO. 8

A11   QVQLVQSGRGLVQPGRSLRLSCAASGFTFDEYAMH     EIVLTQSPSSLSASVGDRVTITCQASHDISNY
      WVRHAPGKGLEWVAGMSWNGGGIGYADSVKGR        LTWYQHRPGRAPKLLIFDASRLETGVPSRFS
      FTISRDNSKNTLYLQMNSLRAEDTAVYYCAREGAGG    GYGSGKDFTFTISGLQPEDFATYYCQHYADL
      SYPTDAFDIWGQGTTVTVSS SEQ ID NO. 9       PSFGQGTKLEIK SEQ ID NO. 10

A12   EVQLLESGAEVKKPGASMKVSCKASGYPFPSYGISW    QSVLTQPPSVSVAPGKTARITCGGNNIGSKS
      VRQAPGQGLEWMGWINPYNGETNSAQQLQGRV        VHWYQQKPGQAPVLVIYYDSDRPSGIPERF
      TMTTDTSASTAYMELRSLRADDTAVYYCARARTPIA    SGSNSGNTATLTISRVEAGDEADYYCQVWD
      AAWFDPWGQGTLVTVSS SEQ ID NO. 11         SSSDHLVFGTGTKLVT SEQ ID NO. 12

B01   QVQLVESGGGLVQPGGSLRLACAASGFTFSNYEMN     QAGLTQPPSASASPGDSVTLTCTLSSDHSDY
      WVRQAPGKGLEWVATISDDSVYKYYADSVKGRFTI     KVDWYQQRPGKGPRFVMRVGTGGIVGVK
      SRDNSKALFYLQMDSLTFEDTAIYYCARDPGGDSLG    VSNRFSGSKSGNTASLTISGLQAEDEADYYC
      YFQHWGQGTLVTVSS SEQ ID NO. 13           SSYTDSSTLDVVFGGGTKLTVL SEQ ID NO.
                                              14

B03   EVQLVESGGGLVKPGGSLRLSCAASGFTFSRYSMN     SYELMQPPSVSVAPGKTARITCGGNNIGSKS
      WVRQAPGKGLEWVSSISSSSSYIFYADSVKGRFTISR   VHWYQQKPGQAPVLVIYYDSDRPSGIPERF
      DNAKNSLYLQVNSLGAEDTAVYYCARASSEDAFDI     SGSNSGNTATLTISRVEAGDEADYYCQVWD
      WGQGTMVTVSS SEQ ID NO. 15               SSSDHVVFGGGTKVTVL SEQ ID NO. 16

B04   QLVESGGGVVQPGGSLRLSCAASGFNFRAYGMHW      QAGLTQPPSVSVAPGKTARITCGGDNIGSKS
      VRQAPGKGLEWLAMMSSDGTRTYYADSVKGRFTIS     VHWYQQKPGQAPVLVIYYDTDRPSGIPERF
      RDNSKNTLYVQMNSLRAEDTAVYYCARDRGSFSSS     SGSNSGNTATLTISRVEAGDEADYYCQVWD
      FDLWGQGTLVTVSS SEQ ID NO. 17            SSSDPVVFGGGTKLTVL SEQ ID NO. 18
```

Sequence Listing

| Heavy chain variable domain region | Light chain variable domain region |
|---|---|
| B05 EVQLLESGGGLVQPGGSLRLSCAASGFTFSTYWMT WVRQAPGKGLEWVASMNQDGSEKYYVDSVKGRF TISRDNAKNSLYLQMNSLRDEDTALYYCAKAYSSSW LLSGGMDVWGQGTTVTVSS SEQ ID NO. 19 | QSVVTQPPSVSGAPGQRVTISCTGSSSNIGA GYEVHWYQHVPGTAPKLLIYINSNRPSGIPN RFSGSKSGNTAFLTISGLQAEDEADYYCISYT SSNTWVFGGXTKVTVL SEQ ID NO. 20 |
| B08 QVQLVQSGAEVKKPGASVKVSCKASGYTFTSHYGIS WVRQAPGQGLEWMGSITPHNGKTNYVQMFQGR VTMTTDTSTRTVYMELRNLRSDDTAVYYCARDWN FADFDYWGQGTLVTVSS SEQ ID NO 21 | QSVLTQPPSASGSPGQSVTISCTGTSSDVGG YNFVSWYQQHPGKAPKLMIYDVTNRPSGV SNRFSGSKSGNTASLTISGLAEDEADYYCS SYTSSSTPYVFGTGTKLTVL SEQ ID NO. 22 |
| B10 QVQLVESGGGLVKPGGSLRLSCAASGFTFSSYSMN WVRQAPGKGLEWVSSISSRSGYIYYADSVKGRFTISR DNAKNSLYLQMNSLRDEDTAVYYCVRDGGTVDAF DIWGQGTMVTVSS SEQ ID NO. 23 | QPVLTQPPSVSVAPGKTARITCGGNNIGSKS VHWYQQKPGQAPVLVIYYDSDRPSGIPERF SGSNSGNTATLTISRVEAGDEADYYCQVWD SSSDHVVFGGGTKLTVL SEQ ID NO. 24 |
| B11 QVQLVQSGRGLVQPGRSLRLSCAASGFTFDEYAMH WVRHAPGKGLEWVAGMSWNGGGIGYADSVKGR FTISRDNSKNTLYLQMNSLRAEDTAVYYCAREGAGG SYPTDAFDIWGQGTTVTVSS SEQ ID NO. 25 | EIVLTQSPSSLSASVGDRVTITCQASHDISNY LTWYQHRPGRAPKLLIFDASRLETGVPSRFS GYGSGKDFTFTISGLQPEDFATYYCQHYADL PSFGQGTKVDIK SEQ ID NO. 26 |
| C03 QVQLVQSGAEVKKPGASVKVSCKASGYTFTSYGISW VRQAPGQGLEWMGWISAYNGNTNYAQKLQGRVT MTTDTSTSTAYMELRSLRSDDTAVYYCAREAYAWG AFDIWGQGTMVTVSS SEQ ID NO 27 | SYELMQPPSVSVAPGKTARITCGGNNIGSKS VHWYQQKPGQAPVLVIYYDSDRPSGIPERF SGSNSGNTATLTISRVEAGDEADYYCQVWD SSSRDHAVFGGGTKLTVL SEQ ID NO. 28 |
| C07 QVQLQQSGPGLVQPSQTLSLTCDISGDSVSSTGAA WNWIRQSPSRGLEWLGRTYYRSKWYNDYALSVRS RITITPDTSKNQFSLQLNSVTPEDTAVYYCVRDGDVG LDAFDIWGQGTMVTVSS SEQ ID NO 29 | QAVVTQPPSVSVAPGQTARITCAGNNIGSK SVHWYQQKPGQAPVLVIFDDSDRPSGISER FSGSNSGNTATLTISRVEAGDEADYYCQVW DGDTDHVVFGGGTKLTVL SEQ ID NO. 30 |
| C10 QVQLQQWGAGLLKSSETLSLSCAVYGGTFRDDHW SWIRQPPGKGLEWIGESHHTGRTIYNPSLRSRVTMS IDTSKNEFSLILRSVTAADTATYFCARGNNYVWGNQ EDFWGQGTLVTVSS SEQ ID NO 31 | QPVLTQPASVSGSPGQSITISCTGTSSDVGG YNYVSWYQQHPGKAPKLMIYDVSKRPSGV SNRFSGSKSGNTASLTISGLAEDEADYYCS SYTSNSIYVFGTGTKVTVLG SEQ ID NO. 32 |
| C12 QLVQSGAEVRKPGASVKVSCKASGYTFADYYIHWV RQAPGQGLEWMGWINPNSGGADYAQKLQGRVT MTTDTSTSTAYMELRSLRSDDTAVYYCAREGYAWG AFDIWGQGTMVTVSS SEQ ID NO 33 | QSVVTQPPSVSAAPGQKVTISCSGSSSNIGN NYVSWYQQLPGTAPKLLIYDNNERPSGIPD RFSGSKSGTSATLGITGLQTGDEADYYCGT WDSSLSAGVFGGGTKLTVL SEQ ID NO. 34 |
| D01 EVQLVQSGAEVRKPGASVKVSCKASGYTFTNYHIH WVRQVPGQGLEWMAMINPSNGNTNYGQRFQDR VTLTRDTSTSTAYMELSSLRSEDTAVYLCARDGLTFG DLLAYWGQGTLVTVSS SEQ ID NO 35 | QSVLTQPPSASGTPGQSVTISCSGSSSNIGG NTVNWYQQFPGTAPKLLMYINNLRPAGVP DRFSGSKSGTSASLVISGLQSEDEADYYCAS WDDSLSGLVFGGGTKLTVL SEQ ID NO. 36 |
| D03 QVQLVESGGGLVKPGGSLRLSCAASGFTFSSYSMN WVRQAPGKGLEWVSSISSSSSYIYYADSVKGRFTISR DNSKNTLYLQMNSLRDEDTAVYYCAREILTGYYPDA FDMWGQGTMVTVSS SEQ ID NO 37 | SYELMQPPSVSVAPGKTARITCGGNNIGSKS VHWYQQKPGQAPVVVIYYDSDRPSGIPERF SGSNSGNTATLTISRVEAGDEADYYCQVWD SSSDHYVFGTGTKLTVL SEQ ID NO. 38 |
| D04 EVQLLESGGGLVKPGGSLRLSCAASGFTFSSYSMNW VRQAPGKGLEWVSSISSSSSYIYYADSVKGRFTISRD NAKNSLYLQMNSLRAEDTAVYYCARGFGEDLFDYW GQGTLVTVSS SEQ ID NO 39 | QSVLTQPPSVSVAPGKTARITCGGNNIGSKS VHWYQQKPGQAPLLVIYYDTDRPSGIPERF SGSNSENTATLTISGVEAGDEADYYCQVWD IGSDQVFGTGTKVTVL SEQ ID NO. 40 |
| D07 QVQLVESGGGLVQPGGSLRLSCVASGFTFSSYWMS WVRQAPGKGLEWVAYINLDGSEKDYVDSVKGRFT! SRDNAKNSLYLQMNSLRAEDTALYYCAKAYSSSWLL SGGMDVWGQGTTVTVSS SEQ ID NO 41 | SYELTQPASVSGSPGQSITISCTGTSSDVGNY NSVSWYQQHPGKAPELMIYDVNNRPSGVS NRFSGSKSGNTASLTISGLQAEDEADYYCSS YTSSSTLVFGGGTQLTVLG SEQ ID NO. 42 |
| D08 QVQLVESGGGLVKPGGSLRLSCAASGFTSSSYVLNW VRQAPGKGLEWVSSISSRGSYIYYADSVKGRFTISRD NAKNSLYLQMNSLRAEDTAVYYCARERAGFSPVNA FDIWGQGTMVTVSS SEQ ID NO 43 | QSVLTQPASVSGSPGQSITISCTGSSSDVGSY NLVSWYQQHPGKAPKLMIYDDNRRPSGIST RFSGSKSGNTASLTVSGLQAEDEAYYYCSSY AGRNNDVIFGGGTQLTVL SEQ ID NO. 44 |
| D10 QVQLVESGGGLVQPGGSLRLACAASGFTFSNYEMN WVRQAPGKGLEWVATISDDSVYKYYADSVKGRFT! SRDNSKALFYLQMDSLTFEDTAIYYCARDPGGDSLG YFQHWGQGTLVTVSS SEQ ID NO 45 | QAGLTQPPSASASPGDSVTLTCTLSSDHSDY KVDWYQQRPGKGPRFVMRVGTGGIVGVK GDGIPDRFSVWGSGPNRYLTIKNIQEEDESD YHCGSDHGSGNNYVYVFGGGTKLTVL SEQ ID NO. 46 |

| Heavy chain variable domain region | Light chain variable domain region |
|---|---|
| D11 QVQLQQWGAGLLKPSETLXXTCAVYGGSFSGYYWS WIRQPPGKGLEWIGEINHSGSTNYNPSLKSRVTISV DTSKNQFSLQLNSVTPEDTAVYYCVRDDGMGLDAL DIWGQGTMVTVSS SEQ ID NO 47 | QSALTQPPSVSAAPGQKVTISCSGSSSNIGN NYVSWYQQLPGTAPKLLIYDNNKRPSGIPD RFSGSKSGTSATLGITGLQTGDEADYYCGT WDSSLSAEVFGGGTKVTVL SEQ ID NO. 48 |
| E04 EVQLVQSGAEVKKPGESLKISCKGSGYSFTNYWIGW VRQMPGKGLEWMGIIYPGDSDTRYSPSFQGQVTIS ADKSISTAYLQWSSLKASDTAMYYCAGGGYYSYWG QGTLVTVSS SEQ ID NO 49 | LPVLTQPPSASGSPGQSVTISCTGTSSDVGG YNYVSWYQQHPGKAPKLMIYEVSKRPSGV PDRFSGSKSGNTASLTVSGLQAEDEADYYCS SYAGSNNPYVFGTGTKVTVL SEQ ID NO. 50 |
| E05 QVQLVESGGGLIQPGGSVKLSCAASGFTVSSNYMS WVRQAPGKGLEWVAVISYDGSFEYYGESVKGRFTIS RDNAKNTLYLQMSSLRPEDTAVYYCAKDTPYYYDSS GQSGDYFDHWGQGALVTVSS SEQ ID NO 51 | QSVLTQPPSVSGAPGQRVTISCTGSSSNIGA GYDVHWYQQLPGTAPKLLIYGNSNRPSGVP DRFSGSKSGNTASLTVSGLQAEDEADYYCAS WDDSLNSPVFGGGTKLTVL SEQ ID NO. 52 |
| E08 EVQLVESGGGLIQPGGSLRLSCAASGFTVSSNYMS WVRQAPGKGLEWVSVIYSGGSTYYADSVKGRFTISR DNSKNTLYLQMNSLRAEDTAVYYCARDFGVGAVDY WGQGTLVTVSS SEQ ID NO 53 | QSVLTQPASVSGSPGQSITISCTGTSSDVGG YNFVSWYQQHPGKAPKLMIYDVTNRPSGV SNRFSGSKSGNTASLTISGLQAEDEADYYCS SYTDSSTLDVVFGGGTKVTVL SEQ ID NO. 54 |
| F10 QLQLQESGPGLVKPSQTLSLTCTVSGGSINSAGYYW TWIRQHPGKGLEWIGSIYYSGSTYYNPSLKSRVSMS QDTSKNQFSLKLSSLTAADTAVYYCAREVGVVPEYM DVWGQGTTVTVSS SEQ ID NO 55 | QSALTQPASVSGSPGQSITISCTGTTSDVGG YNYVSWYQQHPGKGPKLMIYDVSKRPSGV SGRFSGSKSGNTASLTISGLQAEDEADYYCS SYTSSSTLLFGGXTKLTVL SEQ ID NO. 56 |
| G01 QVQLVESGGGLVQPGRSLRLSCAASGFTFSSYGMH WVRQAPGKGLEWVGFIRSETYGGTTQTAASVKGRF SISRDDSQGIAYLQMDSLKTEDTAVYFCARSGRGDF WGQGTLVTVSS SEQ ID NO 57 | QAGLTQPRSVSGSPGQSVTISCTGTSSDVG GYNYVSWYQQHPGKAPKLLIYDVNNRPSG VPDRFSGSKSGNTASLTISGLQAEDEADYYC SSYTSSTTQVFGGGTKVTVL SEQ ID NO. 58 |
| H06 QVQLQESGGGVVQPGRSLXLSCAASGFTFSSYAMH WVRQAPGKGLEWVAVISYDGSNKYYADSVKGRFTI SRDNSKNTLYLQMNSLRAEDTAVYYCARDRWDVA STVEATDGMDVWGQGTTVTVSS SEQ ID NO 59 | QAGLTQPPSASGSPGQSVTISCTGTSSDVG GYNYVSWYQQHPGKAPKLMIYEVNKRPSG IPDRFSGSKSDSTASLTISGLQAEDEANYYCIS YTSSTTWVFGGGTQLTVL SEQ ID NO. 60 |

We claim:

1. A recombinant anti-ErbB3 antibody comprising a heavy chain variable domain having an amino acid sequence selected from the group consisting of SEQ ID NO. 3, SEQ ID NO. 5, and SEQ ID NO. 7, and comprising a light chain variable domain having an amino acid sequence selected from the group consisting of SEQ ID NO. 4, SEQ ID NO. 6 and SEQ ID. NO. 8, wherein the antibody is an IgG.

2. The recombinant fully human antibody of claim 1, wherein the heavy chain variable domain has an amino acid sequence as set forth in SEQ ID NO: 3, and the light chain variable domain has an amino acid sequence as set forth in SEQ ID NO: 4.

3. The recombinant fully human antibody of claim 1, wherein the heavy chain variable domain has an amino acid sequence as set forth in SEQ ID NO: 5, and the light chain variable domain has an amino acid sequence as set forth in SEQ ID NO: 6.

4. The recombinant fully human antibody of claim 1, wherein the heavy chain variable domain has an amino acid sequence as set forth in SEQ ID NO: 7, and the light chain variable domain has an amino acid sequence as set forth in SEQ ID NO: 8.

* * * * *

SEQUENCE LISTING

<160> NUMBER OF SEQ ID NOS: 60

<210> SEQ ID NO 1
<211> LENGTH: 123
<212> TYPE: PRT
<213> ORGANISM: Homo sapiens

<400> SEQUENCE: 1

Gln Val Gln Leu Val Gln Ser Gly Ala Glu Val Lys Gln Pro Gly Ala
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Thr Thr Thr Met Val Arg Gly Val Ile Met Tyr Tyr Phe Asp Tyr
            100                 105                 110

```
Trp Gly Gln Gly Thr Leu Val Thr Val Ser Ser
        115                 120
```

```
<210> SEQ ID NO 2
<211> LENGTH: 111
<212> TYPE: PRT
<213> ORGANISM: Homo sapiens

<400> SEQUENCE: 2
```

```
Gln Ser Ala Leu Thr Gln Pro Pro Ser Ala Ser Gly Ser Pro Gly Gln
1               5                   10                  15

Ser Val Thr Ile Ser Cys Thr Gly Thr Ser Ser Asp Val Gly Ala Tyr
            20                  25                  30

Asn Asp Val Ser Trp Tyr Gln His Pro Gly Lys Ala Pro Lys Leu
        35                  40                  45

Ile Ile Tyr Glu Val Asn His Arg Pro Ser Gly Val Pro Asp Arg Phe
    50                  55                  60

Ser Gly Ser Lys Ser Asp Asn Thr Ala Ser Leu Thr Ile Ser Gly Leu
65                  70                  75                  80

Gln Ala Glu Asp Glu Ala Asp Tyr Tyr Cys Ser Ser Tyr Thr Pro Ser
                85                  90                  95

Asn Thr Pro Leu Val Phe Gly Ser Gly Thr Lys Val Thr Val Leu
            100                 105                 110
```

```
<210> SEQ ID NO 3
<211> LENGTH: 117
<212> TYPE: PRT
<213> ORGANISM: Homo sapiens

<400> SEQUENCE: 3
```

```
Glu Val Gln Leu Val Gln Ser Gly Ala Glu Val Lys Lys Pro Gly Ala
1               5                   10                  15

Ser Val Thr Val Ser Cys Lys Pro Ser Gly Tyr Ala Phe Thr Asp Tyr
            20                  25                  30

Tyr Ile His Trp Val Arg Gln Ala Ala Gly Gln Gly Leu Glu Trp Met
        35                  40                  45

Gly Trp Val Asp Pro Arg Ser Gly Ala Thr Val Tyr Ala Gln Asn Phe
    50                  55                  60

Gln Gly Arg Val Thr Met Thr Arg Asp Arg Ser Ser Ser Thr Val Tyr
65                  70                  75                  80

Met Asp Leu Ser Arg Val Thr Ser Asp Thr Ala Leu Tyr Phe Cys
                85                  90                  95

Gly Arg Asp Asn Tyr Gly Ile Phe Asp Tyr Trp Gly Gln Gly Thr Leu
            100                 105                 110

Val Thr Val Ser Ser
        115
```

```
<210> SEQ ID NO 4
<211> LENGTH: 110
<212> TYPE: PRT
<213> ORGANISM: Homo sapiens

<400> SEQUENCE: 4
```

```
Gln Pro Val Leu Thr Gln Pro Pro Ser Val Ser Ala Ala Pro Gly Gln
1               5                   10                  15

Arg Val Thr Ile Ser Cys Ser Gly Ser Ser Ser Asn Ile Gly Asn Asn
            20                  25                  30
```

```
Tyr Leu Ser Trp Tyr Gln Gln Leu Pro Gly Thr Ala Pro Lys Leu Leu
         35                  40                  45

Ile Tyr Asp Asp Thr Lys Arg Pro Ser Gly Ile Pro Asp Arg Phe Ser
 50                  55                  60

Gly Ser Lys Ser Gly Thr Ser Ala Thr Leu Gly Ile Thr Gly Leu Gln
 65                  70                  75                  80

Thr Gly Asp Glu Ala Asp Tyr Tyr Cys Gly Thr Trp Asp Gly Ser Leu
                 85                  90                  95

Asp Ala Glu Val Phe Gly Thr Gly Thr Lys Leu Thr Val Leu
            100                 105                 110

<210> SEQ ID NO 5
<211> LENGTH: 123
<212> TYPE: PRT
<213> ORGANISM: Homo sapiens

<400> SEQUENCE: 5

Gln Val Gln Leu Gln Gln Ser Gly Pro Gly Leu Val Gln Pro Ser Gln
 1               5                  10                  15

Thr Leu Ser Leu Thr Cys Asp Ile Ser Gly Asp Ser Val Ser Ser Thr
            20                  25                  30

Gly Ala Ala Trp Asn Trp Ile Arg Gln Ser Pro Ser Arg Gly Leu Glu
         35                  40                  45

Trp Leu Gly Arg Thr Tyr Tyr Arg Ser Lys Trp Tyr Asn Asp Tyr Ala
 50                  55                  60

Leu Ser Val Arg Ser Arg Ile Thr Ile Thr Pro Asp Thr Ser Lys Asn
 65                  70                  75                  80

Gln Phe Ser Leu Gln Leu Asn Ser Val Thr Pro Glu Asp Thr Ala Val
                 85                  90                  95

Tyr Tyr Cys Val Arg Asp Gly Asp Val Gly Leu Asp Ala Phe Asp Ile
            100                 105                 110

Trp Gly Gln Gly Thr Met Val Thr Val Ser Ser
        115                 120

<210> SEQ ID NO 6
<211> LENGTH: 108
<212> TYPE: PRT
<213> ORGANISM: Homo sapiens

<400> SEQUENCE: 6

Gln Thr Val Val Thr Gln Ala Pro Ser Val Ser Val Ala Pro Gly Gln
 1               5                  10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Val Tyr
         35                  40                  45

Asp Asp Ser Asp Arg Pro Ser Gly Ile Pro Glu Arg Phe Ser Gly Ser
 50                  55                  60

Asn Ser Gly Asn Thr Ala Thr Leu Thr Ile Ser Arg Val Glu Ala Gly
 65                  70                  75                  80

Asp Glu Ala Asp Tyr Tyr Cys Gln Val Trp Asp Ser Thr Ser Asp His
                 85                  90                  95

Val Val Phe Gly Gly Gly Thr Lys Val Thr Val Leu
            100                 105

<210> SEQ ID NO 7
<211> LENGTH: 121
```

<212> TYPE: PRT
<213> ORGANISM: Homo sapiens

<400> SEQUENCE: 7

Gln Met Gln Leu Val Gln Ser Gly Ala Asp Val Lys Pro Gly Ala
1               5                   10                  15

Ser Val Arg Val Ser Cys Lys Thr Ser Gly Tyr Thr Phe Thr Ser Tyr
            20                  25                  30

Asp Ile Asn Trp Val Arg Gln Ala Pro Gly Gln Gly Leu Glu Trp Met
        35                  40                  45

Gly Trp Met Asn Pro Asp Thr Gly Asn Thr Ala Tyr Val Gln Lys Phe
    50                  55                  60

Gln Gly Arg Val Thr Val Thr Arg Asp Thr Ser Ile Asn Thr Val Tyr
65                  70                  75                  80

Met Glu Leu Ser Gly Leu Arg Ser Glu Asp Thr Ala Val Tyr Tyr Cys
                85                  90                  95

Ala Lys Ser Gly Gly Ser Ser Tyr Asp Ala Phe Asp Ile Trp Gly
            100                 105                 110

Gln Gly Thr Met Val Thr Val Ser Ser
        115                 120

<210> SEQ ID NO 8
<211> LENGTH: 108
<212> TYPE: PRT
<213> ORGANISM: Homo sapiens

<400> SEQUENCE: 8

Gln Ser Val Leu Thr Gln Pro Pro Ser Val Ser Val Ala Pro Gly Asn
1               5                   10                  15

Thr Ala Thr Ile Thr Cys Gly Gly Asp Asn Ile Gly Glu Lys Thr Val
            20                  25                  30

His Trp Tyr Gln Gln Arg Pro Gly Gln Ala Pro Ala Leu Val Ile Tyr
        35                  40                  45

Tyr Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Val Val Phe Gly Gly Gly Thr Lys Leu Thr Val Leu
            100                 105

<210> SEQ ID NO 9
<211> LENGTH: 123
<212> TYPE: PRT
<213> ORGANISM: Homo sapiens

<400> SEQUENCE: 9

Gln Val Gln Leu Val Gln Ser Gly Arg Gly Leu Val Gln Pro Gly Arg
1               5                   10                  15

Ser Leu Arg Leu Ser Cys Ala Ala Ser Gly Phe Thr Phe Asp Glu Tyr
            20                  25                  30

Ala Met His Trp Val Arg His Ala Pro Gly Lys Gly Leu Glu Trp Val
        35                  40                  45

Ala Gly Met Ser Trp Asn Gly Gly Ile Gly Tyr Ala Asp Ser Val
    50                  55                  60

Lys Gly Arg Phe Thr Ile Ser Arg Asp Asn Ser Lys Asn Thr Leu Tyr

```
              65                  70                  75                  80
Leu Gln Met Asn Ser Leu Arg Ala Glu Asp Thr Ala Val Tyr Tyr Cys
                    85                  90                  95

Ala Arg Glu Gly Ala Gly Gly Ser Tyr Pro Thr Asp Ala Phe Asp Ile
                100                 105                 110

Trp Gly Gln Gly Thr Thr Val Thr Val Ser Ser
                115                 120
```

<210> SEQ ID NO 10
<211> LENGTH: 105
<212> TYPE: PRT
<213> ORGANISM: Homo sapiens

<400> SEQUENCE: 10

```
Ile Val Leu Thr Gln Ser Pro Ser Ser Leu Ser Ala Ser Val Gly Asp
1               5                   10                  15

Arg Val Thr Ile Thr Cys Gln Ala Ser His Asp Ile Ser Asn Tyr Leu
                20                  25                  30

Thr Trp Tyr Gln His Arg Pro Gly Arg Ala Pro Lys Leu Leu Ile Phe
                35                  40                  45

Asp Ala Ser Arg Leu Glu Thr Gly Val Pro Ser Arg Phe Ser Gly Tyr
                50                  55                  60

Gly Ser Gly Lys Asp Phe Thr Phe Thr Ile Ser Gly Leu Gln Pro Glu
65                  70                  75                  80

Asp Phe Ala Thr Tyr Tyr Cys Gln His Tyr Ala Asp Leu Pro Ser Phe
                85                  90                  95

Gly Gln Gly Thr Lys Leu Glu Ile Lys
                100                 105
```

<210> SEQ ID NO 11
<211> LENGTH: 120
<212> TYPE: PRT
<213> ORGANISM: Homo sapiens

<400> SEQUENCE: 11

```
Val Gln Leu Leu Glu Ser Gly Ala Glu Val Lys Lys Pro Gly Ala Ser
1               5                   10                  15

Met Lys Val Ser Cys Lys Ala Ser Gly Tyr Pro Phe Pro Ser Tyr Gly
                20                  25                  30

Ile Ser Trp Val Arg Gln Ala Pro Gly Gln Gly Leu Glu Trp Met Gly
                35                  40                  45

Trp Ile Asn Pro Tyr Asn Gly Glu Thr Asn Ser Ala Gln Gln Leu Gln
                50                  55                  60

Gly Arg Val Thr Met Thr Thr Asp Thr Ser Ala Ser Thr Ala Tyr Met
65                  70                  75                  80

Glu Leu Arg Ser Leu Arg Ala Asp Asp Thr Ala Val Tyr Tyr Cys Ala
                85                  90                  95

Arg Ala Arg Thr Pro Ile Ala Ala Ala Trp Phe Asp Pro Trp Gly Gln
                100                 105                 110

Gly Thr Leu Val Thr Val Ser Ser
                115                 120
```

<210> SEQ ID NO 12
<211> LENGTH: 107
<212> TYPE: PRT
<213> ORGANISM: Homo sapiens

<400> SEQUENCE: 12

Gln Ser Val Leu Thr Gln Pro Pro Ser Val Ser Val Ala Pro Gly Lys
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Ile Tyr
            35                  40                  45

Tyr Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Leu Val Phe Gly Thr Gly Thr Lys Leu Val Thr
            100                 105

<210> SEQ ID NO 13
<211> LENGTH: 121
<212> TYPE: PRT
<213> ORGANISM: Homo sapiens

<400> SEQUENCE: 13

Gln Val Gln Leu Val Glu Ser Gly Gly Gly Leu Val Gln Pro Gly Gly
1               5                   10                  15

Ser Leu Arg Leu Ala Cys Ala Ala Ser Gly Phe Thr Phe Ser Asn Tyr
            20                  25                  30

Glu Met Asn Trp Val Arg Gln Ala Pro Gly Lys Gly Leu Glu Trp Val
            35                  40                  45

Ala Thr Ile Ser Asp Asp Ser Val Tyr Lys Tyr Tyr Ala Asp Ser Val
    50                  55                  60

Lys Gly Arg Phe Thr Ile Ser Arg Asp Asn Ser Lys Ala Leu Phe Tyr
65                  70                  75                  80

Leu Gln Met Asp Ser Leu Thr Phe Glu Asp Thr Ala Ile Tyr Tyr Cys
                85                  90                  95

Ala Arg Asp Pro Gly Gly Asp Ser Leu Gly Tyr Phe Gln His Trp Gly
            100                 105                 110

Gln Gly Thr Leu Val Thr Val Ser Ser
            115                 120

<210> SEQ ID NO 14
<211> LENGTH: 112
<212> TYPE: PRT
<213> ORGANISM: Homo sapiens

<400> SEQUENCE: 14

Gln Ala Gly Leu Thr Gln Pro Pro Ser Ala Ser Ala Ser Pro Gly Asp
1               5                   10                  15

Ser Val Thr Leu Thr Cys Thr Leu Ser Ser Asp His Ser Asp Tyr Lys
            20                  25                  30

Val Asp Trp Tyr Gln Gln Arg Pro Gly Lys Gly Pro Arg Phe Val Met
            35                  40                  45

Arg Val Gly Thr Gly Gly Ile Val Gly Val Lys Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Asp Ser
                85                  90                  95

Ser Thr Leu Asp Val Val Phe Gly Gly Gly Thr Lys Leu Thr Val Leu
            100                 105                 110

<210> SEQ ID NO 15
<211> LENGTH: 118
<212> TYPE: PRT
<213> ORGANISM: Homo sapiens

<400> SEQUENCE: 15

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Arg Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Tyr Ile Phe Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Val Asn Ser Leu Gly Ala Glu Asp Thr Ala Val Tyr Tyr Cys
                85                  90                  95

Ala Arg Ala Ser Ser Glu Asp Ala Phe Asp Ile Trp Gly Gln Gly Thr
            100                 105                 110

Met Val Thr Val Ser Ser
            115

<210> SEQ ID NO 16
<211> LENGTH: 108
<212> TYPE: PRT
<213> ORGANISM: Homo sapiens

<400> SEQUENCE: 16

Ser Tyr Glu Leu Met Gln Pro Pro Ser Val Ser Val Ala Pro Gly Lys
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Ile Tyr
        35                  40                  45

Tyr Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Val Val Phe Gly Gly Gly Thr Lys Val Thr Val Leu
            100                 105

<210> SEQ ID NO 17
<211> LENGTH: 118
<212> TYPE: PRT
<213> ORGANISM: Homo sapiens

<400> SEQUENCE: 17

Gln Leu Val Glu Ser Gly Gly Gly Val Val Gln Pro Gly Gly Ser Leu
1               5                   10                  15

Arg Leu Ser Cys Ala Ala Ser Gly Phe Asn Phe Arg Ala Tyr Gly Met
            20                  25                  30

His Trp Val Arg Gln Ala Pro Gly Lys Gly Leu Glu Trp Leu Ala Met
            35                  40                  45

Met Ser Ser Asp Gly Thr Arg Thr Tyr Tyr Ala Asp Ser Val Lys Gly
 50                  55                  60

Arg Phe Thr Ile Ser Arg Asp Asn Ser Lys Asn Thr Leu Tyr Val Gln
65                   70                  75                  80

Met Asn Ser Leu Arg Ala Glu Asp Thr Ala Val Tyr Tyr Cys Ala Arg
                85                  90                  95

Asp Arg Gly Ser Phe Ser Ser Phe Asp Leu Trp Gly Gln Gly Thr
                100                 105                 110

Leu Val Thr Val Ser Ser
            115

<210> SEQ ID NO 18
<211> LENGTH: 108
<212> TYPE: PRT
<213> ORGANISM: Homo sapiens

<400> SEQUENCE: 18

Gln Ala Gly Leu Thr Gln Pro Pro Ser Val Ser Val Ala Pro Gly Lys
1               5                   10                  15

Thr Ala Arg Ile Thr Cys Gly Gly Asp Asn Ile Gly Ser Lys Ser Val
            20                  25                  30

His Trp Tyr Gln Gln Lys Pro Gly Gln Ala Pro Val Leu Val Ile Tyr
            35                  40                  45

Tyr Asp Thr Asp Arg Pro Ser Gly Ile Pro Glu Arg Phe Ser Gly Ser
 50                  55                  60

Asn Ser Gly Asn Thr Ala Thr Leu Thr Ile Ser Arg Val Glu Ala Gly
65                   70                  75                  80

Asp Glu Ala Asp Tyr Tyr Cys Gln Val Trp Asp Ser Ser Ser Asp Pro
                85                  90                  95

Val Val Phe Gly Gly Gly Thr Lys Leu Thr Val Leu
                100                 105

<210> SEQ ID NO 19
<211> LENGTH: 123
<212> TYPE: PRT
<213> ORGANISM: Homo sapiens

<400> SEQUENCE: 19

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Trp Met Thr Trp Val Arg Gln Ala Pro Gly Lys Gly Leu Glu Trp Val
            35                  40                  45

Ala Ser Met Asn Gln Asp Gly Ser Glu Lys Tyr Tyr Val Asp Ser Val
 50                  55                  60

Lys Gly Arg Phe Thr Ile Ser Arg Asp Asn Ala Lys Asn Ser Leu Tyr
65                   70                  75                  80

Leu Gln Met Asn Ser Leu Arg Asp Glu Asp Thr Ala Leu Tyr Tyr Cys
                85                  90                  95

Ala Lys Ala Tyr Ser Ser Ser Trp Leu Leu Ser Gly Gly Met Asp Val
                100                 105                 110

Trp Gly Gln Gly Thr Thr Val Thr Val Ser Ser
            115                 120

```
<210> SEQ ID NO 20
<211> LENGTH: 110
<212> TYPE: PRT
<213> ORGANISM: Homo sapiens
<220> FEATURE:
<221> NAME/KEY: misc_feature
<222> LOCATION: (104)..(104)
<223> OTHER INFORMATION: Xaa can be any naturally occurring amino acid

<400> SEQUENCE: 20

Gln Ser Val Val Thr Gln Pro Pro Ser Val Ser Gly Ala Pro Gly Gln
1               5                   10                  15

Arg Val Thr Ile Ser Cys Thr Gly Ser Ser Asn Ile Gly Ala Gly
            20                  25                  30

Tyr Glu Val His Trp Tyr Gln His Val Pro Gly Thr Ala Pro Lys Leu
        35                  40                  45

Leu Ile Tyr Ile Asn Ser Asn Arg Pro Ser Gly Ile Pro Asn Arg Phe
    50                  55                  60

Ser Gly Ser Lys Ser Gly Asn Thr Ala Phe Leu Thr Ile Ser Gly Leu
65                  70                  75                  80

Gln Ala Glu Asp Glu Ala Asp Tyr Tyr Cys Ile Ser Tyr Thr Ser Ser
                85                  90                  95

Asn Thr Trp Val Phe Gly Gly Xaa Thr Lys Val Thr Val Leu
            100                 105                 110

<210> SEQ ID NO 21
<211> LENGTH: 119
<212> TYPE: PRT
<213> ORGANISM: Homo sapiens

<400> SEQUENCE: 21

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser His
            20                  25                  30

Tyr Gly Ile Ser Trp Val Arg Gln Ala Pro Gly Gln Gly Leu Glu Trp
        35                  40                  45

Met Gly Ser Ile Thr Pro His Asn Gly Lys Thr Asn Tyr Val Gln Met
    50                  55                  60

Phe Gln Gly Arg Val Thr Met Thr Thr Asp Thr Ser Thr Arg Thr Val
65                  70                  75                  80

Tyr Met Glu Leu Arg Asn Leu Arg Ser Asp Asp Thr Ala Val Tyr Tyr
                85                  90                  95

Cys Ala Arg Asp Trp Asn Phe Ala Asp Phe Asp Tyr Trp Gly Gln Gly
            100                 105                 110

Thr Leu Val Thr Val Ser Ser
        115

<210> SEQ ID NO 22
<211> LENGTH: 111
<212> TYPE: PRT
<213> ORGANISM: Homo sapiens

<400> SEQUENCE: 22

Gln Ser Val Leu Thr Gln Pro Pro Ser Ala Ser Gly Ser Pro Gly Gln
1               5                   10                  15

Ser Val Thr Ile Ser Cys Thr Gly Thr Ser Ser Asp Val Gly Gly Tyr
            20                  25                  30
```

```
Asn Phe Val Ser Trp Tyr Gln Gln His Pro Gly Lys Ala Pro Lys Leu
             35                  40                  45

Met Ile Tyr Asp Val Thr Asn Arg Pro Ser Gly Val Ser Asn Arg Phe
 50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Ser Ser Tyr Thr Ser Ser
                 85                  90                  95

Ser Thr Pro Tyr Val Phe Gly Thr Gly Thr Lys Leu Thr Val Leu
                100                 105                 110

<210> SEQ ID NO 23
<211> LENGTH: 119
<212> TYPE: PRT
<213> ORGANISM: Homo sapiens

<400> SEQUENCE: 23

Gln Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Ser Tyr
                20                  25                  30

Ser Met Asn Trp Val Arg Gln Ala Pro Gly Lys Gly Leu Glu Trp Val
             35                  40                  45

Ser Ser Ile Ser Ser Arg Ser Gly Tyr Ile Tyr Tyr Ala Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Asp Glu Asp Thr Ala Val Tyr Tyr Cys
                 85                  90                  95

Val Arg Asp Gly Gly Thr Val Asp Ala Phe Asp Ile Trp Gly Gln Gly
                100                 105                 110

Thr Met Val Thr Val Ser Ser
        115

<210> SEQ ID NO 24
<211> LENGTH: 108
<212> TYPE: PRT
<213> ORGANISM: Homo sapiens

<400> SEQUENCE: 24

Gln Pro Val Leu Thr Gln Pro Pro Ser Val Ser Val Ala Pro Gly Lys
 1               5                  10                  15

Thr Ala Arg Ile Thr Cys Gly Gly Asn Asn Ile Gly Ser Lys Ser Val
                20                  25                  30

His Trp Tyr Gln Gln Lys Pro Gly Gln Ala Pro Val Leu Val Ile Tyr
             35                  40                  45

Tyr Asp Ser Asp Arg Pro Ser Gly Ile Pro Glu Arg Phe Ser Gly Ser
 50                  55                  60

Asn Ser Gly Asn Thr Ala Thr Leu Thr Ile Ser Arg Val Glu Ala Gly
 65                  70                  75                  80

Asp Glu Ala Asp Tyr Tyr Cys Gln Val Trp Asp Ser Ser Ser Asp His
                 85                  90                  95

Val Val Phe Gly Gly Gly Thr Lys Leu Thr Val Leu
                100                 105

<210> SEQ ID NO 25
<211> LENGTH: 123
```

```
<212> TYPE: PRT
<213> ORGANISM: Homo sapiens

<400> SEQUENCE: 25

Gln Val Gln Leu Val Gln Ser Gly Arg Gly Leu Val Gln Pro Gly Arg
 1               5                  10                  15

Ser Leu Arg Leu Ser Cys Ala Ala Ser Gly Phe Thr Phe Asp Glu Tyr
             20                  25                  30

Ala Met His Trp Val Arg His Ala Pro Gly Lys Gly Leu Glu Trp Val
         35                  40                  45

Ala Gly Met Ser Trp Asn Gly Gly Ile Gly Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
             85                  90                  95

Ala Arg Glu Gly Ala Gly Gly Ser Tyr Pro Thr Asp Ala Phe Asp Ile
            100                 105                 110

Trp Gly Gln Gly Thr Thr Val Thr Val Ser Ser
            115                 120

<210> SEQ ID NO 26
<211> LENGTH: 106
<212> TYPE: PRT
<213> ORGANISM: Homo sapiens

<400> SEQUENCE: 26

Glu Ile Val Leu Thr Gln Ser Pro Ser Ser Leu Ser Ala Ser Val Gly
 1               5                  10                  15

Asp Arg Val Thr Ile Thr Cys Gln Ala Ser His Asp Ile Ser Asn Tyr
             20                  25                  30

Leu Thr Trp Tyr Gln His Arg Pro Gly Arg Ala Pro Lys Leu Leu Ile
         35                  40                  45

Phe Asp Ala Ser Arg Leu Glu Thr Gly Val Pro Ser Arg Phe Ser Gly
     50                  55                  60

Tyr Gly Ser Gly Lys Asp Phe Thr Phe Thr Ile Ser Gly Leu Gln Pro
 65                  70                  75                  80

Glu Asp Phe Ala Thr Tyr Tyr Cys Gln His Tyr Ala Asp Leu Pro Ser
             85                  90                  95

Phe Gly Gln Gly Thr Lys Val Asp Ile Lys
            100                 105

<210> SEQ ID NO 27
<211> LENGTH: 119
<212> TYPE: PRT
<213> ORGANISM: Homo sapiens

<400> SEQUENCE: 27

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
             20                  25                  30

Gly Ile Ser Trp Val Arg Gln Ala Pro Gly Gln Gly Leu Glu Trp Met
         35                  40                  45

Gly Trp Ile Ser Ala Tyr Asn Gly Asn Thr Asn Tyr Ala Gln Lys Leu
     50                  55                  60

Gln Gly Arg Val Thr Met Thr Thr Asp Thr Ser Thr Ser Thr Ala Tyr
```

```
            65                  70                  75                  80
Met Glu Leu Arg Ser Leu Arg Ser Asp Asp Thr Ala Val Tyr Tyr Cys
                85                  90                  95

Ala Arg Glu Ala Tyr Ala Trp Gly Ala Phe Asp Ile Trp Gly Gln Gly
            100                 105                 110

Thr Met Val Thr Val Ser Ser
        115

<210> SEQ ID NO 28
<211> LENGTH: 108
<212> TYPE: PRT
<213> ORGANISM: Homo sapiens

<400> SEQUENCE: 28

Ser Tyr Glu Leu Met Gln Pro Pro Ser Val Ser Val Ala Pro Gly Lys
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Ile Tyr
        35                  40                  45

Tyr Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Arg Asp His
                85                  90                  95

Ala Val Phe Gly Gly Gly Thr Lys Leu Thr Val Leu
            100                 105

<210> SEQ ID NO 29
<211> LENGTH: 123
<212> TYPE: PRT
<213> ORGANISM: Homo sapiens

<400> SEQUENCE: 29

Gln Val Gln Leu Gln Gln Ser Gly Pro Gly Leu Val Gln Pro Ser Gln
1               5                   10                  15

Thr Leu Ser Leu Thr Cys Asp Ile Ser Gly Asp Ser Val Ser Ser Thr
            20                  25                  30

Gly Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
    50                  55                  60

Leu Ser Val Arg Ser Arg Ile Thr Ile Thr Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Val Arg Asp Gly Val Gly Leu Asp Ala Phe Asp Ile
            100                 105                 110

Trp Gly Gln Gly Thr Met Val Thr Val Ser Ser
        115                 120

<210> SEQ ID NO 30
<211> LENGTH: 108
<212> TYPE: PRT
<213> ORGANISM: Homo sapiens

<400> SEQUENCE: 30
```

-continued

Gln Ala Val Val Thr Gln Pro Pro Ser Val Ser Val Ala Pro Gly Gln
1               5                   10                  15

Thr Ala Arg Ile Thr Cys Ala Gly Asn Asn Ile Gly Ser Lys Ser Val
            20                  25                  30

His Trp Tyr Gln Gln Lys Pro Gly Gln Ala Pro Val Leu Val Ile Phe
        35                  40                  45

Asp Asp Ser Asp Arg Pro Ser Gly Ile Ser Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Gly Asp Thr Asp His
                85                  90                  95

Val Val Phe Gly Gly Gly Thr Lys Leu Thr Val Leu
            100                 105

<210> SEQ ID NO 31
<211> LENGTH: 120
<212> TYPE: PRT
<213> ORGANISM: Homo sapiens

<400> SEQUENCE: 31

Gln Val Gln Leu Gln Gln Trp Gly Ala Gly Leu Leu Lys Ser Ser Glu
1               5                   10                  15

Thr Leu Ser Leu Ser Cys Ala Val Tyr Gly Gly Thr Phe Arg Asp Asp
            20                  25                  30

His Trp Ser Trp Ile Arg Gln Pro Pro Gly Lys Gly Leu Glu Trp Ile
        35                  40                  45

Gly Glu Ser His His Thr Gly Arg Thr Ile Tyr Asn Pro Ser Leu Arg
    50                  55                  60

Ser Arg Val Thr Met Ser Ile Asp Thr Ser Lys Asn Glu Phe Ser Leu
65                  70                  75                  80

Ile Leu Arg Ser Val Thr Ala Ala Asp Thr Ala Thr Tyr Phe Cys Ala
                85                  90                  95

Arg Gly Asn Asn Tyr Val Trp Gly Asn Gln Glu Asp Phe Trp Gly Gln
            100                 105                 110

Gly Thr Leu Val Thr Val Ser Ser
        115                 120

<210> SEQ ID NO 32
<211> LENGTH: 111
<212> TYPE: PRT
<213> ORGANISM: Homo sapiens

<400> SEQUENCE: 32

Gln Pro Val Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Asn
                85                  90                  95

```
Ser Ile Tyr Val Phe Gly Thr Gly Thr Lys Val Thr Val Leu Gly
                100                 105                 110

<210> SEQ ID NO 33
<211> LENGTH: 117
<212> TYPE: PRT
<213> ORGANISM: Homo sapiens

<400> SEQUENCE: 33

Gln Leu Val Gln Ser Gly Ala Glu Val Arg Lys Pro Gly Ala Ser Val
1               5                   10                  15

Lys Val Ser Cys Lys Ala Ser Gly Tyr Thr Phe Ala Asp Tyr Tyr Ile
            20                  25                  30

His Trp Val Arg Gln Ala Pro Gly Gln Gly Leu Glu Trp Met Gly Trp
        35                  40                  45

Ile Asn Pro Asn Ser Gly Gly Ala Asp Tyr Ala Gln Lys Leu Gln Gly
    50                  55                  60

Arg Val Thr Met Thr Thr Asp Thr Ser Thr Ser Thr Ala Tyr Met Glu
65                  70                  75                  80

Leu Arg Ser Leu Arg Ser Asp Asp Thr Ala Val Tyr Tyr Cys Ala Arg
                85                  90                  95

Glu Gly Tyr Ala Trp Gly Ala Phe Asp Ile Trp Gly Gln Gly Thr Met
            100                 105                 110

Val Thr Val Ser Ser
            115

<210> SEQ ID NO 34
<211> LENGTH: 110
<212> TYPE: PRT
<213> ORGANISM: Homo sapiens

<400> SEQUENCE: 34

Gln Ser Val Val Thr Gln Pro Pro Ser Val Ser Ala Ala Pro Gly Gln
1               5                   10                  15

Lys Val Thr Ile Ser Cys Ser Gly Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Asn Asn Glu Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Ala Gly Val Phe Gly Gly Gly Thr Lys Leu Thr Val Leu
            100                 105                 110

<210> SEQ ID NO 35
<211> LENGTH: 120
<212> TYPE: PRT
<213> ORGANISM: Homo sapiens

<400> SEQUENCE: 35

Glu Val Gln Leu Val Gln Ser Gly Ala Glu Val Arg Lys Pro Gly Ala
1               5                   10                  15

Ser Val Lys Val Ser Cys Lys Ala Ser Gln Tyr Thr Phe Thr Asn Tyr
            20                  25                  30
```

```
His Ile His Trp Val Arg Gln Val Pro Gly Gln Gly Leu Glu Trp Met
         35                  40                  45

Ala Met Ile Asn Pro Ser Asn Gly Asn Thr Asn Tyr Gly Gln Arg Phe
 50                  55                  60

Gln Asp Arg Val Thr Leu Thr Arg Asp Thr Ser Thr Ser Thr Ala Tyr
 65                  70                  75                  80

Met Glu Leu Ser Ser Leu Arg Ser Glu Asp Thr Ala Val Tyr Leu Cys
                 85                  90                  95

Ala Arg Asp Gly Leu Thr Phe Gly Asp Leu Leu Ala Tyr Trp Gly Gln
                100                 105                 110

Gly Thr Leu Val Thr Val Ser Ser
            115                 120

<210> SEQ ID NO 36
<211> LENGTH: 110
<212> TYPE: PRT
<213> ORGANISM: Homo sapiens

<400> SEQUENCE: 36

Gln Ser Val Leu Thr Gln Pro Pro Ser Ala Ser Gly Thr Pro Gly Gln
1               5                   10                  15

Ser Val Thr Ile Ser Cys Ser Gly Ser Ser Asn Ile Gly Gly Asn
                 20                  25                  30

Thr Val Asn Trp Tyr Gln Gln Phe Pro Gly Thr Ala Pro Lys Leu Leu
             35                  40                  45

Met Tyr Ile Asn Asn Leu Arg Pro Ala Gly Val Pro Asp Arg Phe Ser
 50                  55                  60

Gly Ser Lys Ser Gly Thr Ser Ala Ser Leu Val Ile Ser Gly Leu Gln
 65                  70                  75                  80

Ser Glu Asp Glu Ala Asp Tyr Tyr Cys Ala Ser Trp Asp Asp Ser Leu
                 85                  90                  95

Ser Gly Leu Val Phe Gly Gly Gly Thr Lys Leu Thr Val Leu
                100                 105                 110

<210> SEQ ID NO 37
<211> LENGTH: 122
<212> TYPE: PRT
<213> ORGANISM: Homo sapiens

<400> SEQUENCE: 37

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
                 20                  25                  30

Ser Met Asn Trp Val Arg Gln Ala Pro Gly Lys Gly Leu Glu Trp Val
             35                  40                  45

Ser Ser Ile Ser Ser Ser Ser Tyr Ile Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Asp Glu Asp Thr Ala Val Tyr Tyr Cys
                 85                  90                  95

Ala Arg Glu Ile Leu Thr Gly Tyr Tyr Pro Asp Ala Phe Asp Met Trp
                100                 105                 110

Gly Gln Gly Thr Met Val Thr Val Ser Ser
            115                 120
```

```
<210> SEQ ID NO 38
<211> LENGTH: 108
<212> TYPE: PRT
<213> ORGANISM: Homo sapiens

<400> SEQUENCE: 38

Ser Tyr Glu Leu Met Gln Pro Pro Ser Val Ser Val Ala Pro Gly Lys
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Val Val Ile Tyr
        35                  40                  45

Tyr Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Tyr Val Phe Gly Thr Gly Thr Lys Leu Thr Val Leu
            100                 105

<210> SEQ ID NO 39
<211> LENGTH: 118
<212> TYPE: PRT
<213> ORGANISM: Homo sapiens

<400> SEQUENCE: 39

Glu Val Gln Leu Leu Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Phe Gly Glu Asp Leu Phe Asp Tyr Trp Gly Gln Gly Thr
            100                 105                 110

Leu Val Thr Val Ser Ser
        115

<210> SEQ ID NO 40
<211> LENGTH: 108
<212> TYPE: PRT
<213> ORGANISM: Homo sapiens

<400> SEQUENCE: 40

Gln Ser Val Leu Thr Gln Pro Pro Ser Val Ser Val Ala Pro Gly Lys
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Leu Leu Val Ile Tyr
        35                  40                  45

Tyr Asp Thr Asp Arg Pro Ser Gly Ile Pro Glu Arg Phe Ser Gly Ser
```

```
                    50                   55                  60
Asn Ser Glu Asn Thr Ala Thr Leu Thr Ile Ser Gly Val Glu Ala Gly
 65                  70                  75                  80

Asp Glu Ala Asp Tyr Tyr Cys Gln Val Trp Asp Ile Gly Ser Asp Gln
                 85                  90                  95

Val Val Phe Gly Thr Gly Thr Lys Val Thr Val Leu
            100                 105
```

<210> SEQ ID NO 41
<211> LENGTH: 123
<212> TYPE: PRT
<213> ORGANISM: Homo sapiens

<400> SEQUENCE: 41

```
Gln Val Gln Leu Val Glu Ser Gly Gly Gly Leu Val Gln Pro Gly Gly
 1               5                  10                  15

Ser Leu Arg Leu Ser Cys Val Ala Ser Gly Phe Thr Phe Ser Ser Tyr
             20                  25                  30

Trp Met Ser Trp Val Arg Gln Ala Pro Gly Lys Gly Leu Glu Trp Val
         35                  40                  45

Ala Tyr Ile Asn Leu Asp Gly Ser Glu Lys Asp Tyr Val Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Leu Tyr Tyr Cys
                 85                  90                  95

Ala Lys Ala Tyr Ser Ser Ser Trp Leu Leu Ser Gly Met Asp Val
            100                 105                 110

Trp Gly Gln Gly Thr Thr Val Thr Val Ser Ser
        115                 120
```

<210> SEQ ID NO 42
<211> LENGTH: 111
<212> TYPE: PRT
<213> ORGANISM: Homo sapiens

<400> SEQUENCE: 42

```
Ser Tyr Glu Leu Thr Gln Pro Ala Ser Val Ser Gly Ser Pro Gly Gln
 1               5                  10                  15

Ser Ile Thr Ile Ser Cys Thr Gly Thr Ser Ser Asp Val Gly Asn Tyr
             20                  25                  30

Asn Ser Val Ser Trp Tyr Gln Gln His Pro Gly Lys Ala Pro Glu Leu
         35                  40                  45

Met Ile Tyr Asp Val Asn Asn Arg Pro Ser Gly Val Ser Asn Arg Phe
 50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Ser Ser Tyr Thr Ser Ser
                 85                  90                  95

Ser Thr Leu Val Phe Gly Gly Gly Thr Gln Leu Thr Val Leu Gly
            100                 105                 110
```

<210> SEQ ID NO 43
<211> LENGTH: 122
<212> TYPE: PRT
<213> ORGANISM: Homo sapiens

<400> SEQUENCE: 43

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Ser Ser Ser Tyr
            20                  25                  30

Val Leu Asn Trp Val Arg Gln Ala Pro Gly Lys Gly Leu Glu Trp Val
            35                  40                  45

Ser Ser Ile Ser Ser Arg Gly Ser Tyr Ile Tyr Tyr Ala Asp Ser Val
50                      55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Arg Ala Gly Phe Ser Pro Val Asn Ala Phe Asp Ile Trp
            100                 105                 110

Gly Gln Gly Thr Met Val Thr Val Ser Ser
            115                 120

<210> SEQ ID NO 44
<211> LENGTH: 111
<212> TYPE: PRT
<213> ORGANISM: Homo sapiens

<400> SEQUENCE: 44

Gln Ser Val Leu Thr Gln Pro Ala Ser Val Ser Gly Ser Pro Gly Gln
1               5                   10                  15

Ser Ile Thr Ile Ser Cys Thr Gly Ser Ser Ser Asp Val Gly Ser Tyr
            20                  25                  30

Asn Leu Val Ser Trp Tyr Gln Gln His Pro Gly Lys Ala Pro Lys Leu
            35                  40                  45

Met Ile Tyr Asp Asp Asn Arg Arg Pro Ser Gly Ile Ser Thr Arg Phe
50                  55                  60

Ser Gly Ser Lys Ser Gly Asn Thr Ala Ser Leu Thr Val Ser Gly Leu
65                  70                  75                  80

Gln Ala Glu Asp Glu Ala Tyr Tyr Tyr Cys Ser Ser Tyr Ala Gly Arg
                85                  90                  95

Asn Asn Asp Val Ile Phe Gly Gly Gly Thr Gln Leu Thr Val Leu
            100                 105                 110

<210> SEQ ID NO 45
<211> LENGTH: 121
<212> TYPE: PRT
<213> ORGANISM: Homo sapiens

<400> SEQUENCE: 45

Gln Val Gln Leu Val Glu Ser Gly Gly Gly Leu Val Gln Pro Gly Gly
1               5                   10                  15

Ser Leu Arg Leu Ala Cys Ala Ala Ser Gly Phe Thr Phe Ser Asn Tyr
            20                  25                  30

Glu Met Asn Trp Val Arg Gln Ala Pro Gly Lys Gly Leu Glu Trp Val
            35                  40                  45

Ala Thr Ile Ser Asp Asp Ser Val Tyr Lys Tyr Tyr Ala Asp Ser Val
50                  55                  60

Lys Gly Arg Phe Thr Ile Ser Arg Asp Asn Ser Lys Ala Leu Phe Tyr
65                  70                  75                  80

Leu Gln Met Asp Ser Leu Thr Phe Glu Asp Thr Ala Ile Tyr Tyr Cys
                85                  90                  95

```
Ala Arg Asp Pro Gly Asp Ser Leu Gly Tyr Phe Gln His Trp Gly
            100                 105                 110

Gln Gly Thr Leu Val Thr Val Ser Ser
        115                 120

<210> SEQ ID NO 46
<211> LENGTH: 116
<212> TYPE: PRT
<213> ORGANISM: Homo sapiens

<400> SEQUENCE: 46

Gln Ala Gly Leu Thr Gln Pro Pro Ser Ala Ser Ala Ser Pro Gly Asp
1               5                   10                  15

Ser Val Thr Leu Thr Cys Thr Leu Ser Ser Asp His Ser Asp Tyr Lys
                20                  25                  30

Val Asp Trp Tyr Gln Gln Arg Pro Gly Lys Gly Pro Arg Phe Val Met
            35                  40                  45

Arg Val Gly Thr Gly Gly Ile Val Gly Val Lys Gly Asp Gly Ile Pro
    50                  55                  60

Asp Arg Phe Ser Val Trp Gly Ser Gly Pro Asn Arg Tyr Leu Thr Ile
65                  70                  75                  80

Lys Asn Ile Gln Glu Glu Asp Glu Ser Asp Tyr His Cys Gly Ser Asp
                85                  90                  95

His Gly Ser Gly Asn Asn Tyr Val Tyr Val Phe Gly Gly Gly Thr Lys
            100                 105                 110

Leu Thr Val Leu
        115

<210> SEQ ID NO 47
<211> LENGTH: 119
<212> TYPE: PRT
<213> ORGANISM: Homo sapiens
<220> FEATURE:
<221> NAME/KEY: misc_feature
<222> LOCATION: (19)..(20)
<223> OTHER INFORMATION: Xaa can be any naturally occurring amino acid

<400> SEQUENCE: 47

Gln Val Gln Leu Gln Gln Trp Gly Ala Gly Leu Leu Lys Pro Ser Glu
1               5                   10                  15

Thr Leu Xaa Xaa Thr Cys Ala Val Tyr Gly Gly Ser Phe Ser Gly Tyr
                20                  25                  30

Tyr Trp Ser Trp Ile Arg Gln Pro Pro Gly Lys Gly Leu Glu Trp Ile
            35                  40                  45

Gly Glu Ile Asn His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Gln Leu Asn Ser Val Thr Pro Glu Asp Thr Ala Val Tyr Tyr Cys Val
                85                  90                  95

Arg Asp Asp Gly Met Gly Leu Asp Ala Leu Asp Ile Trp Gly Gln Gly
            100                 105                 110

Thr Met Val Thr Val Ser Ser
        115

<210> SEQ ID NO 48
<211> LENGTH: 110
<212> TYPE: PRT
```

```
<213> ORGANISM: Homo sapiens

<400> SEQUENCE: 48

Gln Ser Ala Leu Thr Gln Pro Pro Ser Val Ser Ala Pro Gly Gln
1               5                   10                  15

Lys Val Thr Ile Ser Cys Ser Gly Ser Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Ala Glu Val Phe Gly Gly Gly Thr Lys Val Thr Val Leu
            100                 105                 110

<210> SEQ ID NO 49
<211> LENGTH: 115
<212> TYPE: PRT
<213> ORGANISM: Homo sapiens

<400> SEQUENCE: 49

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asn Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Gly Gly Gly Tyr Tyr Ser Tyr Trp Gly Gln Gly Thr Leu Val Thr
            100                 105                 110

Val Ser Ser
        115

<210> SEQ ID NO 50
<211> LENGTH: 111
<212> TYPE: PRT
<213> ORGANISM: Homo sapiens

<400> SEQUENCE: 50

Leu Pro Val Leu Thr Gln Pro Pro Ser Ala Ser Gly Ser Pro Gly Gln
1               5                   10                  15

Ser Val Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Glu Val Ser Lys Arg Pro Ser Gly Val Pro Asp Arg Phe
    50                  55                  60

Ser Gly Ser Lys Ser Gly Asn Thr Ala Ser Leu Thr Val Ser Gly Leu
65                  70                  75                  80
```

```
Gln Ala Glu Asp Glu Ala Asp Tyr Tyr Cys Ser Ser Tyr Ala Gly Ser
                85                  90                  95

Asn Asn Pro Tyr Val Phe Gly Thr Gly Thr Lys Val Thr Val Leu
            100                 105                 110

<210> SEQ ID NO 51
<211> LENGTH: 126
<212> TYPE: PRT
<213> ORGANISM: Homo sapiens

<400> SEQUENCE: 51

Gln Val Gln Leu Val Glu Ser Gly Gly Gly Leu Ile Gln Pro Gly Gly
1               5                   10                  15

Ser Val Lys Leu Ser Cys Ala Ala Ser Gly Phe Thr Val Ser Ser Asn
            20                  25                  30

Tyr Met Ser Trp Val Arg Gln Ala Pro Gly Lys Gly Leu Glu Trp Val
        35                  40                  45

Ala Val Ile Ser Tyr Asp Gly Ser Phe Glu Tyr Tyr Gly Glu Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Arg Pro Glu Asp Thr Ala Val Tyr Tyr Cys
                85                  90                  95

Ala Lys Asp Thr Pro Tyr Tyr Tyr Asp Ser Ser Gly Gln Ser Gly Asp
            100                 105                 110

Tyr Phe Asp His Trp Gly Gln Gly Ala Leu Val Thr Val Ser
        115                 120                 125

<210> SEQ ID NO 52
<211> LENGTH: 111
<212> TYPE: PRT
<213> ORGANISM: Homo sapiens

<400> SEQUENCE: 52

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Lys Ser Gly Asn Thr Ala Ser Leu Thr Val Ser Gly Leu
65                  70                  75                  80

Gln Ala Glu Asp Glu Ala Asp Tyr Tyr Cys Ala Ser Trp Asp Asp Ser
                85                  90                  95

Leu Asn Ser Pro Val Phe Gly Gly Gly Thr Lys Leu Thr Val Leu
            100                 105                 110

<210> SEQ ID NO 53
<211> LENGTH: 117
<212> TYPE: PRT
<213> ORGANISM: Homo sapiens

<400> SEQUENCE: 53

Glu Val Gln Leu Val Glu Ser Gly Gly Gly Leu Ile Gln Pro Gly Gly
1               5                   10                  15
```

Ser Leu Arg Leu Ser Cys Ala Ala Ser Gly Phe Thr Val Ser Ser Asn
            20                  25                  30

Tyr Met Ser Trp Val Arg Gln Ala Pro Gly Lys Gly Leu Glu Trp Val
        35                  40                  45

Ser Val Ile Tyr Ser Gly Gly Ser Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Asp Phe Gly Val Gly Ala Val Asp Tyr Trp Gly Gln Gly Thr Leu
            100                 105                 110

Val Thr Val Ser Ser
        115

<210> SEQ ID NO 54
<211> LENGTH: 112
<212> TYPE: PRT
<213> ORGANISM: Homo sapiens

<400> SEQUENCE: 54

Gln Ser Val Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Phe Val Ser Trp Tyr Gln Gln His Pro Gly Lys Ala Pro Lys Leu
        35                  40                  45

Met Ile Tyr Asp Val Thr Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Asp Ser
                85                  90                  95

Ser Thr Leu Asp Val Val Phe Gly Gly Gly Thr Lys Val Thr Val Leu
            100                 105                 110

<210> SEQ ID NO 55
<211> LENGTH: 121
<212> TYPE: PRT
<213> ORGANISM: Homo sapiens

<400> SEQUENCE: 55

Gln Leu Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Asn Ser Ala
            20                  25                  30

Gly Tyr Tyr Trp Thr Trp Ile Arg Gln His Pro Gly Lys Gly Leu Glu
        35                  40                  45

Trp Ile Gly Ser Ile Tyr Tyr Ser Gly Ser Thr Tyr Tyr Asn Pro Ser
    50                  55                  60

Leu Lys Ser Arg Val Ser Met Ser Gln Asp Thr Ser Lys Asn Gln Phe
65                  70                  75                  80

Ser Leu Lys Leu Ser Ser Leu Thr Ala Ala Asp Thr Ala Val Tyr Tyr
                85                  90                  95

Cys Ala Arg Glu Val Gly Val Val Pro Glu Tyr Met Asp Val Trp Gly
            100                 105                 110

Gln Gly Thr Thr Val Thr Val Ser Ser
            115                 120

<210> SEQ ID NO 56
<211> LENGTH: 110
<212> TYPE: PRT
<213> ORGANISM: Homo sapiens
<220> FEATURE:
<221> NAME/KEY: misc_feature
<222> LOCATION: (104)..(104)
<223> OTHER INFORMATION: Xaa can be any naturally occurring amino acid

<400> SEQUENCE: 56

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Asp Val Gly Gly Tyr
            20                  25                  30

Asn Tyr Val Ser Trp Tyr Gln Gln His Pro Gly Lys Gly Pro Lys Leu
        35                  40                  45

Met Ile Tyr Asp Val Ser Lys Arg Pro Ser Gly Val Ser Gly Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Leu Leu Phe Gly Gly Xaa Thr Lys Leu Thr Val Leu
            100                 105                 110

<210> SEQ ID NO 57
<211> LENGTH: 117
<212> TYPE: PRT
<213> ORGANISM: Homo sapiens

<400> SEQUENCE: 57

Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Gly Phe Ile Arg Ser Glu Thr Tyr Gly Gly Thr Thr Gln Thr Ala Ala
    50                  55                  60

Ser Val Lys Gly Arg Phe Ser Ile Ser Arg Asp Asp Ser Gln Gly Ile
65                  70                  75                  80

Ala Tyr Leu Gln Met Asp Ser Leu Lys Thr Glu Asp Thr Ala Val Tyr
                85                  90                  95

Phe Cys Ala Arg Ser Gly Arg Gly Asp Phe Trp Gly Gln Gly Thr Leu
            100                 105                 110

Val Thr Val Ser Ser
            115

<210> SEQ ID NO 58
<211> LENGTH: 110
<212> TYPE: PRT
<213> ORGANISM: Homo sapiens

<400> SEQUENCE: 58

```
Gln Ala Gly Leu Thr Gln Pro Arg Ser Val Ser Gly Ser Pro Gly Gln
1               5                   10                  15

Ser Val Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Leu Ile Tyr Asp Val Asn Asn Arg Pro Ser Gly Val Pro Asp Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Thr Thr Gln Val Phe Gly Gly Gly Thr Lys Val Thr Val Leu
            100                 105                 110
```

<210> SEQ ID NO 59
<211> LENGTH: 126
<212> TYPE: PRT
<213> ORGANISM: Homo sapiens
<220> FEATURE:
<221> NAME/KEY: misc_feature
<222> LOCATION: (19)..(19)
<223> OTHER INFORMATION: Xaa can be any naturally occurring amino acid

<400> SEQUENCE: 59

```
Gln Val Gln Leu Gln Glu Ser Gly Gly Gly Val Val Gln Pro Gly Arg
1               5                   10                  15

Ser Leu Xaa Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Trp Asp Val Ala Ser Thr Val Glu Ala Thr Asp Gly
            100                 105                 110

Met Asp Val Trp Gly Gln Gly Thr Thr Val Thr Val Ser Ser
        115                 120                 125
```

<210> SEQ ID NO 60
<211> LENGTH: 109
<212> TYPE: PRT
<213> ORGANISM: Homo sapiens

<400> SEQUENCE: 60

```
Gln Ala Gly Leu Thr Gln Pro Pro Ser Ala Ser Gly Ser Pro Gly Gln
1               5                   10                  15

Ser Val Thr Ile Ser Cys Thr Gly Thr Ser Ser Asp Val Gly Gly Tyr
            20                  25                  30
```

-continued

```
Asn Tyr Val Ser Trp Tyr Gln Gln His Pro Gly Lys Ala Pro Lys Leu
        35                  40              45

Met Ile Tyr Glu Val Asn Lys Arg Pro Ser Gly Ile Pro Asp Arg Phe
    50              55                  60

Ser Gly Ser Lys Ser Asp Ser Thr Ala Ser Leu Thr Ile Ser Gly Leu
65              70                  75                      80

Gln Ala Glu Asp Glu Ala Asn Tyr Tyr Cys Ile Ser Tyr Thr Ser Ser
            85                  90              95

Thr Thr Trp Val Phe Gly Gly Gly Thr Gln Leu Thr Val
            100                 105
```